(12) United States Patent
Goldman et al.

(10) Patent No.: US 12,102,590 B2
(45) Date of Patent: Oct. 1, 2024

(54) MEDICAL DEVICE SYSTEM AND HARDWARE FOR SENSOR DATA ACQUISITION

(71) Applicant: ZOLL Medical Corporation, Chelmsford, MA (US)

(72) Inventors: Dan E Goldman, Shrewsbury, MA (US); Suzanne Crowell, Beverly, MA (US); Frederick K Newey, Pelham, NH (US); Allan S Baucom, Boxboro, MA (US); Gary A Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 861 days.

(21) Appl. No.: 17/211,900

(22) Filed: Mar. 25, 2021

(65) Prior Publication Data
US 2021/0298991 A1    Sep. 30, 2021

Related U.S. Application Data

(60) Provisional application No. 63/001,565, filed on Mar. 30, 2020.

(51) Int. Cl.
*A61H 31/00*    (2006.01)

(52) U.S. Cl.
CPC ... *A61H 31/005* (2013.01); *A61H 2201/0188* (2013.01); *A61H 2201/5043* (2013.01);
(Continued)

(58) Field of Classification Search
CPC .......... A61H 31/005; A61H 2201/5043; A61H 2201/5087; A61H 2230/04
See application file for complete search history.

(56) References Cited

U.S. PATENT DOCUMENTS

| | | |
|---|---|---|
| 5,086,391 A | 2/1992 | Chambers |
| 5,218,969 A | 6/1993 | Bredesen et al. |

(Continued)

FOREIGN PATENT DOCUMENTS

| | | |
|---|---|---|
| CN | 2674710 | 1/2005 |
| CN | 101226452 | 7/2008 |

(Continued)

OTHER PUBLICATIONS

PCT Search Report and Written Opinion for PCT Application No. PCT/US2021/024025, dated Oct. 5, 2021, 22 pages.
(Continued)

*Primary Examiner* — Neil Abrams
(74) *Attorney, Agent, or Firm* — The Webb Law Firm

(57) ABSTRACT

A medical device system for providing sensor data capture includes a medical device that may include one or more removably coupled sensor hubs and that includes a display to provide sensor data and at least one data interface (DI) port that may be a sensor-agnostic DI (SA-DI) port and a data transfer cable that may be compatible with the sensor-agnostic DI port and includes a first electromechanical connector configured to detachably couple to the SA-DI port and a second electromechanical connector configured to couple to the sensor and that includes a cable memory and processor configured to execute stored software to format sensor data according to a protocol of the SA-DI port, an authentication circuit, and a cable isolation device to limit patient leakage current flow from the medical device to the sensor and to electrically isolate the authentication circuit from the cable processor and the cable memory.

25 Claims, 25 Drawing Sheets

(52) U.S. Cl.
CPC ............ *A61H 2201/5048* (2013.01); *A61H 2201/5087* (2013.01); *A61H 2230/04* (2013.01); *A61H 2230/207* (2013.01); *A61H 2230/40* (2013.01); *A61H 2230/50* (2013.01)

(56) References Cited

U.S. PATENT DOCUMENTS

| | | | |
|---|---|---|---|
| 5,255,187 A | 10/1993 | Sorensen | |
| 5,368,041 A | 11/1994 | Shambroom | |
| 5,375,604 A | 12/1994 | Kelly et al. | |
| 5,626,151 A | 5/1997 | Linden | |
| 5,782,878 A | 7/1998 | Morgan et al. | |
| 5,813,403 A | 9/1998 | Soller et al. | |
| 5,853,005 A | 12/1998 | Scanlon | |
| 6,024,699 A | 2/2000 | Surwit et al. | |
| 6,055,447 A | 4/2000 | Weil et al. | |
| 6,057,758 A | 5/2000 | Dempsey et al. | |
| 6,141,584 A | 10/2000 | Rockwell et al. | |
| 6,157,313 A | 12/2000 | Emmermann | |
| 6,201,992 B1 | 3/2001 | Freeman | |
| 6,261,238 B1 | 7/2001 | Gavriely | |
| 6,270,456 B1 | 8/2001 | Iliff | |
| 6,321,113 B1 | 11/2001 | Parker et al. | |
| 6,370,427 B1 | 4/2002 | Alt et al. | |
| 6,443,889 B1 | 9/2002 | Groth et al. | |
| 6,488,629 B1 | 12/2002 | Saetre et al. | |
| 6,551,243 B2 | 4/2003 | Bocionek et al. | |
| 6,564,088 B1 | 5/2003 | Soller et al. | |
| 6,572,560 B1 | 6/2003 | Watrous et al. | |
| 6,589,267 B1 * | 7/2003 | Hui | A61H 31/008 601/152 |
| 6,725,447 B1 | 4/2004 | Gilman et al. | |
| 6,766,188 B2 | 7/2004 | Soller | |
| 6,829,501 B2 | 12/2004 | Nielsen et al. | |
| 6,849,045 B2 | 2/2005 | Iliff | |
| 6,865,418 B2 | 3/2005 | Merry | |
| 6,898,462 B2 | 5/2005 | Rock et al. | |
| 6,957,102 B2 | 10/2005 | Silver et al. | |
| 7,006,865 B1 | 2/2006 | Cohen et al. | |
| 7,020,844 B2 | 3/2006 | Trevino et al. | |
| 7,072,840 B1 | 7/2006 | Mayaud | |
| 7,107,095 B2 | 9/2006 | Manolas | |
| 7,164,945 B2 | 1/2007 | Hamilton et al. | |
| 7,184,963 B1 | 2/2007 | Shannon | |
| 7,212,128 B2 | 5/2007 | Schenker | |
| 7,213,009 B2 | 5/2007 | Pestotnik et al. | |
| 7,241,180 B1 | 7/2007 | Rentas Torres | |
| 7,306,560 B2 | 12/2007 | Iliff | |
| 7,421,647 B2 | 9/2008 | Reiner | |
| 7,447,643 B1 | 11/2008 | Olson et al. | |
| 7,510,526 B2 | 3/2009 | Merry et al. | |
| 7,546,163 B2 | 6/2009 | Bischoff et al. | |
| 7,558,622 B2 | 7/2009 | Tran | |
| 7,742,931 B2 | 6/2010 | McElwain Miller | |
| 7,779,183 B2 | 8/2010 | Koehler et al. | |
| 7,835,925 B2 | 11/2010 | Roe et al. | |
| 7,853,327 B2 | 12/2010 | Patangay et al. | |
| 7,945,452 B2 | 5/2011 | Fathallah et al. | |
| 7,957,798 B2 | 6/2011 | Pearce et al. | |
| 7,986,309 B2 | 7/2011 | Kim | |
| 8,068,104 B2 | 11/2011 | Rampersad | |
| 8,098,423 B2 | 1/2012 | Islam | |
| 8,126,728 B2 | 2/2012 | Dicks et al. | |
| 8,137,270 B2 | 3/2012 | Keenan et al. | |
| 8,255,026 B1 | 8/2012 | Al-Ali | |
| 8,267,084 B2 | 9/2012 | Kwok | |
| 8,335,694 B2 | 12/2012 | Reiner | |
| 8,337,404 B2 | 12/2012 | Osorio | |
| 8,352,021 B2 | 1/2013 | Scheib | |
| 8,355,928 B2 | 1/2013 | Spahn | |
| 8,392,217 B2 | 3/2013 | Iliff | |
| 8,487,881 B2 | 7/2013 | Keenan | |
| 8,510,126 B2 | 8/2013 | Martin et al. | |
| 8,527,049 B2 | 9/2013 | Koh et al. | |
| 8,587,426 B2 | 11/2013 | Bloem | |
| 8,744,543 B2 | 6/2014 | Li et al. | |
| 8,790,257 B2 | 7/2014 | Libbus et al. | |
| 8,900,141 B2 | 12/2014 | Smith et al. | |
| 8,923,918 B2 | 12/2014 | Kreger et al. | |
| 8,956,292 B2 | 2/2015 | Wekell et al. | |
| 8,997,736 B2 | 4/2015 | Smith | |
| 9,106,038 B2 * | 8/2015 | Telfort | H01R 31/065 |
| 9,286,440 B1 | 3/2016 | Carter et al. | |
| 9,289,621 B2 | 3/2016 | Aoyama et al. | |
| 9,492,084 B2 | 11/2016 | Behar et al. | |
| 9,596,989 B2 | 3/2017 | Morris | |
| 9,636,513 B2 | 5/2017 | Kuo et al. | |
| 9,658,756 B2 | 5/2017 | Freeman et al. | |
| 9,728,907 B2 | 8/2017 | Mann et al. | |
| 9,768,644 B2 | 9/2017 | Stever et al. | |
| 9,980,674 B2 | 5/2018 | Packer et al. | |
| 10,091,301 B2 | 10/2018 | Delisle et al. | |
| 10,092,248 B2 | 10/2018 | Tanaka et al. | |
| 10,122,490 B2 | 11/2018 | Curtis et al. | |
| 10,137,265 B2 | 11/2018 | Freeman et al. | |
| 10,146,912 B2 | 12/2018 | Drysdale et al. | |
| 10,191,738 B1 | 1/2019 | Milota et al. | |
| 10,303,852 B2 | 5/2019 | Peterson et al. | |
| 10,410,748 B2 | 9/2019 | Fitzgerald et al. | |
| 10,413,742 B2 | 9/2019 | Mcmahon et al. | |
| 10,437,959 B2 | 10/2019 | Dyell et al. | |
| 10,737,105 B2 | 8/2020 | Andrews et al. | |
| 2001/0047140 A1 | 11/2001 | Freeman | |
| 2002/0184055 A1 | 12/2002 | Naghavi et al. | |
| 2003/0028219 A1 | 2/2003 | Powers et al. | |
| 2003/0036683 A1 | 2/2003 | Kehr et al. | |
| 2003/0036924 A1 | 2/2003 | Rosen et al. | |
| 2004/0042735 A1 | 3/2004 | Ma | |
| 2004/0049233 A1 | 3/2004 | Edwards | |
| 2004/0064169 A1 | 4/2004 | Briscoe et al. | |
| 2004/0064342 A1 | 4/2004 | Browne et al. | |
| 2004/0143298 A1 | 7/2004 | Nova et al. | |
| 2004/0147818 A1 | 7/2004 | Levy et al. | |
| 2004/0152954 A1 | 8/2004 | Pearce et al. | |
| 2004/0214148 A1 | 10/2004 | Salvino et al. | |
| 2005/0187472 A1 | 8/2005 | Lysyansky et al. | |
| 2005/0277872 A1 | 12/2005 | Colby, Jr. et al. | |
| 2006/0111933 A1 | 5/2006 | Wheeler | |
| 2006/0116908 A1 | 6/2006 | Dew et al. | |
| 2006/0122864 A1 | 6/2006 | Gottesman et al. | |
| 2006/0142648 A1 | 6/2006 | Banet et al. | |
| 2007/0032830 A1 | 2/2007 | Bowers | |
| 2007/0175980 A1 | 8/2007 | Alsafadi | |
| 2007/0191687 A1 | 8/2007 | Justus | |
| 2008/0098450 A1 | 4/2008 | Wu et al. | |
| 2008/0176199 A1 | 7/2008 | Stickney et al. | |
| 2009/0054735 A1 | 2/2009 | Higgins et al. | |
| 2009/0061678 A1 | 3/2009 | Minoo et al. | |
| 2009/0069642 A1 | 3/2009 | Gao et al. | |
| 2009/0076345 A1 | 3/2009 | Manicka et al. | |
| 2009/0089095 A1 | 4/2009 | Esham et al. | |
| 2009/0227883 A1 | 9/2009 | Zhang et al. | |
| 2009/0270931 A1 | 10/2009 | Liden | |
| 2010/0010319 A1 | 1/2010 | Tivig et al. | |
| 2010/0087883 A1 | 4/2010 | Sullivan et al. | |
| 2010/0114218 A1 | 5/2010 | Heath | |
| 2010/0161353 A1 | 6/2010 | Mayaud | |
| 2010/0249540 A1 | 9/2010 | Lisogurski | |
| 2010/0276195 A1 | 11/2010 | Balji et al. | |
| 2010/0302281 A1 | 12/2010 | Kim | |
| 2010/0305412 A1 | 12/2010 | Darrah et al. | |
| 2011/0074831 A1 | 3/2011 | Lynch et al. | |
| 2011/0118561 A1 | 5/2011 | Tari et al. | |
| 2011/0130636 A1 | 6/2011 | Daniel et al. | |
| 2011/0172550 A1 | 7/2011 | Martin et al. | |
| 2011/0208540 A1 | 8/2011 | Lord et al. | |
| 2011/0209915 A1 | 9/2011 | Telfort et al. | |
| 2011/0295078 A1 | 12/2011 | Reid et al. | |
| 2012/0123218 A1 | 5/2012 | Renes | |
| 2012/0123223 A1 | 5/2012 | Freeman et al. | |
| 2012/0278099 A1 | 11/2012 | Kelly et al. | |
| 2013/0096649 A1 | 4/2013 | Martin et al. | |
| 2013/0124090 A1 | 5/2013 | Gotschall et al. | |
| 2013/0304145 A1 | 11/2013 | Aoyama et al. | |

(56) References Cited

U.S. PATENT DOCUMENTS

| | | |
|---|---|---|
| 2014/0276143 A1 | 9/2014 | Corl |
| 2014/0286361 A1 | 9/2014 | Risher-Kelly |
| 2014/0296675 A1 | 10/2014 | Freeman et al. |
| 2015/0120249 A1 | 4/2015 | Hernke |
| 2015/0359489 A1 | 12/2015 | Baudenbacher et al. |
| 2016/0132457 A1 | 5/2016 | Castell et al. |
| 2016/0287470 A1 | 10/2016 | Lewis et al. |
| 2016/0303389 A1 | 10/2016 | Peterson et al. |
| 2017/0021183 A1 | 1/2017 | Aoyama et al. |
| 2017/0172478 A1 | 6/2017 | Lisogurski |
| 2017/0266399 A1 | 9/2017 | Campana et al. |
| 2018/0247712 A1 | 8/2018 | Muhsin et al. |
| 2018/0368804 A1* | 12/2018 | Siedenburg .......... A61B 8/4236 |
| 2019/0131742 A1 | 5/2019 | Veenstra et al. |
| 2019/0349652 A1 | 11/2019 | Greenewald et al. |
| 2019/0351245 A1 | 11/2019 | Anderson et al. |
| 2021/0298991 A1* | 9/2021 | Goldman ............. A61H 31/005 |

FOREIGN PATENT DOCUMENTS

| | | |
|---|---|---|
| CN | 101779986 | 7/2010 |
| CN | 101849241 | 9/2010 |
| CN | 107613050 | 1/2018 |
| DE | 202006012156 | 10/2006 |
| EP | 1702649 | 9/2006 |
| EP | 3362144 | 8/2018 |
| JP | 09-262213 | 10/1997 |
| JP | 2003-521972 | 7/2003 |
| JP | 2005-524436 | 8/2005 |
| JP | 2005-524498 | 8/2005 |
| JP | 2007-125151 | 5/2007 |
| JP | 2008-200111 | 9/2008 |
| JP | 6023834 | 11/2016 |
| RU | 169266 | 3/2017 |
| RU | 2661796 | 7/2018 |
| WO | 20080086496 | 7/2008 |
| WO | 20120152133 | 11/2012 |
| WO | 20180193142 | 10/2018 |
| WO | 2020115803 | 6/2020 |

OTHER PUBLICATIONS

Partial International Search Report for PCT/US2021/024025, mailed on Jul. 12, 2021, 13 pages.

DG Interconnect, eclipse QL-5 Miniature Series—An Advance Interconnect Solution Data Sheet, 2 pages.

Hernandez, et al., "C.A.U.S.E.: Cardiac Arrest Ultra-sound Exam—A Better Approach to Managing Patients in Primary Non-arrhythmogenic Cardiac Arrest," Resuscitation, vol. 76, Issue 2, pp. 198-206 (Feb. 2008).

* cited by examiner

MEDICAL DEVICE SYSTEM AND HARDWARE FOR SENSOR DATA ACQUISITION

CROSS-REFERENCE TO RELATED APPLICATIONS

This application claims priority under 35 U.S.C. § 119(e) to U.S. Provisional Application Ser. No. 63/001,565, titled "MEDICAL DEVICE SYSTEM AND HARDWARE FOR SENSOR DATA ACQUISITION," filed Mar. 30, 2020, which is hereby incorporated herein by reference in its entirety.

BACKGROUND

Medical devices such as patient monitors and defibrillators obtain physiological and medical treatment data via sensors. For example, physiological data may include patient data such as vital signs, electrocardiograms (ECGs), pulse oximetry data, and/or capnography data. Medical treatment data may include treatment administration metrics such as cardiopulmonary resuscitation (CPR) parameters. Sensors configured to provide this data may couple to the medical devices via cable connections to data interface ports. The data interface ports capture sensor data and provide this captured data to the medical device for analysis and display.

SUMMARY

An example of a data transfer cable for providing data communications between a sensor for collecting medical data and a sensor-agnostic data interface (DI) port on a medical device according to the disclosure includes a cable including conductive wires disposed within a continuous insulative sheath, a first electromechanical connector fixedly fastened to a first end of the cable and including a housing, a first electrical mating disposed within the housing at an open end of the housing and configured to detachably couple to the sensor, data interface circuitry disposed within the housing and electrically coupled to the first electrical mating and to the conductive wires of the cable and including a cable memory, a cable processor, and an isolation device for limiting patient leakage current flow from the medical device to the sensor, the isolation device configured to transfer power across an isolation barrier uni-directionally towards the cable processor, and transmit communication signals bi-directionally across the isolation barrier, and a second electromechanical connector fixedly fastened to a second end of the cable, the second electromechanical connector including cable contacts electrically coupled to the conductive wires of the cable and configured to detachably electromechanically couple the data transfer cable to the sensor-agnostic DI port.

Implementations of such a system may include one or more of the following features. The isolation device may be configured to transmit an amount of power specific to the sensor across the isolation barrier. The isolation device may be configured to transmit 0.1-1 watts. The isolation device may be one of a double capacitive isolation barrier device, a digital isolator device, and an optical isolator device. The cable contacts may include at least (a) at least two communication cable contacts, (b) at least one power cable contact, and (c) at least one ground cable contact. Each of the cable contacts may be electrically coupled to at least one of the conductive wires. The cable contacts may include at least one connection detection cable contact for electrically detecting a connection between the data transfer cable and the sensor-agnostic DI port. The data interface circuitry may include an authentication circuit and the cable contacts may include at least one authentication cable contact. The authentication circuit may be configured to (a) receive an AU/ID request via the at least one authentication cable contact, and (b) send AU/ID information in response to the received AU/ID request, in an absence of power transmission to the data transfer cable from the sensor-agnostic DI port. The authentication circuit may be configured to include encrypted AU/ID information for the sensor in the AU/ID information. The encrypted AU/ID information may include identification information for a manufacturer of the sensor. The cable processor may be configured to receive, from the sensor-agnostic DI port via the communication signals transmitted by the isolation device, a request for sensor information comprising unencrypted AU/ID information stored in the cable memory, execute software stored in the cable memory to determine the requested sensor information, and send the sensor information to the sensor-agnostic DI port via the communication signals transmitted by the isolation device. The cable processor may be configured to receive a request for sensor data streams from the sensor-agnostic DI port via the communication signals transmitted by the isolation device, execute software stored in the cable memory to format sensor data in a sensor-agnostic data format according to a protocol of the sensor-agnostic DI port, and send the sensor data streams in the sensor-agnostic data format to the sensor-agnostic DI port via the communication signals transmitted by the isolation device. The data interface circuitry may include an analog-to-digital converter. The data transfer cable may include a noise shield between the isolation device and the cable processor. The data transfer cable may include at least one illumination device disposed on the cable and configured to illuminate in a color based on a type of the sensor. The at least one illumination device may include a light emitting diode (LED). The at least one illumination device may include a band that surrounds a circumference of the data transfer cable. The data transfer cable may include a microphone communicatively coupled to the cable processor and configured to capture voice input. The cable processor may be configured to cause the at least one illumination device to illuminate in response to the voice input. The cable processor may be configured to recognize a sensor identification query from the voice input. The at least one illumination device may provide infrared illumination. The data transfer cable may include a low light sensor electrically coupled to the at least one illumination device and configured to disable illumination under low light conditions. The data transfer cable may include a user interface display configured to provide caregiver feedback and disposed on a display housing positioned along the cable. The caregiver feedback may include one or more of cardiopulmonary resuscitation chest compression feedback and bag valve mask feedback. The sensor may be one of an invasive blood pressure sensor, a non-invasive blood pressure sensor, a temperature sensor, a pulse oximetry sensor, a capnography sensor, and an airway flow sensor. The sensor may be an ECG sensor.

An example of a patient monitoring and treatment system for providing sensor data capture capabilities according to the disclosure includes a medical device that includes a display, at least one sensor-agnostic data interface (DI) port including a plurality of electrical contacts configured to enable power transfer to a sensor and data communications between the sensor and the medical device, a host processor, memory, and associated circuitry, and a data transfer cable that includes a first electromechanical connector configured to detachably couple the data transfer cable to the at least one sensor-agnostic DI port, and a second electromechanical connector configured to detachably couple to the sensor and including a plurality of cable contacts, each cable contact configured to detachably mate with a corresponding contact of the plurality of electrical contacts, a cable memory, a cable processor configured to execute software stored in the cable memory to format sensor data in a sensor-agnostic data format according to a protocol of the at least one sensor-agnostic DI port, an authentication circuit configured to provide encrypted authentication/identification (AU/ID) information for the sensor to the medical device, and a cable isolation device for limiting patient leakage current flow from the medical device to the sensor, the cable isolation device configured to electrically isolate the authentication circuit from the cable processor and the cable memory and the display is configured to provide at least one visual representation of the sensor data.

Implementations of such a system may include one or more of the following features. The at least one sensor-agnostic DI port excludes an isolation device for limiting patient leakage current flow from the medical device to the sensor. The plurality of electrical contacts may include at least (a) at least one authentication contact, (b) at least two communication contacts, (c) at least one power contact, and (d) at least one ground cable contact. The host processor may be configured to send an AU/ID request via the at least one authentication contact. The authentication circuit may be configured to send encrypted AU/ID information in response to the received AU/ID request in an absence of power transmission to the data transfer cable from the at least one sensor-agnostic DI port. The plurality of electrical contacts may include at least one connection detection contact for electrically detecting a connection and a disconnection between the data transfer cable and the at least one sensor-agnostic DI port. The medical device may include a plurality of sensor-agnostic DI ports. The host processor may be configured to limit a number of sensor-agnostic data interface ports that concurrently transfer power to less than a total number of sensor-agnostic data interface ports. The host processor may be configured to limit the number of sensor-agnostic DI ports based on the encrypted AU/ID information. The host processor may be configured to limit the number of sensor-agnostic DI ports to three ports connected to an invasive blood pressure sensor. The host processor may be configured to limit the number of sensor-agnostic DI ports based on sensor priority. An airway flow sensor and/or an invasive blood pressure sensor may have higher priority than a temperature sensor. In response to the electrical detection of the disconnection, the host processor may be configured to disable power provision to the data transfer cable from the at least one sensor-agnostic DI port. The encrypted AU/ID information may include identification information for a manufacturer of the sensor. The host processor may be configured to authenticate the sensor based on the encrypted AU/ID information, enable power provision to the data transfer cable via the at least one power contact based on the authentication, send a request for sensor data streams from the at least one sensor-agnostic DI port via the at least two communication contacts, and receive sensor data streams in a sensor-agnostic data format according to a protocol of the at least one sensor-agnostic DI port. The cable processor may be configured to receive power from the medical device via the at least one sensor-agnostic DI port, receive the request for sensor data streams via communication signals transmitted by the cable isolation device, and execute software stored in the cable memory to format sensor data in the sensor-agnostic data format according to the protocol of the at least one sensor-agnostic DI port, and send the sensor data streams in the sensor-agnostic data format to the host processor via the communication signals transmitted by the cable isolation device. The host processor may be configured to send a request for sensor identification information from the at least one sensor-agnostic DI port via the at least two communication contacts, receive unencrypted sensor identification information in response to the request, compare the encrypted AU/ID information with the unencrypted sensor identification information, and if the encrypted AU/ID information corresponds to the unencrypted sensor identification information, then request and receive the sensor data streams, else disable power provision to the data transfer cable. The data transfer cable may include at least one illumination device configured to illuminate in a color based on a type of the sensor. The host processor may be configured to cause the at least one illumination device to illuminate in response to user input. The display may be a touch screen display and the host processor may be configured to cause the at least one illumination device to illuminate in response to a user touch at the at least one visual representation of the sensor data. The medical device may be a patient monitor/defibrillator.

An example of a patient monitoring and treatment system for providing defibrillation and capturing data from sensors for collection of medical data according to the disclosure includes a monitor/defibrillator that includes a first housing comprising at least one sensor hub connector, a first display coupled to the first housing, a first communications interface, and a first processor, memory, and associated circuitry communicatively coupled to the first communications interface and the first display and includes at least one sensor hub that includes a second housing comprising at least one mating mechanism configured to removably couple the at least one sensor hub to the at least one sensor hub connector, at least one data interface (DI) port coupled to the second housing and comprising a plurality of electrical contacts configured to enable data communications between at least one sensor and the at least one sensor hub, a second communications interface configured to communicatively couple to the first communications interface, and a second processor, memory, and associated circuitry communicatively coupled to the second communications interface that are configured to receive sensor data via the at least one DI port and send the sensor data to the monitor/defibrillator via the first and second communications interfaces and the first display is configured to provide a first visual representation of the sensor data.

Implementations of such a system may include one or more of the following features. The at least one sensor hub connector may be a receptacle disposed on an interior surface of the first housing to removably couple the at least one sensor hub to the monitor/defibrillator within the first housing. The at least one DI port may be accessible from an exterior surface of the first housing when the at least one sensor hub is coupled to the first housing. The first and second communications interfaces may be configured to communicate with one another via wired and/or wireless communicative couplings. The first and second communications interfaces may be configured to communicate with one another via a wired communicative coupling when the at least one sensor hub is coupled to the at least one sensor hub connector and via a wireless communicative coupling when the at least one sensor hub is uncoupled from the at least one sensor hub connector. The first and second communications interfaces may be configured to communicate with one another via wired couplings when the at least one sensor hub is coupled to the at least one sensor hub connector and when the at least one sensor hub is uncoupled from the at least one sensor hub connector. The second processor may be configured to process one or more predetermined and specific types of sensor data. The second processor may be configured to process pulse oximetry data and capnography data. The at least one sensor hub may include a pneumatic pump system for side-stream capnography. The second processor may be configured to process non-invasive blood pressure data. The at least one sensor hub may include a non-invasive blood pressure pneumatic pump system. The at least one DI port may be a sensor-agnostic DI port that includes a plurality of electrical contacts configured to enable power transfer to a sensor and data communications between the sensor and the monitor/defibrillator via a data transfer cable coupled to the sensor-agnostic DI port and the sensor. The plurality of electrical contacts may include at least (a) at least two communication contacts, (b) at least one power contact, and (c) at least one ground cable contact. The plurality of electrical contacts may include at least one connection detection contact for electrically detecting a connection and a disconnection between the data transfer cable and the sensor-agnostic DI port. The plurality of electrical contacts may include at least one authentication contact. The second processor may be configured to send an AU/ID request for the sensor via the at least one authentication contact, receive encrypted AU/ID information in response to the AU/ID request in an absence of power transmission to the data transfer cable from the sensor-agnostic DI port, authenticate the sensor based on the encrypted AU/ID information, and provide power to the data transfer cable via the at least one power contact based on the authentication. The encrypted AU/ID information may include identification information for a manufacturer of the sensor. The second processor may be configured to provide power to the data transfer cable via the at least one power contact, send a request for sensor data streams from the sensor-agnostic DI port via the at least two communication contacts, and receive sensor data streams in a sensor-agnostic data format according to a protocol of the sensor-agnostic DI port. The second processor may be configured to send a request for sensor information from the sensor-agnostic DI port via the at least two communication contacts, in response to the request, receive the sensor information including unencrypted AU/ID information, compare the encrypted AU/ID information with the unencrypted AU/ID information, and if the encrypted AU/ID information corresponds to the unencrypted AU/ID information, then request and receive the sensor data streams, else discontinue providing power to the data transfer cable. The sensor-agnostic DI port excludes an isolation device for limiting patient leakage current flow from the monitor/defibrillator to the sensor. The at least one sensor hub may include a second display configured to provide a second visual representation of the sensor data and a plurality of DI ports. The at least one sensor hub connector may be disposed on an exterior surface of the first housing. The at least one sensor hub connector may include a bracket and the at least one mating mechanism may include a contour on the at least one sensor hub configured to removably couple the at least one sensor hub to the bracket. The at least one sensor hub connector may include one or more first electrical contacts and the at least one mating mechanism may include one or more second electrical contacts. The monitor/defibrillator and the at least one sensor hub may be configured to electrically and/or communicatively couple via the one or more first and second electrical contacts when the at least one sensor hub is physically retained by the at least one sensor hub connector. The first housing may include one or more first electrical contacts and the second housing may include one or more second electrical contacts. The at least one sensor hub connector and the at least one mating mechanism may be configured to couple the monitor/defibrillator and the at least one sensor hub such that the one or more first and second electrical contacts provide electrical and/or communicative connectivity when the at least one sensor hub is physically retained in the at least one sensor hub connector. The at least one sensor hub may be configured to electrically couple to the monitor/defibrillator via a wired connection and to communicatively couple to the monitor/defibrillator via a wireless connection when the at least one sensor hub is physically retained in the at least one sensor hub connector. The at least one sensor hub may be configured to communicatively couple to the monitor/defibrillator via a wired cable or a wireless coupling when the at least one sensor hub is physically separated from the at least one sensor hub connector. The at least one sensor hub may be configured to communicatively couple to the monitor/defibrillator and/or to one or more remote computing devices. The at least one sensor hub may include at least one USB port. The at least one DI port may include a sensor-specific DI port. The at least one DI port may correspond to an ECG sensor. The at least one DI port may correspond to a pulse oximetry sensor. The at least one DI port may correspond to a capnography sensor. The at least one sensor hub may include a plurality of sensor-specific DI ports. The plurality of sensor-specific DI ports may correspond to one or more of a heart rate sensor, an invasive blood pressure sensor, a non-invasive blood pressure sensor, and a temperature sensor. The at least one DI port may correspond to a cardiopulmonary resuscitation (CPR) compression sensor. The at least one DI port may correspond to an airway flow sensor. The at least one sensor hub may include a user interface. The user interface may include a second display configured to provide a second visual representation of the sensor data. The second display may be configured to provide the second visual representation of one or more of a pulse oximetry waveform, a capnography waveform, and an ECG waveform. The second display may be configured to provide the second visual representation of one or more physiological parameters corresponding to one or more discrete numerical values. The one or more physiological parameters corresponding to one or more discrete numerical values may include one or more of blood pressure, heart rate, an instantaneous pulse oximetry value, and an instantaneous capnography value. The second display may be configured to provide one or more of chest compression data and airway flow sensor data as one or more of a waveform, a discrete numerical value, and a graphic indicator. The chest compression data may include one or more of a compression depth, a compression rate, a compression release indicator, a perfusion indicator, and a CPR timer. The user interface may include one or more of alarm controls and a power button. The user interface may include data entry controls. The user interface may be configured to capture one or more of audio input and tactile input. The user interface may be configured to provide one or more of audio output, visual output, and haptic output. The system may include a wired and/or wireless coupling port configured to couple the at least one sensor hub to a user input device. The user input device may include one of a mouse, a microphone, and a wireless remote control. The user input device may include a wearable computing device. The wearable computing device may be one or more of an earpiece, a watch, and glasses. The first and second communications interfaces may be configured to communicatively couple with one another via wired and/or wireless couplings. The monitor/defibrillator may be configured to receive sensor data for a patient from the at least one sensor hub and associate the received sensor data with sensor data received by the monitor/defibrillator for the patient. The at least one sensor hub may be configured to receive sensor data for a patient from the monitor/defibrillator and associate the received sensor data with sensor data received by the at least one sensor hub for the patient. The second communications interface may be configured to communicatively couple to a remote server via the first communications interface. The second communications interface may be configured to communicatively couple to a mobile computing device via the first communications interface. The mobile computing device may include one or more of a smart phone and a computer tablet. The second communications interface may be configured to communicatively couple with one or more of a remote server, a mobile computing device, and a wearable computing device in an absence of an existing communicative coupling with the first communications interface. The second communications interface may be configured to send one or more of a case file, sensor data, device readiness data, and device status data to a communicatively coupled device. The second communications interface may be configured to receive one or more of sensor data, software updates, settings updates, and protocol updates from a communicatively coupled device. The second communications interface may be configured to communicatively couple to one or more computing devices via one or more of a long-range wired and/or wireless connection and a short range wired and/or wireless connection. The one or more computing devices may include one or more of a mobile computing device, a wearable computing device, a tablet, a smartphone, a watch, a heads-up display, a laptop computer, or combinations thereof. The short range wireless connection may include at least one of a Bluetooth®, a Zigbee®, and a near-field communication device connection. The long-range wired and/or wireless connection may include one or more of a cellular communications network and a computer network. The second communications interface may be configured to communicatively couple to one or more medical devices via one or more of a long-range wired and/or wireless connection and a short range wired and/or wireless connection. The one or more medical devices may include one or more of a compression monitor, an airway flow sensor, a bag valve mask, and first aid kit. The monitor/defibrillator may be a first monitor/defibrillator and the one or more medical devices may include a second monitor/defibrillator. The first communications interface and the second communications interface may be configured to communicatively couple in response to an authentication of the at least one sensor hub. The at least one sensor hub may be configured to communicatively couple with only one monitor/defibrillator during treatment of a patient. The authentication may include an information exchange to verify that the monitor/defibrillator and the at least one sensor hub are associated with a same patient. The sensor hub may include at least two DI ports configured to enable communications between at least two sensors and the sensor hub. The at least two DI ports may include SS-DI ports, SA-DI ports, or a combination thereof. The at least one sensor hub may be a respiratory distress hub.

An example of a patient monitoring and treatment system for providing defibrillation and capturing data from sensors for collection of medical data includes a monitor/defibrillator including a first housing comprising at least one sensor hub connector, a first display coupled to the first housing, a first communications interface, and a first processor, memory, and associated circuitry communicatively coupled to the first communications interface and the first display; and at least one sensor hub comprising a respiratory distress (RD) hub, the RD hub including a second housing comprising at least one mating mechanism configured to removably couple the at least one RD hub to the at least one sensor hub connector, at least one data interface (DI) port coupled to the second housing and comprising a plurality of electrical contacts configured to enable data communications between at least one sensor and the at least one RD hub, a second communications interface configured to communicatively couple to the first communications interface, and a second processor, memory, and associated circuitry communicatively coupled to the second communications interface and configured to: receive sensor data via the at least one DI port, and send the sensor data to the monitor/defibrillator via the first and second communications interfaces, wherein the first display is configured to provide a first visual representation of the sensor data.

Implementations of such a system may include one or more of the following features. The at least one sensor hub connector may include a receptacle disposed on an interior surface of the first housing to removably couple the at least one RD hub to the monitor/defibrillator within the first housing. The at least one DI port may be accessible from an exterior surface of the first housing when the at least one RD hub may be coupled to the first housing. The first and second communications interfaces may be configured to communicate with one another via wired and/or wireless communicative couplings. The first and second communications interfaces may be configured to communicate with one another via a wired communicative coupling when the at least one RD hub is coupled to the at least one RD hub connector and via the wireless communicative coupling when the at least one RD hub is uncoupled from the at least one RD hub connector. The first and second communications interfaces may be configured to communicate with one another via wired couplings when the at least one RD hub is coupled to the at least one sensor hub connector and when the at least one RD hub is uncoupled from the at least one sensor hub connector. The second processor may be configured to process one or more pre-determined and specific types of sensor data. The second processor may be configured to process one or more of pulse oximetry data, capnography data, pneumotachometer data, flow rate data, tidal volume data, minute ventilation data, respiratory mechanics data, spirometry data, FVC data, FEV1 data, and PEF data. The at least one RD hub may include a mechanical ventilation apparatus. The at least one DI port may be a sensor-agnostic DI port comprising a plurality of electrical contacts configured to enable power transfer to a sensor and data communications between the sensor and the monitor/defibrillator via a data transfer cable coupled to the sensor-agnostic DI port and the sensor. The plurality of electrical contacts may include at least (a) at least two communication contacts, (b) at least one power contact, and (c) at least one ground cable contact. The plurality of electrical contacts may include at least one connection detection contact for electrically detecting a connection and a disconnection between the data transfer cable and the sensor-agnostic DI port. The plurality of electrical contacts may include at least one authentication contact, and the second processor may be configured to send an AU/ID request for the sensor via the at least one authentication contact, receive encrypted AU/ID information in response to the AU/ID request in an absence of power transmission to the data transfer cable from the sensor-agnostic DI port, authenticate the sensor based on the encrypted AU/ID information, and provide power to the data transfer cable via the at least one power contact based on the authentication. The encrypted AU/ID information may include identification information for a manufacturer of the sensor. The second processor may be configured to provide power to the data transfer cable via the at least one power contact, send a request for sensor data streams from the sensor-agnostic DI port via the at least two communication contacts, and receive the sensor data streams in a sensor-agnostic data format according to a protocol of the sensor-agnostic DI port. The second processor may be configured to send a request for sensor information from the sensor-agnostic DI port via the at least two communication contacts, in response to the request, receive the sensor information comprising unencrypted AU/ID information, compare the encrypted AU/ID information with the unencrypted AU/ID information, and if the encrypted AU/ID information corresponds to the unencrypted AU/ID information, then request and receive the sensor data streams, else discontinue providing power to the data transfer cable. The sensor-agnostic DI port may exclude a host isolation device for limiting patient leakage current flow from the monitor/defibrillator to the sensor. The at least one RD hub may include a second display configured to provide a second visual representation of the sensor data and a plurality of DI ports. The at least one sensor hub connector may be disposed on an exterior surface of the first housing. The at least one sensor hub connector may include a bracket and the at least one mating mechanism may include a contour on the at least one RD hub configured to removably couple the at least one RD hub to the bracket. The at least one RD hub connector may include one or more first electrical contacts and the at least one mating mechanism may include one or more second electrical contacts, and wherein the monitor/defibrillator and the at least one RD hub may be configured to electrically and/or communicatively couple via the one or more first and second electrical contacts when the at least one RD hub is physically retained by the at least one RD hub connector. The first housing may include one or more first electrical contacts and the second housing may include one or more second electrical contacts, and wherein the at least one sensor hub connector and the at least one mating mechanism may be configured to couple the monitor/defibrillator and the at least one RD hub such that the one or more first and second electrical contacts provide electrical and/or communicative connectivity when the at least one RD hub is physically retained in the at least one sensor hub connector. The at least one RD hub may be configured to electrically couple to the monitor/defibrillator via a wired connection and to communicatively couple to the monitor/defibrillator via a wireless connection when the at least one RD hub is physically retained in the at least one sensor hub connector. The at least one RD hub may be configured to communicatively couple to the monitor/defibrillator via a wired cable or a wireless coupling when the at least one RD hub is physically separated from the at least one sensor hub connector. The at least one RD hub may be configured to communicatively couple to the monitor/defibrillator and/or to one or more remote computing devices. The at least one RD hub may include at least one USB port. The at least one DI port may include a sensor-specific DI port. The at least one DI port may correspond to one or more of a lung mechanics sensor, a spirometry sensor, an airway pressure sensor, a pulse oximetry sensor, and a capnography sensor. The at least one RD hub may include a plurality of sensor-specific DI ports. The plurality of sensor-specific DI ports correspond to one or more of an ECG sensor, a pulse oximetry sensor, a capnography sensor, heart rate sensor, an invasive blood pressure sensor, a non-invasive blood pressure sensor, a temperature sensor, a lung mechanics sensor, a spirometry sensor, an airway pressure sensor, a pulse oximetry sensor, and a capnography sensor. The at least one DI port corresponds to a cardiopulmonary resuscitation (CPR) compression sensor. The at least one RD hub may include a user interface. The user interface may include a second display configured to provide a second visual representation of the sensor data. The second display may be configured to provide the second visual representation of one or more of a pulse oximetry waveform, a capnography waveform, and an ECG waveform. The second display may be configured to provide the second visual representation of one or more physiological parameters corresponding to one or more discrete numerical values. The one or more physiological parameters may correspond to one or more discrete numerical values may include one or more of blood pressure, heart rate, an instantaneous pulse oximetry value, and an instantaneous capnography value. The second display may be configured to provide one or more of chest compression data and airway flow sensor data as one or more of a waveform, a discrete numerical value, and a graphic indicator. The second display may be configured to provide ventilation settings, ventilation parameters, and respiratory physiological parameters. The user interface may include one or more of alarm controls and a power button. The user interface may include data entry controls. The user interface may be configured to capture one or more of audio input and tactile input. The user interface may be configured to provide one or more of audio output, visual output, and haptic output. The system may include wired and/or wireless coupling port configured to couple the at least one RD hub to a user input device. The user input device may include one of a mouse, a microphone, and a wireless remote control. The user input device may include a wearable computing device. The wearable computing device may include one or more of an earpiece, a watch, and glasses. The first and second communications interfaces may be configured to communicatively couple with one another via wired and/or wireless couplings. The monitor/defibrillator may be configured to receive sensor data for a patient from the at least one RD hub and associate the received sensor data with sensor data received by the monitor/defibrillator for the patient. The at least one RD hub may be configured to receive sensor data for a patient from the monitor/defibrillator and associate the received sensor data with sensor data received by the at least one RD hub for the patient. The second communications interface may be configured to communicatively couple to a remote server via the first communications interface. The second communications interface may be configured to communicatively couple to a mobile computing device via the first communications interface, the mobile computing device including one or more of a smart phone and a computer tablet. The second communications interface may be configured to communicatively couple with one or more of a remote server, a mobile computing device, and a wearable computing device in an absence of an existing communicative coupling with the first communications interface. The second communications interface may be configured to send one or more of a case file, sensor data, device readiness data, and device status data to a communicatively coupled device. The second communications interface may be configured to receive one or more of sensor data, software updates, settings updates, and protocol updates from a communicatively coupled device. The second communications interface may be configured to communicatively couple to one or more computing devices via one or more of a long-range wired and/or wireless connection and a short range wired and/or wireless connection. The one or more computing devices may include one or more of a mobile computing device, a wearable computing device, a tablet, a smartphone, a watch, a heads-up display, a laptop computer, or combinations thereof. The short range wireless connection may include at least one of a Bluetooth®, a Zigbee®, and a near-field communication device connection. The long-range wired and/or wireless connection may include one or more of a cellular communications network and a computer network. The second communications interface may be configured to communicatively couple to one or more medical devices via one or more of a long-range wired and/or wireless connection and a short range wired and/or wireless connection. The one or more medical devices may include one or more of a compression monitor, an airway flow sensor, a bag valve mask, and first aid kit. The monitor/defibrillator may be a first monitor/defibrillator and the one or more medical devices may include a second monitor/defibrillator. The first communications interface and the second communications interface may be configured to communicatively couple in response to an authentication of the at least one RD hub. The at least one RD hub may be configured to communicatively couple with only one monitor/defibrillator during treatment of a patient. The authentication may include an information exchange to verify that the monitor/defibrillator and the at least one RD hub may be associated with a same patient. The system may include at least two DI ports configured to enable communications between at least two sensors and the at least one RD hub. The at least two DI ports may include SS-DI ports, SA-DI ports, or a combination thereof. The RD hub may include a mechanical ventilation apparatus. The mechanical ventilation apparatus may include a gas mover, an expiratory circuit, an inspiratory circuit, and one or more respiratory sensors. The RD hub may be configured to couple to an oxygen source and a gas delivery device. The RD hub may include a controller configured to provide closed loop control of one or more respiratory parameters during mechanical ventilation of a patient.

Other capabilities may be provided and not every implementation according to the disclosure must provide any, let alone all, of the capabilities discussed. Further, it may be possible for an effect noted above to be achieved by means other than that noted and a noted item/technique may not necessarily yield the noted effect.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

DETAILED DESCRIPTION

Figure 1:
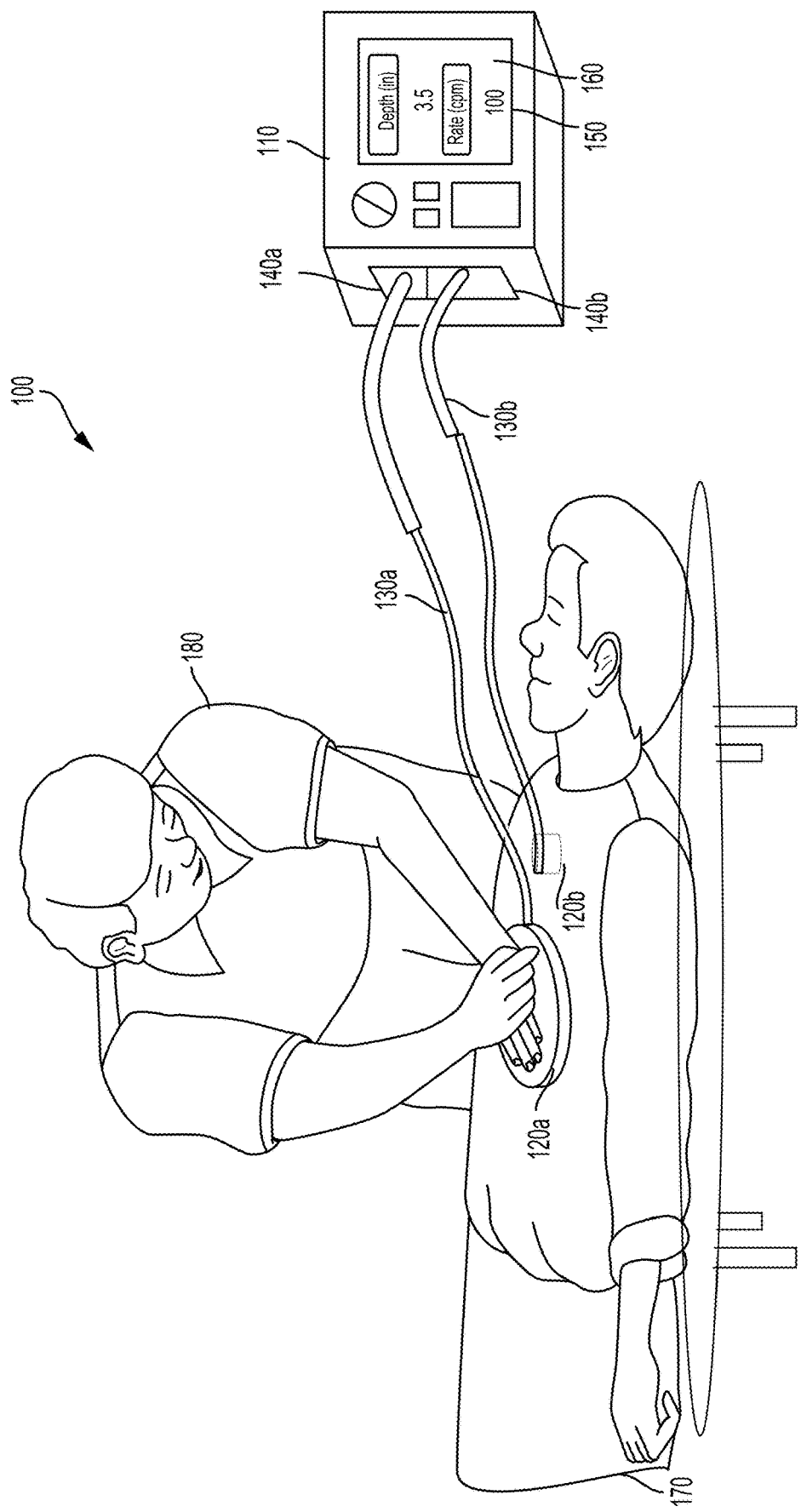
FIG. 1 shows an example of a system of a medical device, data transfer cables, and sensors for capturing data associated with a patient.

During a medical event, a medical device may be used by a caregiver (e.g., a first responder, a paramedic, a physician, a nurse, a rescue worker, etc.) to provide medical therapy to a patient and/or may be used to monitor the patient. The medical device may be, for example, a patient monitor, a therapeutic medical device (e.g., a defibrillator, an automated compression device, a ventilator, etc.), a therapeutic medical device/patient monitor, or a modular therapeutic medical device/patient monitor. These types of medical devices are examples only and other types and combinations of medical devices are within the scope of the disclosure.

The medical device may be configured to couple to one or more sensors. The sensors may include one or more combined therapy delivery/sensing components such as defibrillation electrodes configured to sense and monitor a patient's electrocardiogram (ECG) and to deliver electrotherapy. The medical device may collect data via the one or more sensors. The data may include physiological sensor data and/or medical or resuscitative treatment data. The physiological sensor data may include, for example, invasive blood pressure (IBP), non-invasive blood pressure (NIBP), electrocardiogram (ECG) data, pulse oximetry data (SpO2), capnography data, methemoglobin (SpMet), hemoglobin, body temperature, cerebral oxygen saturation (rSO2), heart rate, and/or other vital signs. The physiological data may also include imaging data such as, for example, laryngoscopy and/or ultrasound. The medical or resuscitative treatment data may include, for example, CPR performance data derived from measurements obtained from a chest compression sensor (e.g., compression depth, compression rate, chest release, perfusion performance, etc.) and/or ventilation data from measurements obtained from an airway flow sensor (e.g., ventilation tidal volume, ventilation rate, ventilation minute volume, ventilation performance, etc.). These types of data are examples only and not limiting of the disclosure and are discussed in further detail below.

The medical device and the one or more sensors may couple to one another via a data transfer cable. To enable these wired couplings, the medical device may include one or more data interface (DI) ports. Each data interface port may be configured to removably couple to a data transfer cable, the data transfer cable coupled, in turn, to a sensor.

The DI port may be a sensor-specific DI port. For example, in various implementations, the sensor-specific DI port may be configured with a cable contact count and wiring assignments, voltage(s), and/or processor configuration for signal processing protocol compatible with one type of sensor but incompatible with another type of sensor. For example, the sensor-specific DI port may be compatible with an IBP accessory (e.g., a sensor/data transfer cable combination for IBP) but may not be compatible with a capnography accessory (e.g., sensor/data transfer cable combination for sensing exhaled gas flow such as carbon dioxide). As an incompatible accessory, the capnography accessory may not mate physically with the IBP specific port and/or may not be electrically compatible and/or may provide sensing data to the IBP specific port that the IBP specific port cannot process due to differences in data protocols for different sensor data types.

The sensor-specific DI port presents a usability issue for medical professionals and particularly for emergency care providers. The sensor-specific DI port requires that each sensor cable be connected with a specific port on the medical device. An emergency care situation is typically chaotic with a significant urgency in terms of time. This chaos and urgency are due in part to the inherent nature of an emergency medical event like cardiac arrest, a drug overdose, a car accident injury, or a gunshot injury. Additionally, the scene of an emergency event may not be a calm and orderly doctor's office but rather an ambulance, an emergency room, a disrupted workplace, home, or school, a highway, a public sidewalk, or even a battlefield. Trying to connect multiple sensor cables to specific ports on a medical device in these situations presents usability challenges beyond that of a non-medical device used in a calmer and less time-critical situation.

A sensor-agnostic DI port solves at least this usability problem for the medical device. The sensor-agnostic DI port may be configured to capture a variety of sensor data types, each provided via a data transfer cable configured to provide the sensor data in a format compatible with the sensor-agnostic DI port. Thus, the caregiver can attach any sensor cable to any available sensor-agnostic DI port on the medical device with a possibly life-saving reduction of time and confusion.

The sensor-specific DI port also presents an adaptability issue for the medical device manufacturer and for users. The adaptability issue results from the hardware changes necessary to accommodate new or changed sensors with sensor-specific DI ports. In order to accommodate sensor changes, a manufacturer of the medical device may have to change one or more of the cable contact count and wiring assignments, voltage(s), and/or a processor configuration for a signal processing protocol for the sensor-specific DI ports. Additionally, the sensor-specific DI port may include patient leakage current isolation tailored to the power requirements of the particular sensor. For example, the operational power requirements for an airway flow sensor may be greater than that for an IBP sensor. The airway flow sensor may require 0.5 Watts whereas the IBP sensor may only require 0.25 Watts. As a result of these differences in operational power requirements, the patient leakage current isolation hardware on these two ports will be different. Thus, to accommodate new or different sensors, the manufacturer also has to change the patient leakage current isolation hardware for the sensor-specific DI ports. As a result of these changes, the user has to make the medical equipment available for hardware modifications and/or, more likely, purchase new equipment to accommodate sensor changes.

The sensor-agnostic DI port may couple with a data transfer cable compatible with this type of port. The data transfer cable may include hardware compatible with the cable contact count and wiring assignments and voltage(s) of the sensor-agnostic DI port. Furthermore, the data transfer cable may include a processor, stored software, and patient leakage current isolation that provide the sensor data in an agnostic format, throttle agnostic power delivery according to the needs of the sensor, and tailor the patient leakage current isolation to the specific sensor power requirements.

In addition to the usability advantage of the sensor-agnostic DI port, the sensor-agnostic DI port combined with the compatible data transfer cable may provide an adaptability advantage. The compatible data transfer cable is a data transfer cable mechanically, electrically, and programmatically compatible with the sensor-agnostic DI port rather than a sensor-specific DI port. The adaptability advantage is an ability of the medical device with the sensor-agnostic DI port to accommodate new sensors and/or sensor changes with software updates without hardware changes. With the sensor-agnostic DI port, the cable contact count and wiring assignments, voltage(s), and/or processor configuration for signal processing protocols are compatible with any type of sensor. Therefore, to accommodate a new sensor, the manufacturer can update the software on the medical device to accommodate the new sensor and provide the sensor with a compatible data transfer cable. The user of the medical device may add or purchase an additional sensor/cable combination without the need to replace or modify the medical device. The software update may occur via a remote connection and/or via a connection with the medical device. For example, when the data transfer cable is connected to the medical device for the first time, the data transfer cable and the medical device may communicate to download software to the data transfer cable that provides data formats that enable the medical device to read and process data from the data transfer cable. Additionally, each time the data transfer cable is connected to the medical device, the data transfer cable and the medical device may communicate to provide the data transfer cable with any medical device software updates and/or to provide the medical device with any data transfer cable formatting updates. Thus communications between the data transfer cable and the medical device may ensure data and software compatibility between the data transfer cable and the medical device with each connection.

A further advantage imparted by sensor-agnostic DI port combined with the compatible data transfer cable is a reduction in weight, volume, and signal noise for the medical device. This reduction stems from a removal of a patient leakage current isolation from the sensor-agnostic DI port to the data transfer cable.

As discussed above, a medical device, such as a patient monitor or patient monitor/defibrillator, would include an attachment of multiple sensors for effective patient care. Each sensor connection via a wired cable requires a DI port with patient leakage current isolation. This applies to a sensor-specific DI port and to a sensor-agnostic DI port. Each patient leakage current isolation included in the medical device increases the weight and volume of the medical device and contributes to signal noise. The higher the power rating of a sensor, the more the weight, volume, and signal noise increase. The weight increase derives from the isolation circuitry and other physical isolation components and physical noise reduction components. In some cases, signal noise reduction requires a physical noise shield (e.g., a surrounding conductive layer). The volume increase derives from the space required for the isolation hardware and from a physical separation distance between ports necessary for electrical isolation and noise reduction. The signal noise increase derives from the power transmitted through the isolation circuitry to power the sensor. Higher power transmission results in more signal noise. Accordingly, higher power transmission requires more physical noise reduction components and physical separation thereby contributing to an increase in weight and volume of the medical device.

For the sensor-agnostic DI ports, if the patient leakage current isolation is included in the port, then every port isolates and provides noise reduction according to the port(s) with the maximum power requirement. For example, the medical device may provide three DI ports to enable connection to an IBP sensor, a temperature sensor, and an airway flow sensor. The IBP and temperature sensor may have an operational power requirement of at least an amount between 0.1 Watts and 0.5 Watts (e.g., about 0.25 Watts) and the airway flow sensor may have an operational power requirement of at least an amount between 0.2 Watts and 1.0 Watt (e.g., about 0.5 Watts). In various embodiments, the airway flow sensor may have an operational power requirement that is greater than that of the IBP and/or temperature sensor. If the patient leakage current isolation is provided at the sensor-agnostic DI port, then each port must provide patient leakage current isolation based on the operational power requirement of the airway flow sensor.

In order to reduce the weight and volume of the medical device, the data transfer cable may include the patient leakage current isolation and the sensor-agnostic DI port may not include (i.e., may exclude) the patient leakage current isolation. The medical device may provide the same power to each sensor-agnostic DI port and the isolation circuitry in the compatible data transfer cable may control power transmission based on the specific sensor attached to the cable. In the example above, the IBP sensor cable may isolate to a power rating of between 0.1 W and 0.5 W (e.g., 0.25 W power rating) irrespective of the power rating (e.g., 0.5 Watt rating) of the airway flow sensor. Furthermore, the physical and electrical configuration of the isolation with regard to noise is also tailored to the specific sensor while retaining a sensor-agnostic configuration for the DI port. With isolation provided in the cable, the sensor-agnostic DI ports at the medical device do not require the isolation hardware, a physical separation, or noise reduction for the isolation hardware. Therefore, sensor-agnostic DI port combined with the compatible data transfer cable reduces the overall weight and volume of the medical device without a reduction in signal quality or leakage current protection and with an increase in the overall number of available ports.

Exclusion of the patient leakage current isolation may reduce the weight and volume of the medical device by 5-15%. Depending on the medical device, this can be a weight savings of at least 0.5 kg. An aggregate weight savings with multiple sensor-agnostic DI ports may be approximately 0.1-0.6 kilograms, depending on the number ports. An emergency caregiver may need to carry 11-18 kg of gear exclusive of any protective garments which may also be heavy particularly for firefighters. In some situations, these emergency caregivers are climbing multiple flights of stairs and/or running over rough terrain to reach a victim. Therefore, weight reduction on portable medical devices is critical. An analogous situation is in backpacking where hikers seek to reduce weight on every item of backpacking gear in order to reduce the overall load.

Another advantage of locating patient leakage current isolation in the data transfer cable compatible with the sensor-agnostic DI port is an ability to electrically separate an authentication circuit from the cable processor. The medical device may authenticate the data transfer cable and the sensor prior to applying power to the sensor-agnostic DI port that enables sensor data communications.

In an implementation, the medical device may include one or more removable sensor hubs that provide one or more DI ports. These DI ports may be sensor-agnostic, sensor-specific, or a combination thereof. The removable sensor hub may also include hardware and/or hardware controls for a particular sensor or combination of sensors. For example, the sensor hub may provide pneumatic controls and a pump system for NIBP and/or capnography. The one or more removable sensor hubs may removably couple to the medical device within a medical device housing or to an exterior of the medical device housing. The sensor hub may capture sensor data when physically coupled and when physically uncoupled from the medical device. The removable sensor hub may communicatively couple to the medical device via a wired or a wireless connection.

The sensor hub may provide several advantages. For example, instead of inextricably including sensor-specific hardware in the medical device, the sensor hub may include this hardware. This provides an advantage that a manufacturer may customize the medical device to the sensor needs of a customer and a customer may tailor the medical device to desired sensors. Also, updates and replacements of such hardware and associated software may involve just the sensor hub rather than the medical device as a whole. An additional advantage of the removable sensor hub is that the sensor hub may remain coupled to a patient while physically uncoupled from the medical device. In this implementation, the removable sensor hub may communicate with the medical device wirelessly which provides the advantage of eliminated cable connections between the patient and the medical device for some period of time. Alternatively, the removable sensor hub may communicate with the medical device via a single cable tether between the medical device and the sensor hub. This may provide the advantage of reducing the number of cable connections between the patient and the medical device to one (rather than the multiple cables needed for multiple sensors). Patients are often transferred during care between medical care locations and personnel. For example, as a patient may be transported from a scene of an emergency, to an ambulance to a hospital emergency room, to an operating room, to an intensive care unit, to a recovery room, to a rehabilitation center, etc. The sensor hub enables continuous patient monitoring during all of these physical transitions as the sensor hub can be detached and reattached to larger pieces of medical monitoring equipment without removing the sensors from the patient, without moving the larger pieces of equipment, and with a reduction in cable connections to one or zero. Otherwise, without such enhancements, it may be much more cumbersome for caregivers to have to manage cable connections with the larger, heavier medical device to the patient.

Additionally, a caregiver can place the sensor hub on a gurney or other supportive item near the patient and in a location easily viewable and accessible for the caregiver. In an implementation, the sensor hub may be sufficiently lightweight to place on the patient without any negative impact on patient care and/or resuscitation. Locating the sensor hub as close to the patient as possible, including possibly on the patient, may enable the caregiver to provide care and view a data display on the sensor hub and/or connect or disconnect sensors with little to no interruption in the time they have eyes on the patient, without having to turn attention away from the patient. The proximate location may also keep the sensor hub within a sterile surgical zone. These locations may not be options for a larger item of medical equipment. However, the medical advantages of the larger equipment in terms of data processing, analysis, storage, and display are not lost with use of the sensor hub as it can be communicatively and physically coupled to the larger equipment.

Referring to FIG. 1, an example of a system of a medical device, data transfer cables, and sensors for capturing data associated with a patient is shown. The system 100 includes at least one medical device 110, sensors 120*a* and 120*b*, and data transfer cables 130*a* and 130*b*. Each data transfer cable 130*a* and 130*b* couples a respective sensor 120*a* or 120*b* to the medical device 110. In this example, the sensor 120*a* is a medical or resuscitative treatment sensor, for example, a chest compression sensor and the sensor 120*b* is a physiological sensor. Claimed subject matter is not limited to a particular type or category of sensor. In various implementations, the sensor 120*b* may be one or more of an invasive blood pressure (IBP) sensor, a non-invasive blood pressure (NIBP) sensor, an electrocardiogram (ECG) sensor, a pulse oximetry (SpO2) sensor, a capnography sensor, a methemoglobin (SpMet) sensor, a hemoglobin sensor, a body temperature sensor, a cerebral oxygen saturation (rSO2) sensor, a heart rate sensor, spirometry sensor, pneumotachometer, airway pressure sensor, airway flow sensor, and/or other physiologic sensor. In various implementations, the sensor 120*a* and/or 120*b* may be an imaging sensor for laryngoscopy and/or ultrasound. In various implementations, the sensor 120*a* and/or 120*b* may be an imaging sensor for laryngoscopy and/or ultrasound. In various implementations, the sensor 120*a* may be a chest compression sensor or an airway flow sensor. The data transfer cables 130*a* and 130*b* may each connect to a respective DI port 140*a* and 140*b*. One or more of the DI ports 140*a* and 140*b* may be a sensor-agnostic DI (SA-DI) port or a sensor-specific DI (SS-DI) port. The corresponding data transfer cable 130*a* or 130*b* may be a data transfer cable compatible with the SA-DI port or the SS-DI port. Although one medical device, two sensors, two DI ports, and two data transfer cables are shown in FIG. 1, in various implementations, the system 100 may include one or more medical devices, one or more sensors, and one or more data transfer cables.

The medical device 110 may provide therapy to and/or monitor the patient 170 and/or monitor treatment metrics for treatment provided by the caregiver 180. The medical device 110 may include a user interface 160 on a display 150. The user interface 160 may provide one or more of medical or resuscitation treatment data and physiological data from the sensor 120*a* and/or 120*b*. The medical device 110 may be, for example, a patient monitor, a therapeutic medical device (e.g., a defibrillator, an automated compression device, a ventilator, etc.), a therapeutic medical device/patient monitor, or a modular therapeutic medical device/patient monitor. The medical device 110 (or medical apparatus 110) may be provided as one physical device (e.g., a single housing) or may be provided as multiple physical devices (e.g., modular physical devices with two or more separate housings) configured to communicatively and/or operatively couple with one another. Although shown as one caregiver, in FIG. 1, the caregiver 180 may represent multiple caregivers (e.g., a care team) associated with the patient 170.

Figure 2A:
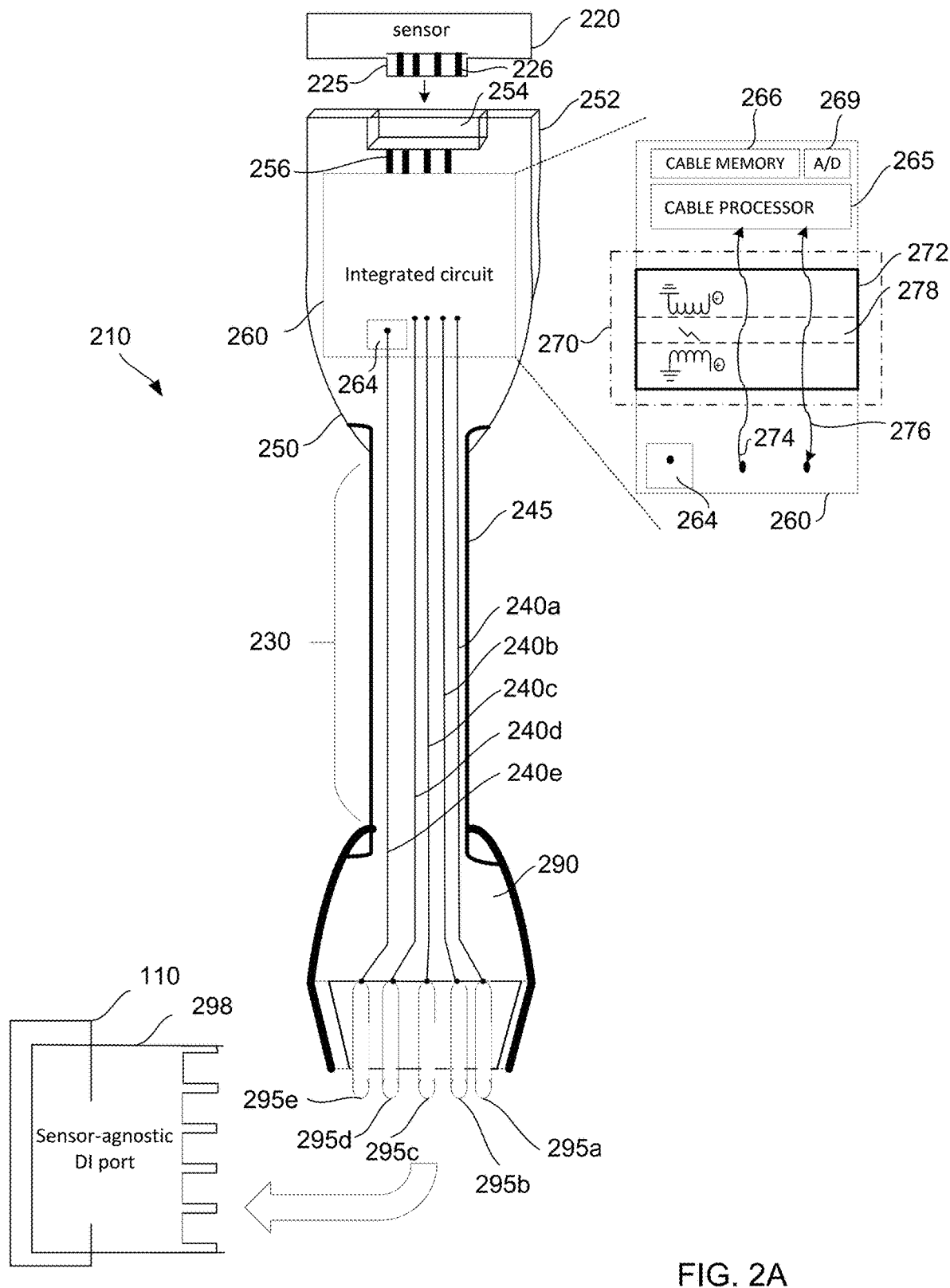
FIG. 2A is an example of data transfer cable compatible with a sensor-agnostic data interface port for transferring sensor data to a medical device.

Referring to FIG. 2A with further reference to FIG. 1, an example of a data transfer cable compatible with a sensor-agnostic data interface port for transferring sensor data to a medical device is shown. The data transfer cable 210 (e.g. the data transfer cable 130*a* and/or 130*b*) is configured to provide at least power transmission and data communications between a sensor 220 (e.g., the sensor 120*a* and/or 120*b*) for collecting sensor data and a sensor-agnostic data interface (DI) port 298 (e.g., the DI port 140*a* and/or 140*b*) associated with a medical device 110.

The data transfer cable 210 compatible with the SA-DI port 298 includes a flexible cable 230 constituting conductive wires (e.g., wires 240*a*, 240*b*, 240*c*, and 240*d*) disposed within a continuous insulative sheath 245. The conductive wires may include single strands and/or multi-strands of one or more conductive materials. The number of wires shown in FIG. 2A is an example only and not limiting of the disclosure. The cable 230 may be fixedly fastened to a first electromechanical connector 250 at a first end of the cable 230 and to a second electromechanical connector 290 at a second end of the cable 230.

The first electromechanical connector 250 may include a housing 252 and an electrical mating 254 (e.g., a first electrical mating) disposed within the housing 252 at an open end of the housing distal from the cable 230. In other words, the cable 230 connects to the housing at a first end of the housing and the electrical mating 254 for the sensor is disposed in a second and different end of the housing. The electrical mating 254 is configured to detachably couple to the sensor 220 (e.g., to an electrical connector 225 associated with the sensor 220). The electrical mating 254 provides electrical coupling between one or more contacts 226 associated with the sensor and one or more contacts 256 associated with the data transfer cable 210. The combination of the electrical mating 254 and the electrical connector 225 may be, for example, a pin/socket combination, a plug/jack combination, a card edge/spring contact combination, etc.

The first electromechanical connector 250 also includes data interface circuitry 260 disposed within the housing 252. FIG. 2A schematically illustrates the data interface circuitry 260 in the first electromechanical connector 250 and also illustrates components of the data interface circuitry 260 as an inset box with a blown-up view of the data interface circuitry 260. The data interface circuitry is electrically coupled to the electrical mating 254 by one or more electrical contacts 256 and is electrically coupled to the conductive wires (e.g., wires 240a, 240b, 240c, and 240d) of the cable 230. The data interface circuitry 260 includes a cable processor 265, a cable memory 266, and cable patient leakage current isolation 270. In an implementation, the data interface circuitry 260 includes an analog-to-digital (A/D) converter circuit 269 configured to convert analog signals from the sensor 220 to digital signals for the cable processor 265. The A/D converter is shown separately from the cable processor 265 for clarity but may be integrated into the cable processor 265.

Figure 2B:
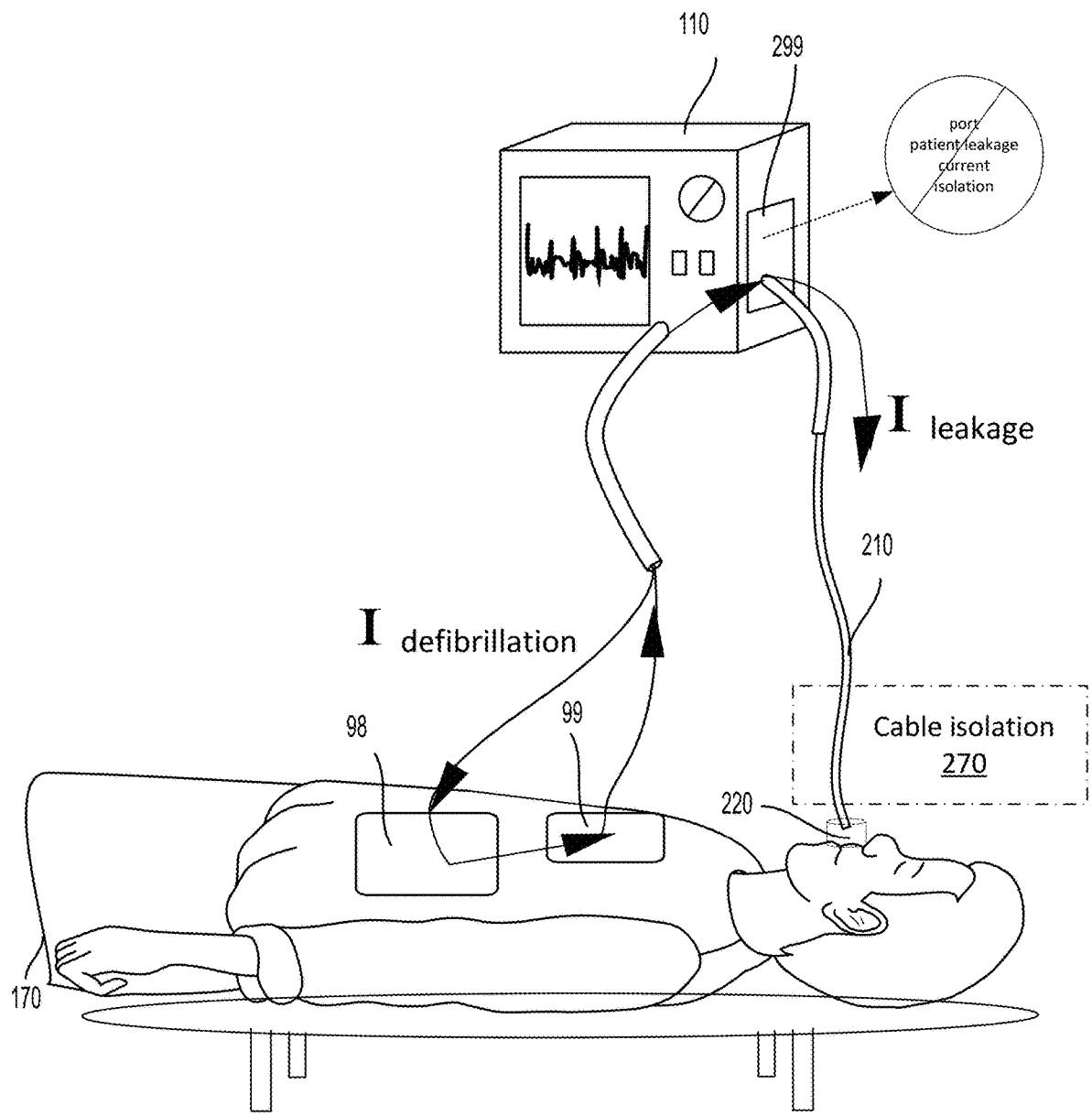
FIG. 2B is a schematic illustration of an example of a flow path for patient leakage current.

The cable patient leakage current isolation 270 comprises an isolation device 270 and/or circuitry and other hardware and/or physical components configured to limit patient leakage current flow from the medical device 110 to the patient via the sensor 220. Particularly for high voltage electrotherapy, leakage current isolation can be beneficial for safety reasons. Referring to FIG. 2B, a schematic illustration of an example of a flow path for patient leakage current is shown. In this illustrative example, the medical device 110 is a defibrillator and the patient 170 is coupled to defibrillation electrodes 98 and 99. The patient 170 is also coupled to a sensor 220 which, in turn, is coupled to the medical device 110 by the data transfer cable 210. Defibrillation current (I defibrillation) follows a current path from the medical device 110 to the defibrillation electrode 98, through the patient 170 to the electrode 99, and then back to the medical device 110. There is a potential current path between this defibrillation circuit and the data transfer cable 210, for example, via stray capacitance between the medical device 110, the patient 170 and the sensor 220, by which a patient leakage current ($I_{leakage}$) may reach the patient 170 via the sensor 220. However, the isolation 270 in the data transfer cable 210 is configured to prevent any patient leakage current from reaching the sensor 220 and the patient 170, thus, providing a protective layer of safety built into the cable. In certain embodiments, the SA-DI port 298 does not include (i.e., excludes) a patient leakage current isolation circuit as illustrated schematically in FIG. 2B.

Returning to FIG. 2A, the isolation device 270 and/or circuitry may include an isolation barrier device, for example a double capacitive isolation barrier device, a digital isolator device, an optical isolator device, etc. The isolation device 270 is configured to transmit power signals 274 and communication signals 276 across an isolation barrier 278. These devices are examples only and not limiting of the disclosure. The hardware and/or physical components may include without limitation conductive and insulative layers and/or coatings coupled to and/or surrounding the isolation device 270 and/or circuitry.

The isolation device 270 is configured to transmit power 274 uni-directionally across an isolation barrier 278 towards the cable processor 265. When the data transfer cable 210 is coupled to the medical device 110 via the SA-DI port 298, the medical device 110 may be the sensor power source and may provide power 274 to the cable processor 265 and the sensor 220 via the port 298 and the data transfer cable 210. For example, the data transfer cable 210 may transmit power 274 via at least one conductive wire 240d with another wire 240c at ground. The isolation device 270 may transfer this power 274, transmitted by the data transfer cable 210 from the medical device 110, across the isolation barrier 278 in one direction to the cable processor 265 and the sensor 220. With this uni-directional power transfer, there is substantially limited or no transmission of power from the processor side of the isolation 270 towards the medical device 110. In an implementation, the isolation device 270 may transfer, or transmit, 0.1-1 Watts of power 274 across the isolation barrier 278. In an implementation, the isolation device 270 is configured to transmit an amount of power 274 across the isolation barrier 278 that is specific to the power requirements of the sensor 220. For example, an invasive blood pressure sensor may require approximately 0.2 Watts whereas a flow sensor may require approximately 0.5 Watts. Thus, the power transmission capability of the isolation device 270 is tailored to the power requirement of the sensor 220. As a result, the medical device 110 may be configured to apply power in an amount compatible with a variety of sensors to the SA-DI port 298.

The isolation device 270 is also configured to transmit communication signals 276 bi-directionally across the isolation barrier 278. The bi-directional nature of this transmission enables the medical device 110 to be a source of communication signals and send information via these signals to the cable processor 265 and the sensor 220. Similarly, this bi-directionality enables the cable processor 265 and/or the sensor 220 to be the source of communication signals and send information via these signals to the medical device 110. In an implementation, the communication signals 276 conform to a controller area network (CAN) bus protocol using two communication wires 240a and 240b that control communications based on a voltage differential between the two wires (e.g., a CAN-hi and a CAN-lo).

In an implementation, the data interface circuitry 260 includes an authentication circuit 264 and the cable contacts comprise at least one authentication cable contact 395e. In such an implementation, the conductive wires include at least one authentication wire 240e and the contacts in the port 298 include at least one authentication contact 399e. The authentication circuit 264 is configured to receive an authentication/identification (AU/ID) request from the medical device 110 via the at least one authentication cable contact 395e. Additionally, the authentication circuit 264 is configured to send AU/ID information back to the medical device 110 in response to the received AU/ID request.

Figure 2C:
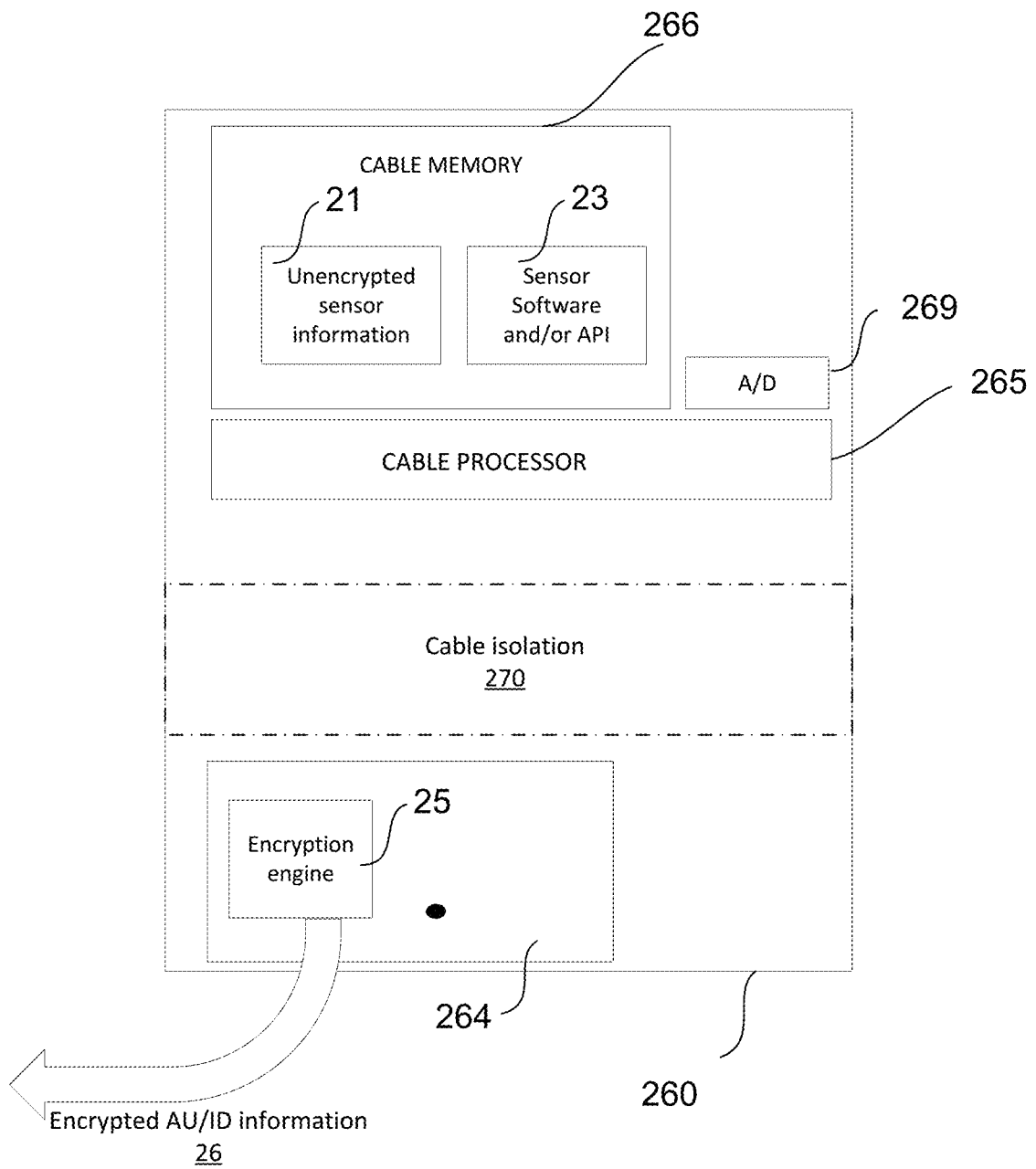
FIG. 2C shows a schematic example of information available from an authentication circuit and a cable memory.

As shown in FIG. 2C, the authentication circuit 264 may include a built-in encryption engine 25 that uses encryption keys specific to the medical device 110. For example, a manufacturer of both the medical device 110 and the data transfer cable 210 may provide for encryption keys compatible with and unique to both the medical device 110 and the data transfer cable 210 for use in authenticating the data transfer cable 210. The encryption engine 25 may provide encrypted AU/ID information 26 to the medical device 110 for use in authentication of the data transfer cable 210. In an implementation, the cable memory 266 may include stored unencrypted sensor information 21. In the absence of a malicious and/or hacked modification of the data transfer cable 210, the unencrypted sensor information 21 matches the encrypted AU/ID information 26. The cable memory 266 may further include stored sensor software and/or application programming interface (API) 23 and corresponding software/API information such as, for example but not limited to, software version number, API version number, update information, supported data protocols, sensor data formats, etc.

In various implementations, the sensor software and/or API 23 is stored in the memory 266 at the time of manufacture of the data transfer cable 210. The medical device 110 may update this software when the data transfer cable 210 is connected to the medical device 110. Alternatively, sensor data formats may be transmitted from the cable to the medical device and data formats may be updated on the medical device when the data transfer cable 210 is connected to the medical device 110. During communications with the data transfer cable 210, the medical device 110 may receive version and update information for the sensor data format, software and/or API 23. If an update is required, the medical device 110 may command the cable processor 265 to enter a download mode. The cable processor 265 can accept or reject this request based on other ongoing activities. Upon acceptance, the medical device 110 may initiate and proceed with a sensor data format, software and/or API update.

Figure 3:
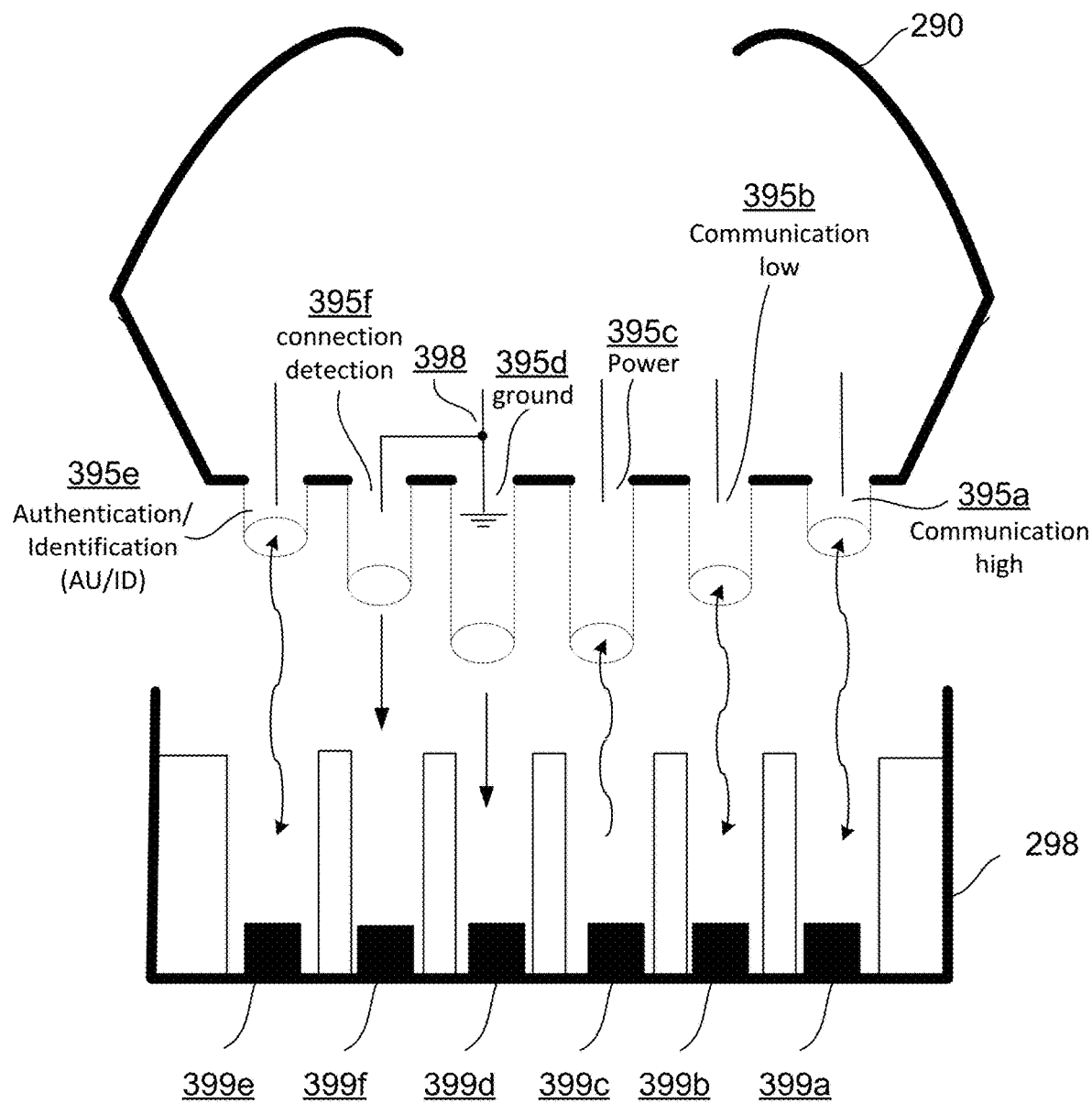
FIG. 3 shows an exemplary data cable contact configuration for the data transfer cable and data interface port in FIG. 2A.

Referring again to FIG. 2A with further reference to FIG. 3, the data transfer cable 210 further includes a second electromechanical connector 290 fixedly fastened to a second end of the cable 230. The second electromechanical connector 290 comprises cable contacts (e.g., cable contacts 395a, 395b, 395c, and 395d), each cable contact electrically coupled to a respective conductive wire (e.g., wires 240a, 240b, 240c, and 240d) of the cable 230. The second electromechanical connector 290 is configured to detachably electromechanically couple the data transfer cable 210 to the SA-DI port 298. The SA-DI port 298 includes port contacts (e.g., port contacts 399a, 399b, 399c, and 399d) configured to electrically couple to the cable contacts when the data transfer cable 210 is coupled to the port 298. The cable contacts include at least two communication cable contacts 395a and 395b, at least one power cable contact 395c, and at least one ground cable contact 395d. These cable contacts are electrically coupled to the wires 240a, 240b, 240c, and 240d, respectively. Additionally, these cable contacts are configured to electrically couple with contacts 399a, 399b, 399c, and 399d, respectively.

As illustrated herein, the port 298 is female, the second electromechanical connector 290 is male, the electrical mating 254 is female, and the electrical connector 225 are illustrated as male. However, these connection designations are examples only and not limiting of the disclosure. Connections illustrated as male may be female and, likewise, connections illustrated as female may be male. The cable contacts are illustrated as pins as an example only and the disclosure is not limited to pin/socket connection as illustrated. Various connection configurations are within the scope of the disclosure including, for example, a pin/socket contact(s) and card edge/spring contact(s).

In an implementation, the cable contacts include at least one connection detection cable contact 395f for electrically detecting a connection and/or disconnection between the data transfer cable 210 and the at least one SA-DI port 298. For example, a ground detection at the contact 399f (e.g., detection of the ground connection 398) indicates to the port 298 that the data transfer cable 210 is electrically coupled to the port 298. The connection detection cable contact 395f and contact 399f enable a detection of an unconnected state (e.g., the cable 210 is not electrically coupled to the port 298), a connected state (e.g., the cable 210 is electrically coupled to the port 298), a change of state from unconnected to connected, and a change of state from connected to unconnected (i.e., a disconnection, or removal, of the cable 210 from the port 298).

FIG. 3 provides a schematic summary of the directionality of signal transmission between the port 298 and the data transfer cable 210 via the contacts of the port and the cable contacts of the cable. The AU/ID cable contact/contact connection supports bi-directional signal transmission, the power cable contact/contact connection supports uni-directional signal transmission, and the communications cable contact/contact connections support bi-directional signal transmission.

Figure 4:
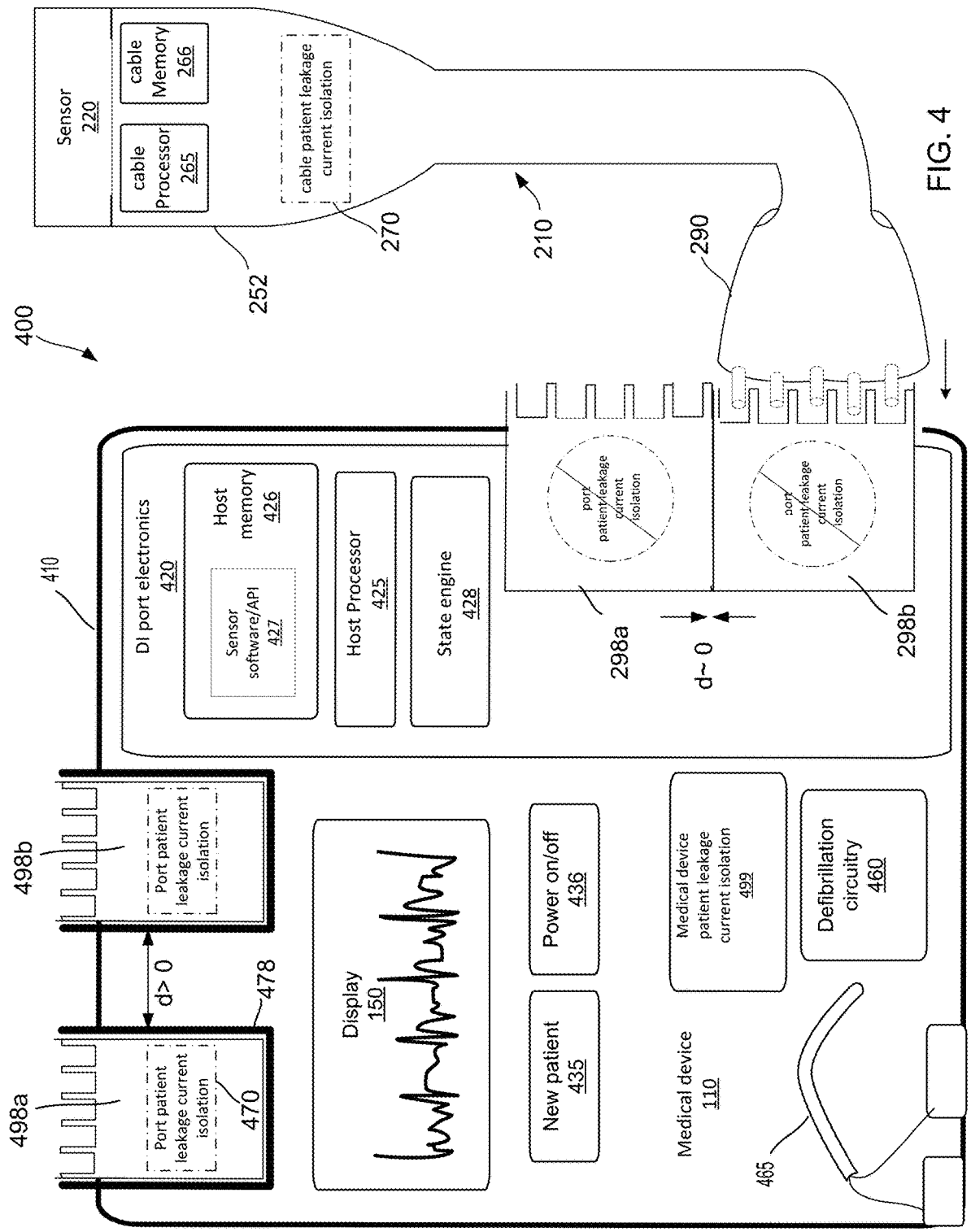
FIG. 4 shows a schematic diagram of an exemplary medical device/data transfer cable system with a sensor agnostic data interface port.

Referring to FIG. 4, a schematic diagram of an exemplary medical device/data transfer cable system with sensor-agnostic data interface ports is shown. The medical device/data transfer cable system 400 includes the medical device 110 and the data transfer cable 210. The medical device 110 includes a housing 410, a display 150, a power control 436, and at least one SA-DI port 298 (e.g., the SA-DI ports 298a and 298b). Although two ports are shown in FIG. 4, this quantity of ports is an example only and not limiting of the disclosure.

In various implementations, the medical device 110 may include one or more SA-DI ports only or a combination of one or more sensor-agnostic DI ports and one or more sensor-specific DI ports. As illustrated schematically in FIG. 4, the SS-DI ports 498a and 498b include port patient leakage current isolation 470. The SS-DI ports 498a and 498b are also spaced apart by a distance d>0 for noise reduction and electrical isolation. The SS-DI ports 498a and 498b may also include a physical element 478, such as, for example, a layer of conductive material, to reduce electromagnetic interference causing signal noise. As discussed above, these features of the SS-DI ports increase the weight and volume of the medical device 110. In contrast, the SA-DI ports 298a and 298b may exclude (i.e., not include) port patient leakage current isolation. These ports couple to a data transfer cable compatible with the SA-DI port (e.g., the data transfer cable 210) and that includes the cable patient leakage current isolation 270. Additionally, the SA-DI ports 298a and 298b are proximate to one another at a spacing approximately equal to zero. Because these ports do not include patient leakage current isolation, they do not require a noise reduction barrier or a physical layer 478. The lack of a port patient leakage current isolation, inter-port spacing, and physical noise reduction layer in aggregate over multiple SA-DI ports reduces the weight and volume of the medical device 110. In an implementation, the medical device 110 may accommodate more sensors with the SA-DI ports than with SS-DI ports and still realize an overall weight and volume reduction. Note that the medical device 110 may include additional patient leakage current isolation 499 beyond that provided by the data transfer cable 210.

The SS-DI port 498 may include a host patient leakage current isolation circuit 470. In contrast, the SA-DI ports 298a and 298b do not include (i.e., exclude) the host patient leakage current isolation circuit 470. For the SA-DI ports 298a and 298b, the function of the patient leakage current isolation is handled by the cable patient leakage current isolation 270.

The SS-DI port 498 may include a host noise shield 478. In contrast, in an implementation, the SA-DI ports 298a and 298b do not include (i.e., exclude) the host noise shield 478. For the SA-DI ports 298a and 298b, the function of the noise shield is handled by the cable noise shield 272.

The medical device 110 may further include DI port electronics 420. In an implementation one or more components of the DI port electronics 420 may be physically separate or separable from the medical device electronics (e.g., processor, memory, and associated electronics and hardware controls for therapy delivery, data collection, processing, analysis, communication, and display, etc.) and communicatively and/or electronically coupled the medical device electronics. In an implementation, the DI port electronics 420 may be integrated into and/or components of the medical device electronics. The DI port electronics 420 may include a host processor 425, a host memory 426, and a state engine 428. In an implementation, the state engine 428 may be a part of and/or a function of the host processor 425. The host processor 425 may receive sensor data from the sensor 220 via the data transfer cable 210 and may provide the sensor data to the medical device electronics for processing and/or display (e.g., at the physical display 150). In an implementation, the host memory 426 may further include stored sensor software and/or API 427 and corresponding software/API information such as, for example but not limited to, software version number, API version number, update information, supported data protocols, etc.

In an implementation, the medical device 110 may be a defibrillator or a patient monitor/defibrillator. In such an implementation, the medical device 110 includes electrotherapy delivery circuit 460 and defibrillation electrodes 465 which may also serve as ECG sensors. For example, the electrotherapy delivery circuit 460 may include one or more capacitors configured to store electrical energy for a pacing pulse or a defibrillating pulse. The electrotherapy delivery circuit may further include resistors, additional capacitors, relays and/or switches, electrical bridges such as an H-bridge (e.g., including a plurality of insulated gate bipolar transistors or IGBTs), voltage measuring components, and/or current measuring components.

The display 150 is configured to provide at least one visual representation of sensor data received by the medical device 110 via the SA-DI ports 298*a* and/or 298*b* and/or via the SS-DI port(s) 498. The visual representations may provide the data as graphical and/or textual data. The visual representations may include waveform data, for example, but not limited to ECG, pulse oximetry, and/or capnography. The visual representations may include discrete numerical data, for example, but not limited to blood pressure (NIBP, IBP) heart rate, an instantaneous pulse oximetry value and/or an instantaneous capnography value. Additionally or alternatively, the visual representations may include or provide caregiver feedback, for example, CPR feedback and/or ventilation feedback. The CPR feedback may include, for example, compression depth, compression rate, compression time, compression release, and/or perfusion performance. This display 1540 may provide the CPR feedback in real-time on a compression by compression basis. The ventilation feedback may include, for example, gas volume, ventilation rate, ventilation quality, and/or ventilation time. In an implementation, the ventilation feedback may be bag valve mask feedback. The visual representations may further include image data 1567, for example, but not limited to, laryngoscopy and/or ultrasound images. The ultrasound images may include ultrasound images of a patient's tendons, muscles, joints, internal organs, skeletal structures, abdomen and/or the patient's heart, blood vessels, carotid artery, and/or other components of the cardiovascular system. The visual representations may be part of a guided medical intervention such as biopsies, tissue or fluid samples, and/or other diagnostic or invasive procedures. In an implementation, the display 1540 may include one or more features of the display 2790 as discussed below with regard to FIG. 17F.

The DI port electronics 420 are illustrated as a distinct unit in FIG. 4 for clarity only and not limiting of the disclosure. The DI port electronics 420 may control and handle data from the SA-DI ports 298*a* and 298*b*. Although illustrated with a separation in FIG. 4, in an implementation the DI port electronics 420 may control and handle data from the SS-DI port 498. Alternatively, the SS-DI port 498 may not connect electrically and/or communicatively to the DI port electronics 420. For example, the medical device electronics may control and handle data from the SS-DI port 498.

In an implementation, the DI port electronics 420 may include the state engine 428. The DI port state engine 428, the DI port electronics 420, and/or the host processor 425 may manage each SA-DI port 298 independently from one or more other DI ports 298. The DI port state engine 428 may manage a state of the SA-DI port 298.

Figure 5:
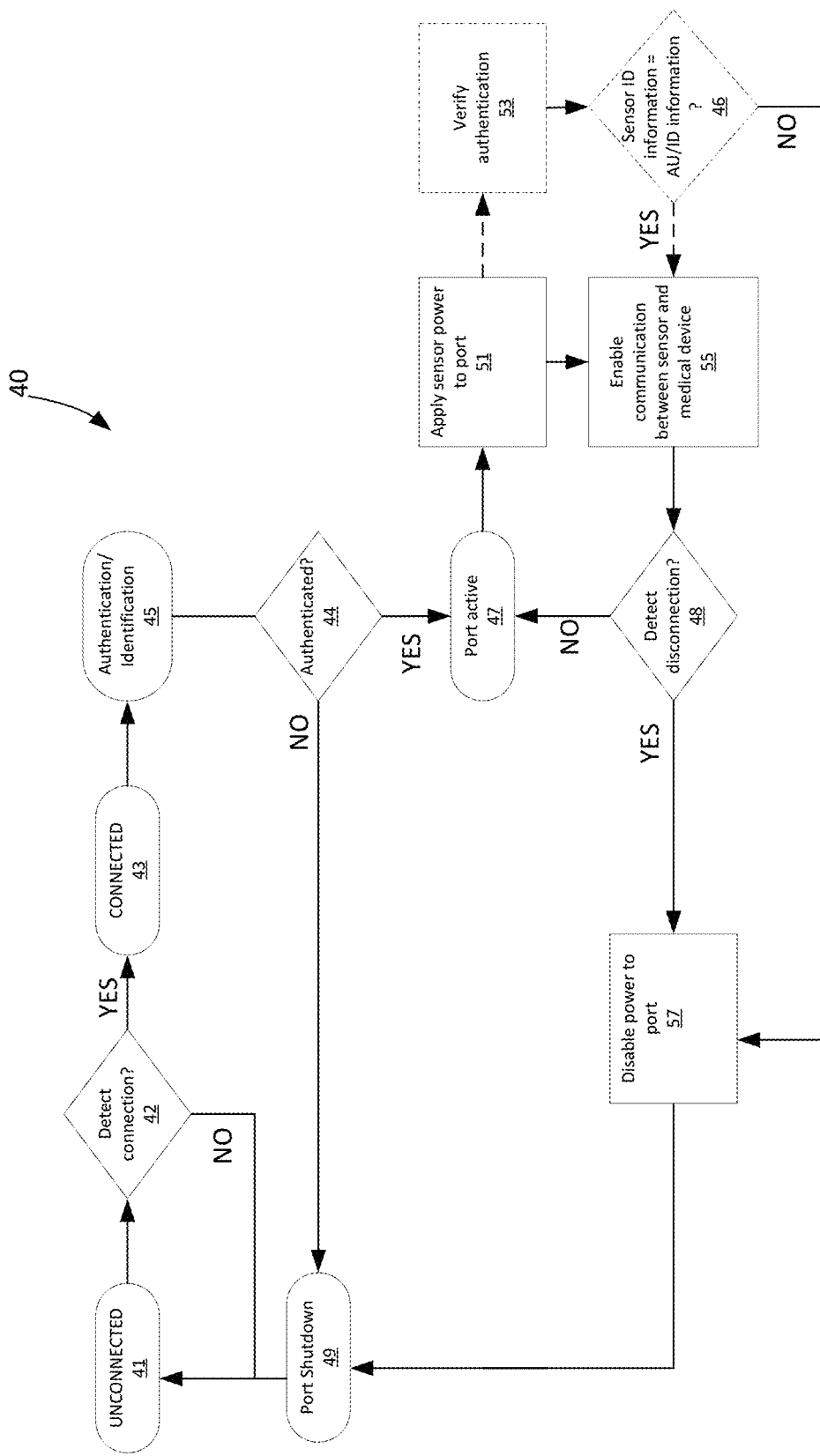
FIG. 5 shows a state diagram for the sensor-agnostic data interface port as controlled by a state engine.
Figure 6:
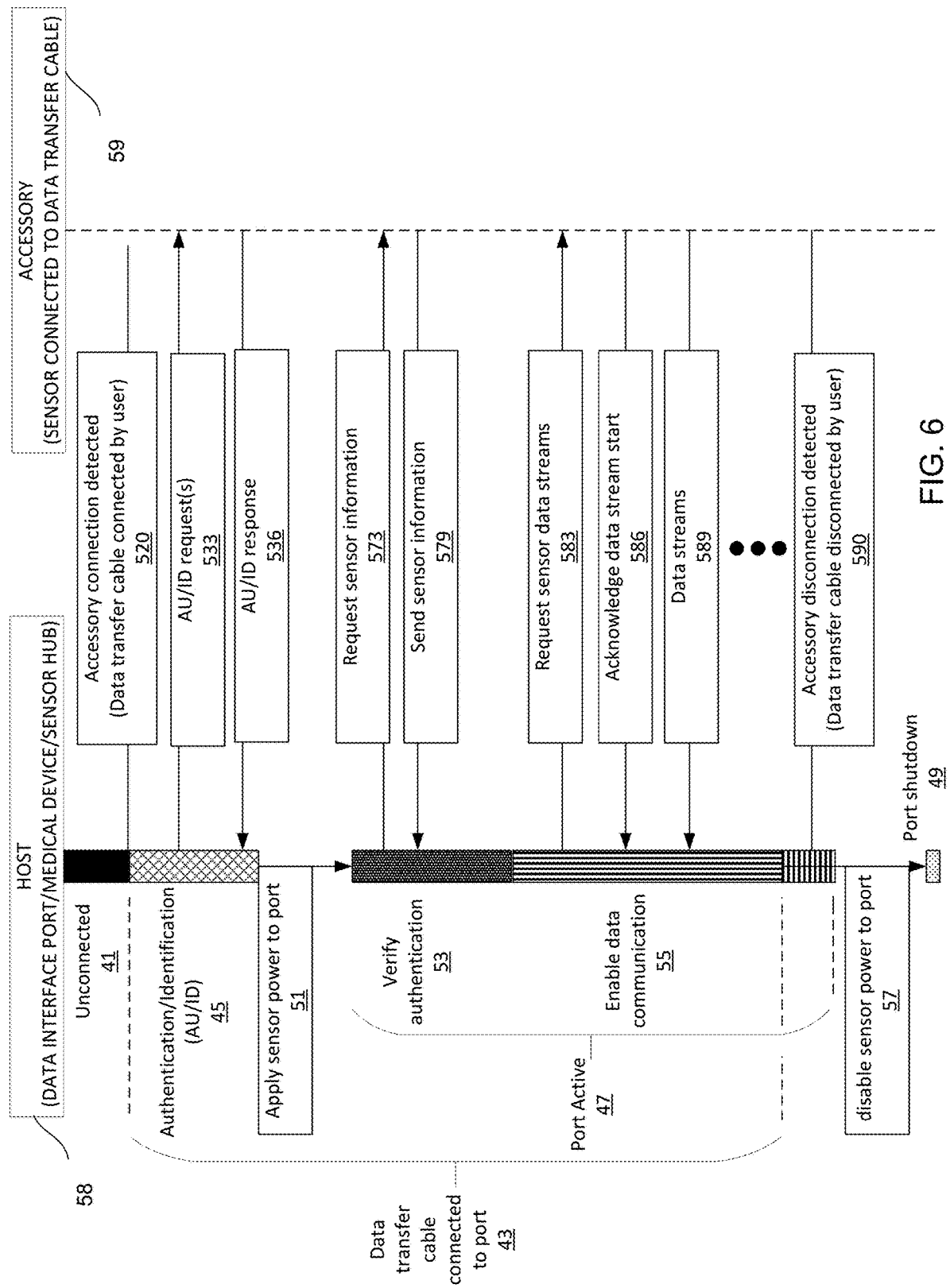
FIG. 6 shows an example of a swim lane diagram for communications and data transfer between a sensor and a data interface port via a data transfer cable.

Referring to FIG. 5, and discussed further with regard to FIG. 6, a state diagram 40 for the sensor-agnostic data interface port as controlled by a state engine is shown. The state of the SA-DI port 298 may be one of an unconnected state 41, a connected state 43, an authorization/identification state 45, a port active state 47, and a port shutdown state 49. A detection of connection 42 between the data transfer cable 210 and the SA-DI port 298 may trigger the transition from the unconnected state 41 to the connected state 43. Once in the connected state 43, the state engine 428 automatically transitions to an authentication/identification state 45. A successful authentication of the data transfer cable may trigger the transition from the authentication/identification state 45 to the port active state 47. Once in the port active state 47, the medical device 110 and/or sensor hub 1010 may apply sensor power 51 to the SA-DI port 298 and enable communications 55 between the sensor 220 and the medical device 110 and/or sensor hub 1010. In an example, prior to the application of sensor power 51 to the SA-DI port 298, the voltage on the power contact 399*c*, and on the power cable contact 395*c*, is zero volts. The medical device 110 may provide operational power for operations of the SA-DI port 298 but this power may be of insufficient quantity for operation of the sensor 220. In an implementation, in the port active state 47, the medical device 110 and/or sensor hub 1010 may verify 53 authentication of the data transfer cable 210. As described in more detail with regard to FIG. 6, with a successful verification 53, the communications 55 between the sensor 220 and the medical device 110 and/or sensor hub 1010 may proceed.

In various implementations, one or more of a failed verification, an accessory error, and a disconnected data transfer cable may trigger a transition from the port active state 47 to the port shutdown state 49. In the port shutdown state 49, the medical device 110 and/or the sensor hub 1010 may return the voltage on the power contact 399*c* to zero volts to disable sensor power 57 to the SA-DI port 298. Once in the port shutdown state 49, if the medical device 110 and/or sensor hub 1010 detects disconnection 48 or the disconnection triggered the transition to the port shutdown state 49, this detection may trigger the transition from the port shutdown state 49 back to the unconnected state 41. Therefore, in response to the electrical detection of the disconnection, the host processor 425 and/or the state engine 428 are configured to discontinue power provision to the data transfer cable 210 via the at least one SA-DI port 298. In an implementation, the unconnected state 41 is a default state of the SA-DI port 298 at power on of the medical device 110 and/or the sensor hub 1010.

Referring to FIG. 6, an example of a swim lane diagram for communications and data transfer between a sensor and a data interface port via a data transfer cable. The sequence shown in FIG. 6 is an examples only and not limiting of the disclosure. This sequences can be altered, e.g., by having stages added, removed, rearranged, combined, and/or performed concurrently. Functions described as being performed by the host 58, the medical device 110 and/or the SA-DI port 298, 298a, and/or 298b may be performed by the host processor 425 and/or another processor associated with the medical device 110 and/or the sensor hub 1010 as discussed with regard to FIG. 18. Function described as being performed by the accessory 59, the data transfer cable 210, and/or the sensor 220 may be performed by the cable processor 265 as discussed with regard to FIG. 2A.

As illustrated in FIG. 6, the communications and data transfer are between an accessory 59, for example the sensor 220 and the data transfer cable 210 and a host 58. In an implementation, the host 58 is the medical device 110 that includes at least one SA-DI port 298. Alternatively, the host 58 is a sensor hub 1010 (e.g., as described below with regard to FIGS. 11-16) physically decoupled from the medical device 110 that includes the at least one SA-DI port 298 and/or the host is the medical device 110 physically coupled to the sensor hub 1010 that includes the at least one SA-DI port 298.

Referring to the unconnected state 41 in the swim lane diagram of FIG. 6, initially the host 58 and the accessory 59 are unconnected physically and electrically and the SA-DI port 298 is an inactive state. In this inactive state, the host (e.g., the medical device 110 and/or the sensor hub 1010) does not enable and apply power to the SA-DI port 298 and there is an absence of power transmission to the data transfer cable 210 from the SA-DI port 298.

At the stage 520, a user of the accessory 59 connects the data transfer cable 210 to the SA-DI port 298. In an implementation, the port 298 may detect the connection of the cable 210, for example, via the detection cable contact 395f and detection contact 399f as described with regard to FIG. 3. In response to the connection detection, the state engine 428 may transition the SA-DI port 298 from the unconnected state 41 to the connected state 43.

In an implementation, within the connected state 43, the state engine 428 may transition the SA-DI port 298 to the authentication/identification (AU/ID) state 45. In the AU/ID state 45, the host processor 425 may send an AU/ID request 533 to the authentication circuit 264. In response to the AU/ID request 533, the authentication circuit 264 is configured to send an AU/ID response 536. The exchange of the AU/ID request 533 and the AU/ID response 536 may occur via the at least one AU/ID contact 399e, the AU/ID cable contact 395e, and the authentication wire 240e.

In an implementation, the exchange of the AU/ID request 533 and the AU/ID response 536 occurs without power transmission to the cable 210 from the host 58. Furthermore, the isolation 270 electrically separates the authentication circuit 264 from the cable processor 265. In this manner, the authentication and identification of the accessory 59 occurs before the host 58 provides power to the cable processor 265 and the sensor 220. Therefore, the processor 265 and the sensor 220 are prevented from communicating with the host 58 until authentication and identification are complete. In the absence of authentication of the accessory 59 (e.g., authentication sequence incomplete and/or failed authentication), the host processor 425 and/or the state engine 428 may disable the SA-DI port 298 and thereby disable a provision of power to the cable 210.

The AU/ID response 536 includes AU/ID information that authenticates the accessory as a valid accessory recognized by the host 58 and that identifies the sensor 220. For example, a valid accessory may include a sensor and data transfer cable that provide data in a format compatible with the SA-DI port 298 and are identified by the host manufacturer as compatible with the medical device 110. The AU/ID information may include, for example but not limited to, a model number, a serial number, a hardware revision number, and/or power requirements for the sensor 220. In an implementation, the authentication circuit 264 provides encrypted AU/ID information 26 in response to the received AU/ID request 533. The encrypted AU/ID information 26 may include identification information for a manufacturer of the sensor. In an implementation, the manufacturer of the medical device 110 may provide or offer the medical device 110 with various hardware and/or software configuration options. The AU/ID information may indicate compatibility between a specific medical device configuration and a specific accessory configuration.

Figure 9A:
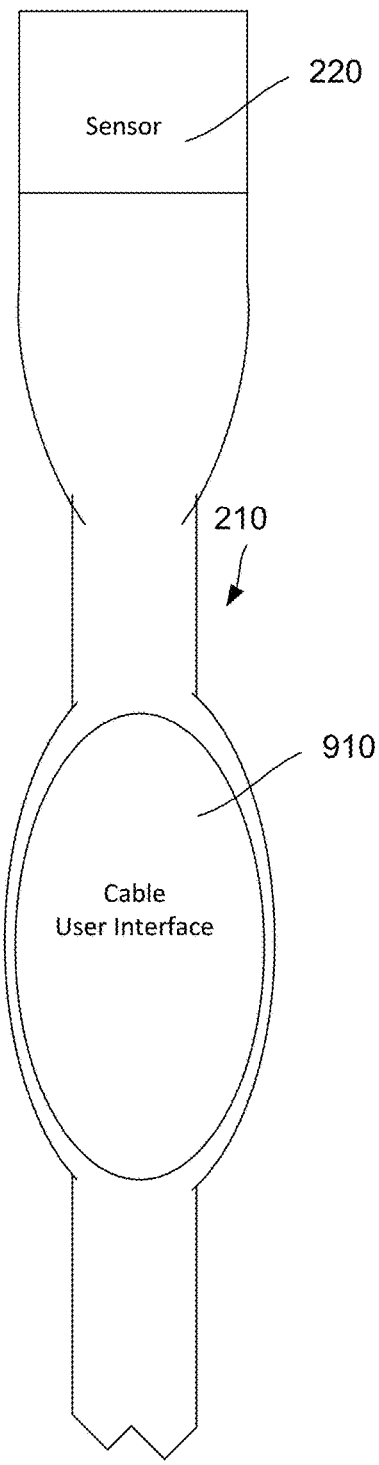
FIG. 9A shows a schematic diagram of an exemplary data transfer cable with cable user interface.

In an implementation, failure to authenticate may cause the host processor 425 to generate a user notification, for example, at the display 150 and/or at a cable display 910 (e.g., as discussed with regard to FIG. 9A). In an implementation, in response to a failed authentication, the state engine 428 may transition the SA-DI port 298 to the port shutdown state 49 and require a detection of disconnection of the data transfer cable 210 before enabling a subsequent port active state 47.

In an implementation, the host 58 may determine if the accessory 59 is a newly connected accessory or a reconnected accessory based on the AU/ID information. In an example of a usage scenario, the user may have a first accessory (e.g., a first sensor and a first data transfer cable) and a second accessory (e.g., a second sensor and a second data transfer cable). The user may connect the first accessory, disconnect the first accessory, and connect the second accessory to the same SA-DI port 298. Alternatively, the user may connect the first accessory, disconnect the first accessory, and reconnect the first accessory to the same SA-DI port 298. The first accessory may be a newly connected and then reconnected IBP sensor. The host 58 may recognize the AU/ID information at the reconnection from the initial connection. Alternatively, the user may connect the first accessory, disconnect the first accessory, and connect the second accessory to the same SA-DI port 298. For example, the first accessory may be a newly connected IBP sensor and the second accessory may include a newly connected temperature sensor. Based on the AU/ID information, the host may identify the second accessory as a new and different accessory from the first accessory. In an implementation, the authentication circuit 264 may send the AU/ID information in the AU/ID response 536 as encrypted AU/ID information 26 using the encryption engine 25.

In an implementation, the host 58 may identify the connection of a particular sensor as a new connection if the connection occurs after the medical device 110 is powered-on (e.g., via the power on/off control 436) and following a particular powered-off duration (e.g., at least 30 seconds). Additionally, the host 58 may identify the connection of a particular sensor as the new connection if the connection occurs after an indication of a new patient (e.g., via the new patient control 435). A new connection corresponds to a first connection during a patient case. A patient case starts in response to power-on of the medical device 110 after the particular powered-off duration and/or in response to a new patient indication. Similarly, a patient case ends in response to power-off of the medical device 110 for the particular powered-off duration and/or in response to the new patient indication.

Upon completion of the AU/ID state 45 and in response to a successful authentication, the host 58 may apply power to the SA-DI port 298 and apply sensor power 51 to the SA-DI port 298 to enable power transmission to the sensor 220. The state engine 428 may transition the SA-DI port 298 to the port active state 47. For example, the host processor 425 may authenticate the sensor 220 based on the encrypted AU/ID information 26 in the AU/ID response 536 and enable power provision to the data transfer cable 210 via the at least one power contact 399C and power cable contact 395C based on the authentication.

In an implementation, in the port active state 47, the host processor 425 may verify 53 authentication. The host 58 may send a request 573 for sensor information from the SA-DI port 298 to the cable processor 265 via the at least two communication contacts 399A and 399B and the at least two communication cable contacts 395A and 395B. In an implementation, this request 573 may include the software and/or application programming interface (API) information for the SA-DI port 298 and/or the host processor 425.

The accessory 59 (e.g., the cable processor 265) receives the request 573 from the SA-DI port 298 at the host 58 via the communication signals 276 transmitted by the isolation 270. In response, the accessory 59 executes software stored in the memory 266 to determine the requested sensor information and sends 579 the requested sensor information back to the host 58 via the communication signals 276 transmitted by the isolation 270.

In an implementation, the unencrypted sensor information 21 includes one or more of sensor identification information (e.g., a model number, manufacturer, and/or serial number), software and/or API information for the data transfer cable 210. The sensor information may enable the host 58 to confirm compatibility with the accessory 59 and identify data processing services necessary to handle the sensor data prior to receiving the sensor data streams.

Upon receipt of the unencrypted sensor information 21, the host processor 425 may compare the encrypted AU/ID information 26 received from the authentication circuit 264 with the unencrypted sensor information 21 from the cable processor 265. If the originally manufactured state of the data transfer cable 210 is intact, then the unencrypted sensor information 21 will match the encrypted AU/ID information 26. However, if, for example, a nefarious actor altered a third party cable unauthorized for use with the medical device 110 by adding an authentication circuit 264 and authentication wire/cable contact from a data transfer cable 210 authorized for use with the medical device 110, the verification 53 would fail. In this situation, the unencrypted sensor information 21 will not match the encrypted AU/ID information 26. In response, the host 58 may disable the SA-DI port 298 and transition back to a port shutdown state 49. In this manner, the host 58 may block communications with a counterfeit or knock-off data transfer cable.

If the encrypted AU/ID information 26 does not correspond to the unencrypted sensor information 21, then the host 58 may disable sensor power 57 to SA-DI port 298 and the data transfer cable 210. Conversely, if the encrypted AU/ID information 26 corresponds to the unencrypted sensor information 21, then the host 58 may remain in the port active state 47 and enable data communication 55 between the host 58 and the accessory 59.

In an implementation, during enabled data communication 55, the host 58 may send a request 583 for sensor data streams via the at least one SA-DI port 298 to the cable processor 265 of the accessory 59. In the port active state 47, the cable processor 265 may receive power signals 274 transmitted by the isolation 270 and may receive the request 583 via communication signals 276 transmitted by the isolation 270. In response to the request 583, the cable processor 265 may execute software/API 23 stored in the memory 266 to format the sensor data in the sensor-agnostic data format according to the protocol of the SA-DI port 298. The cable processor may send 589 sensor data streams in the sensor-agnostic format back to the host 58 via communication signals 276 transmitted by the isolation 270.

In an implementation, prior to receiving and sending sensor data streams, the host 58 may request an accessory status and receive an accessory status response from the cable processor 265. The accessory status response may include indications of faults, a current value of a timestamp and sequence number, a connection status with the patient, and/or combinations thereof. The timestamp may be a millisecond based time stamp referenced to the time of port active 47 (i.e., time is initialized to zero when the port is activated). The sequence number is a number associated with each message in a stream of data messages for proper sequencing and detection of missing data. The accessory status response may also include a hardware version number, a sensor manufacture date, and/or a sensor expiration date.

In various implementations, the sensor data streams include one or more of sensor parameter status data, numeric data, and waveform data. The data stream may also provide data information, for example, an update rate for a discrete numerical parameter or a sampling rate (e.g., messages/second, bits per sample, and samples/message) for a waveform parameter. In an implementation, if the host 58 fails to detect active data streams for a predetermined period of time, the host 58 may poll the accessory 59 to determine if the accessory 59 is still functional.

In an implementation, the medical device 110 may include a plurality of SA-DI ports 298 (e.g., 3-6, 3-10, 6-12 ports). Based on power delivery limitations, the medical device 110 may limit a number L of activated SA-DI ports 298 where L<M. For example, the medical device 110 may be configured to deliver a total amount of power $P_{total}$ to the aggregate group of SA-DI ports 298. Each sensor connected to a SA-DI port 298 may require an amount $P_{sensor, 1}$, $P_{sensor, 2}$, ... $P_{sensor, N}$. The total number of SA-DI ports 298 provided by the medical device 110 may be M ports. As sensors are connected to the SA-DI ports 298, if the total required sensor power ($P_{sensor, 1}+P_{sensor, 2}+ \cdots +P_{sensor, N}$) exceeds the total amount of power $P_{total}$ available from the medical device (i.e., $P_{sensor, 1}+P_{sensor, 2}+ \ldots + P_{sensor, N}>P_{total}$), the medical device 110 may limit a number of activated SA-DI ports 298 to a number L less than the total number of SA-DI ports 298 provided by the medical device 110 (i.e., L<M). The number L of activated ports depends on the power, $P_{sensor, N}$, required for each connected sensor. Therefore, the maximum number of activated SA-DI ports 298 depends on the specific power requirement of each connected sensor 220. Thus, the host processor 425 is configured to limit a number of sensor-agnostic data interface ports that concurrently transfer power to less than a total number of sensor-agnostic data interface ports. The AU/ID information includes the specific power requirement of a connected sensor 220. Therefore, the medical device 110 can determine whether or not to activate a specific SA-DI port 298 with a connected sensor 220 based on this power requirement. Thus, the host processor 425 is configured to limit the number of SA-DI ports 298 based on the AU/ID information.

In an implementation, in addition or as an alternative to limiting a total number of activated SA-DI ports 298 based on total power requirements, the medical device 110 may also limit the total number of SA-DI ports 298 connected to a particular type of sensor. For example, the host processor 425 may be configured to limit the number of SA-DI ports 298 connected to IBP sensors to three ports connected to an invasive blood pressure sensor. In an implementation, the host processor 425 may be configured to limit the number of SA-DI ports 298 connected to particular types of sensors based on sensor priority. For example, an airway flow sensor and/or an invasive blood pressure sensor have higher priority than a temperature sensor.

In an implementation, the software and/or API 23 stored in the memory 266 is installed during manufacturing and is updated via the host 58. For example, as discussed above, the accessory 59 provides software and/or API version information during the verification of the data transfer cable.

Figure 7A:
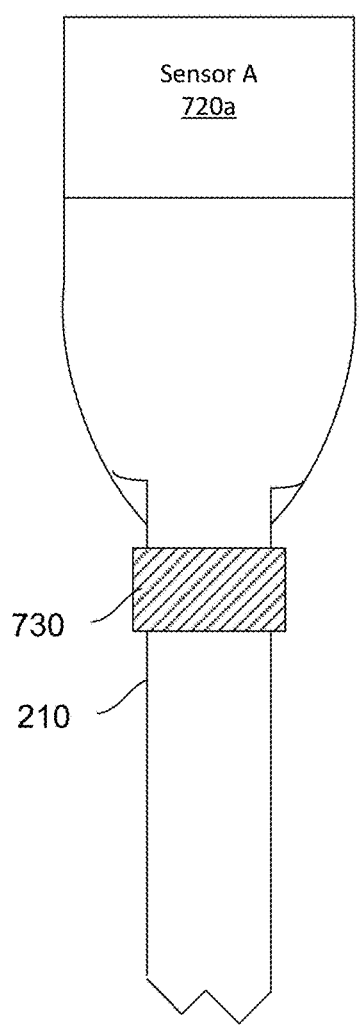
FIGS. 7A-7F show exemplary cable illumination configurations for a data transfer cable.
Figure 7B:
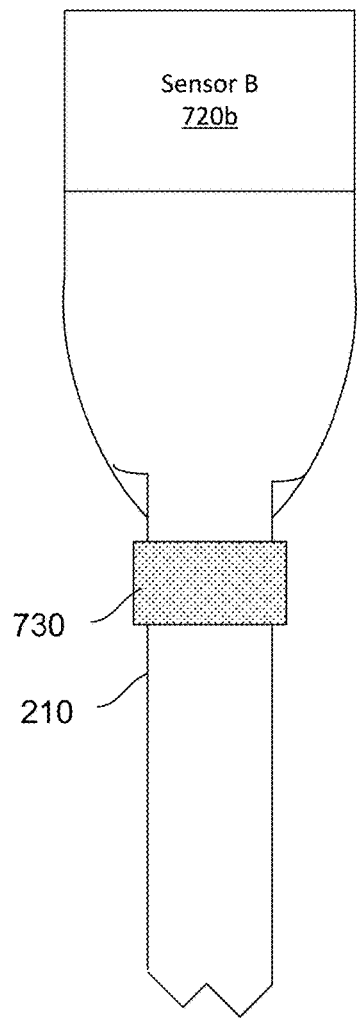
Figure 7C:
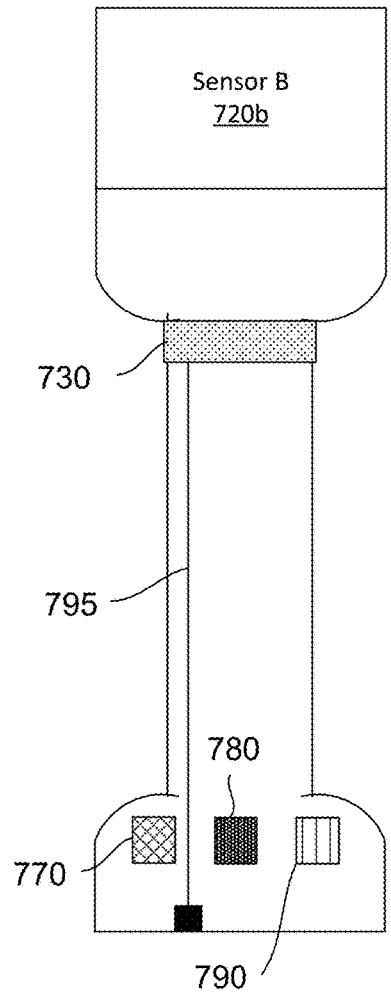
Figure 7D:
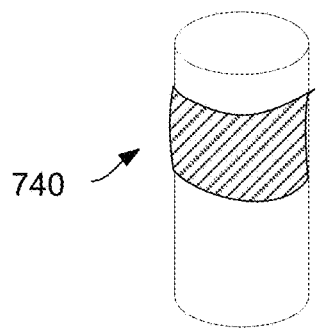
Figure 7E:
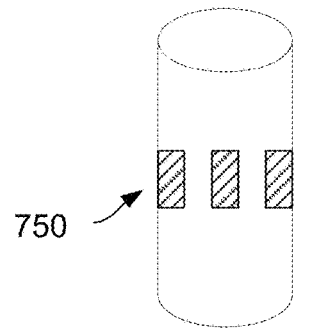
Figure 7F:
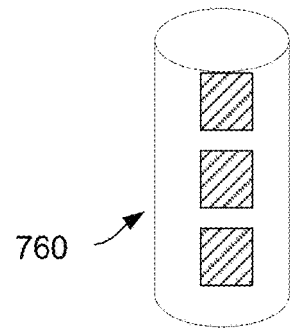

Referring to FIGS. 7A-7F, examples of cable illumination configurations for a data transfer cable are shown. The data transfer cable 210 may be coupled to a first sensor 720a or to a second sensor 720b of a different type than the first sensor. For example, the first sensor 720a may be a temperature sensor and the second sensor 720b may be an IBP sensor. The data transfer cable 210 may include at least one illumination device 730 disposed on the cable. The illumination device 730 may illuminate in a first color (e.g., as shown schematically by cross-hatches in FIG. 7A) corresponding to the first sensor 720a or in a second color (e.g., as shown schematically by the dot pattern in FIG. 7B) corresponding to the second sensor 720b. In this way, a caregiver may readily identify the type of sensor attached to the cable based on the illuminated color. As an example not limiting of the disclosure, the at least one illumination device 730 may include a light emitting diode (LED). In various implementations, the at least one illumination device 730 may be a band 740 that surrounds a circumference of the data transfer cable 210, as shown in FIG. 7D, or a series of two or more discrete devices arranged circumferentially 750, as shown in FIG. 7E, or radially 760, as shown in FIG. 7F, along the cable 210.

Referring to FIG. 7C, the data transfer cable 210 may include multiple illumination devices disposed on the cable 230 and/or on one or more of the electromechanical connectors 250 and 290. The multiple illumination devices may have different assigned colors to indicate one or more of a power on state, a power off state, an authentication state, a sensor fault state, a sensor working state, a sensor type, a communication state, etc. The illumination devices may indicate this sensor status information based one or more of color, continuity of illumination (e.g., blinking or continuous or various rates of blinking), and an absence of illumination.

In an implementation the illumination device 730 may provide infrared illumination. For example, the wavelength of the infrared illumination may be in the range of 900-1750 nm. The infrared illumination may provide an advantage in military settings by enabling identification of the sensor, for example with night vision goggles. In an implementation, the data transfer cable 210 may include a low light sensor 860 electrically coupled to the at least one illumination device 730 and configured to disable illumination under low light conditions.

Figure 8:
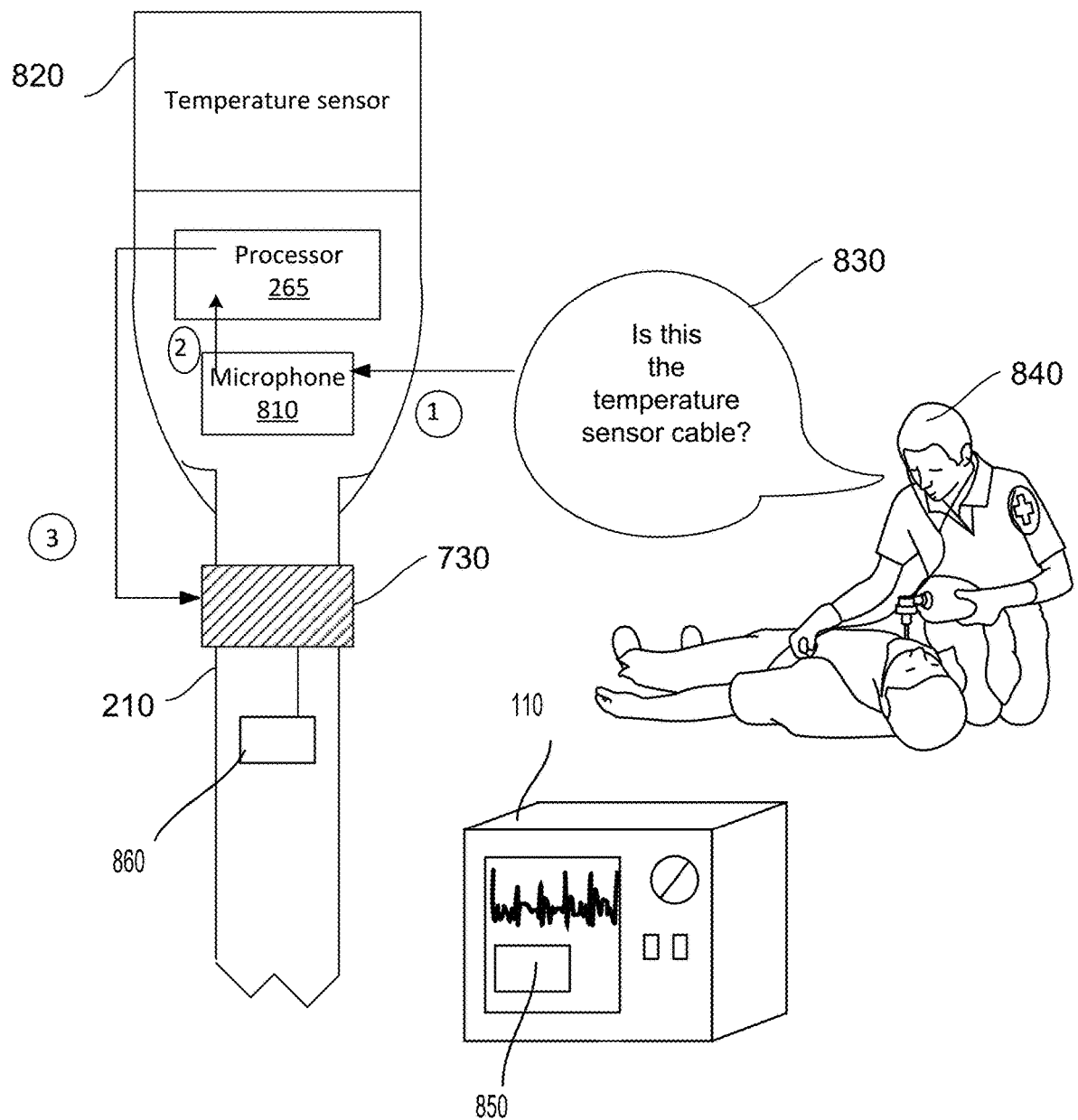
FIG. 8 shows a schematic diagram of an exemplary user input controlled cable illumination for a data transfer cable.

Referring to FIG. 8, an example of user input controlled cable illumination for a data transfer cable is shown. In an implementation, the illumination device 730 may illuminate in response to a voice input 830 from a caregiver 840 for the type of sensor 820 on the data transfer cable 210. For example, the data transfer cable 210 may include a microphone 810. The microphone may capture the voice input 830, provide the voice input 830 to the processor 265. The processor 265 may recognize a sensor identification query from the voice input 830, verify the sensor type, and cause the illumination device 730 to illuminate in response to the voice input 830. In an implementation, the device 730 may illuminate in a steady or flashing mode.

Figure 9B:
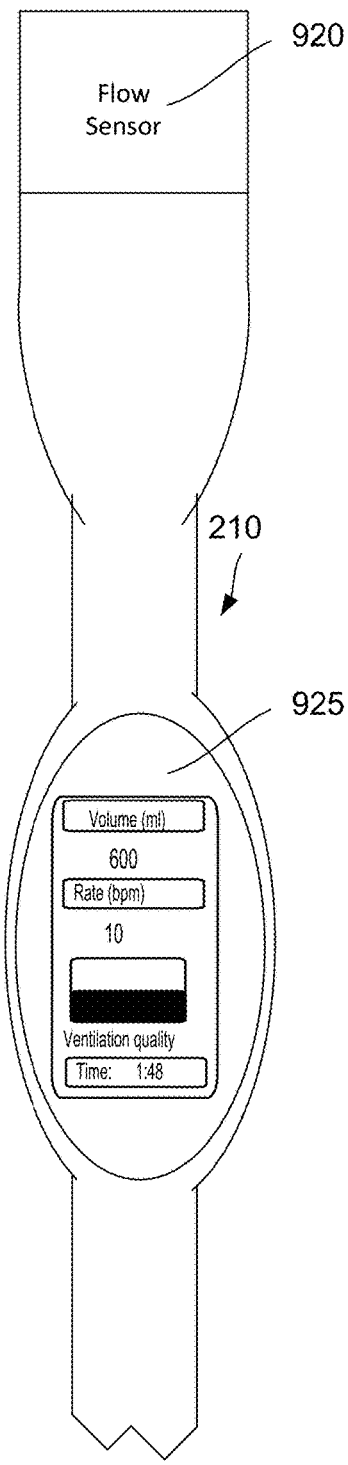
FIG. 9B shows an example of a data transfer cable with an airway flow sensor and airway flow sensor user interface.
Figure 9C:
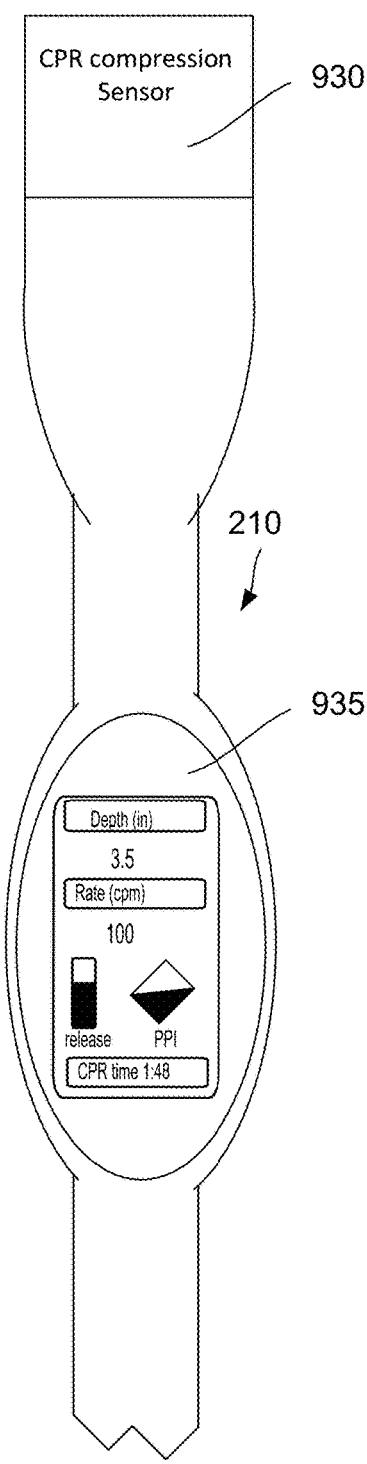
FIG. 9C shows an example of the data transfer cable with a CPR compression sensor and CPR compression sensor user interface

Alternatively or additionally, the illumination device 730 may illuminate in response to user input to the medical device. For example, the medical device 110 may include a button and/or touch screen control 850 configured to accept a user inquiry to identify a sensor type on a data transfer cable. The host processor 425 may cause the illumination device 730 to illuminate in response to the user input at the medical device 110. In an implementation, the data transfer cable 210 may include an identification contact/wire combination 795, as shown in FIG. 7C, for cable identification queries. The host processor 425 may provide a signal to the illumination device 730 via this identification contact/wire combination 795. In an implementation, the host processor 425 may cause the illumination device 730 to illuminate in response to a user touch and/or other user input (e.g., a cursor or other selectable screen indicator) to the display 150 at the at least one visual representation of the data from the sensor 220. Referring to FIG. 9A, an example of a data transfer cable with cable user interface is shown. In an implementation, the data transfer cable 210 may include a cable user interface 910. The user interface 910 may include a display configured for user input and/or output (e.g., caregiver feedback, caregiver prompting, sensor data display, etc.). The user interface 910 may be positioned or disposed along the cable 230 or at an electromechanical connector (e.g., the connector 250 or 290). The user output may depend on the type of sensor coupled to the data transfer cable 210. For example, FIG. 9B shows a data transfer cable 210 with an airway flow sensor 920 and an airway flow sensor user interface 925. The user interface 925 may provide bag valve mask feedback, for the user to administer ventilations according to desired ventilation targets, for example, within predetermined range(s) for ventilation tidal volume, ventilation rate, ventilation minute volume, etc. As another example, FIG. 9C shows a data transfer cable 210 with a CPR compression sensor 930 and a CPR compression sensor user interface 935, for the user to administer chest compressions according to desired chest compression targets, for example, within predetermined range(s) for chest compression depth, chest compression rate, release velocity, etc. In certain embodiments, as depicted in FIGS. 9B and 9C, the user interface 925, 935 may depict numerical values that illustrate the respective ventilation/compression parameters. In addition, or alternatively, the user interface 925, 935 may provide instructive feedback for the user if the ventilation and/or compression parameters are outside of the desired target range. For example, if the ventilation tidal volume is outside of the desired target range, then a portion of the user interface 925 may provide a visual indication (e.g., highlighting the numerical value representing tidal volume) that the user should pay attention to how much tidal volume is being administered to the patient. Similarly, if the ventilation rate is outside of the desired target range, then a portion of the user interface 925 may provide a visual indication (e.g., highlighting the numerical value representing ventilation rate) that the user should adjust how fast or slow ventilations are being administered. In some embodiments, when the compression depth is outside of the desired target range, then the user interface 935 may indicate (e.g., highlight of the numerical value representing compression depth) that the user should adjust the depth of chest compressions given. And when the compression rate falls outside of the desired target range, then the user interface 935 may similarly indicate (e.g., highlight the numerical value representing compression rate) that the user is outside of the target range.

In an implementation, the cable user interface 910 may provide user output for data other than data from the sensor 220 that is coupled to the data transfer cable. For example, the medical device 110 may provide data collected via other sensors to the cable user interface 910 to improve medical care provided by the caregiver. For example, a cable user interface for a CPR compression sensor may provide vital sign data or bag valve mask data that may aide the caregiver in their CPR response.

Figure 10:
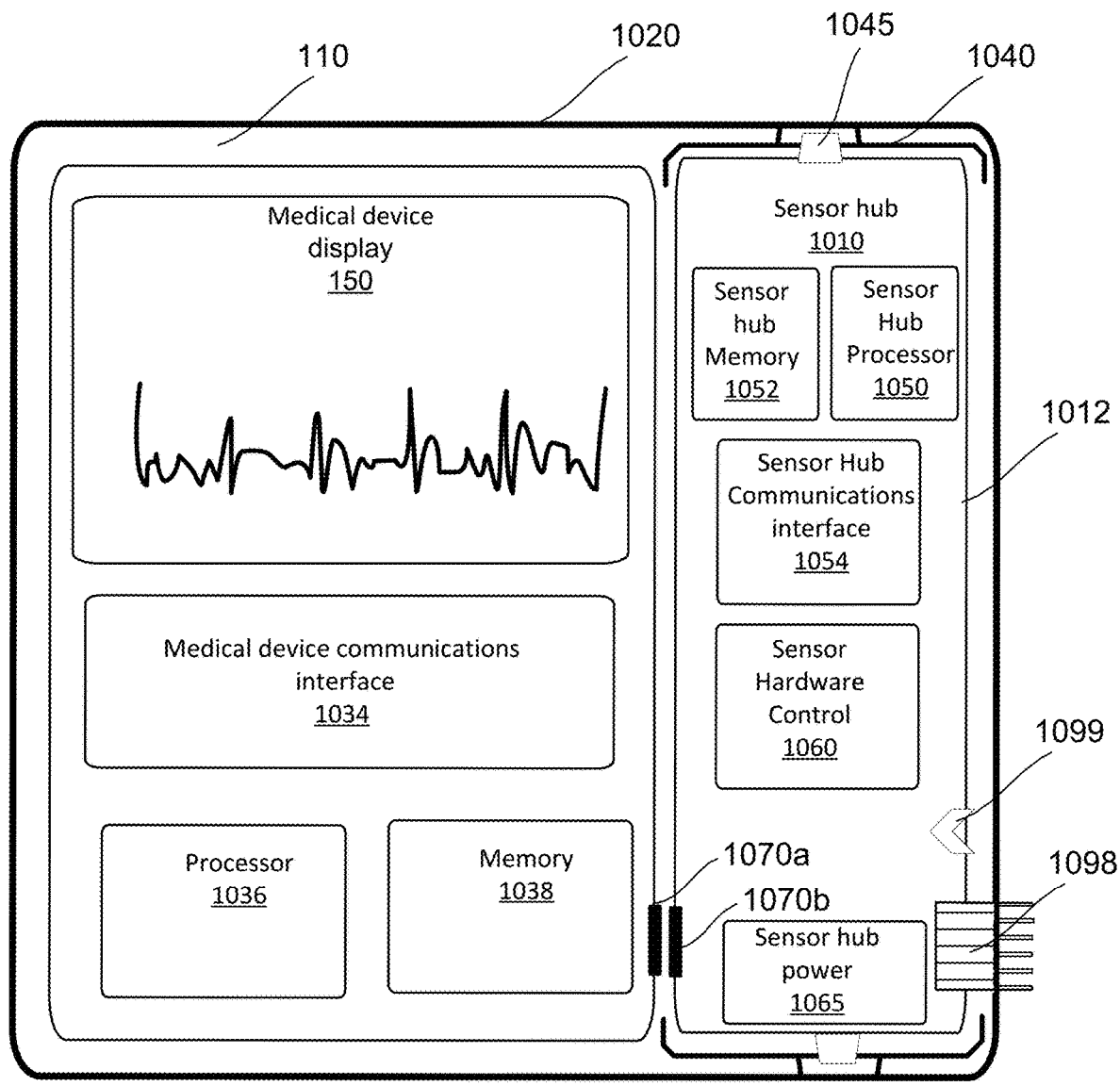
FIG. 10 shows a schematic diagram of a removable sensor hub physically coupled to a medical device inside of a medical device housing.
Figure 11:
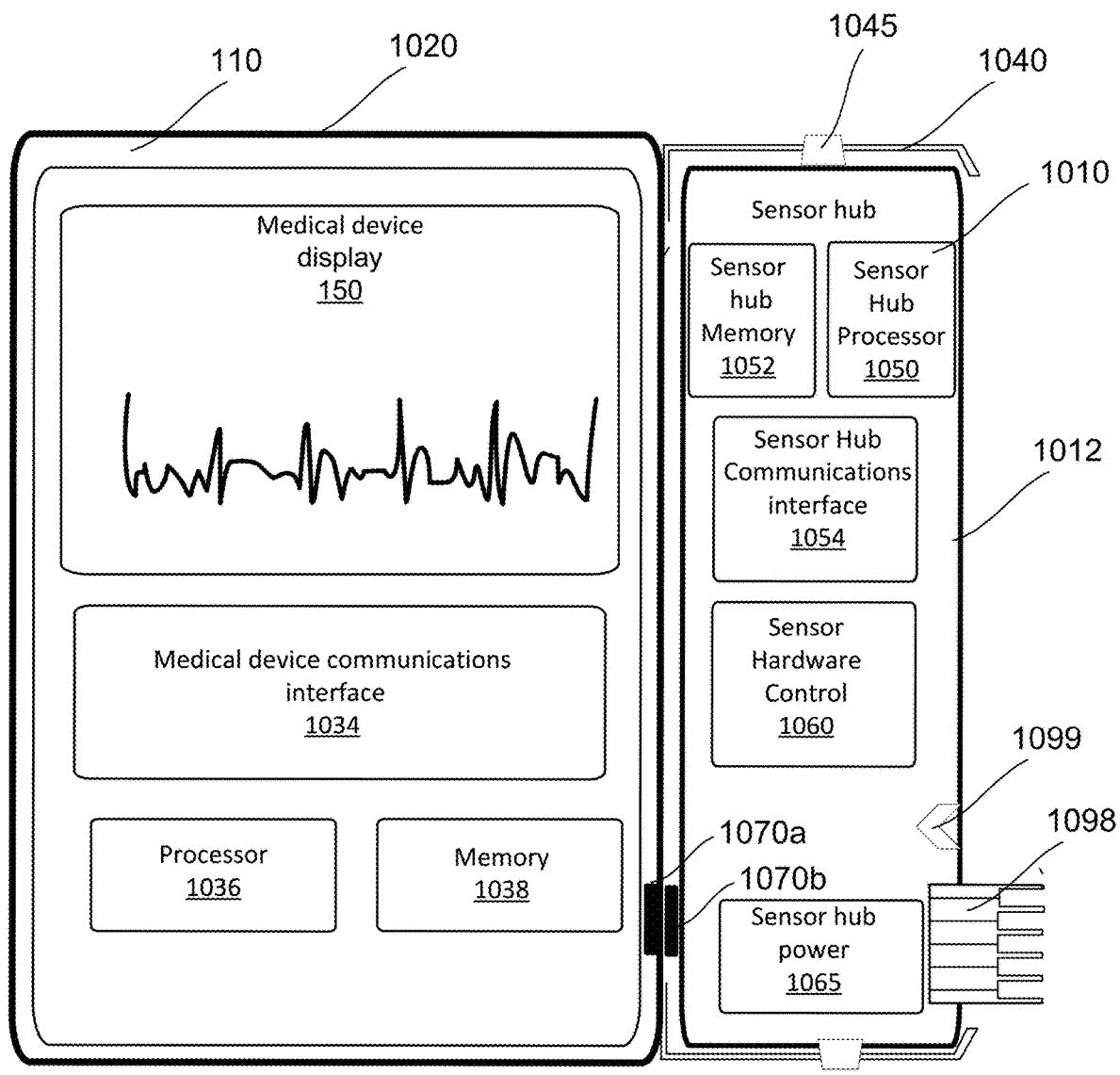
FIG. 11 shows a schematic diagram of a removable sensor hub physically coupled to a medical device outside of a medical device housing.

Referring to FIGS. 10 and 11, a schematic diagrams of a removable sensor hub coupled to a medical device inside and outside of a medical device housing, respectively, are shown. The medical device 110 includes a housing 1020 (e.g., a first housing), a medical device display 150 (e.g., a first display) coupled to the housing 1020, a communications interface 1034 (e.g., a first communications interface), a processor 1036 (e.g., a first processor), a memory 1038 (e.g., a first memory), and associated circuitry. The processor 1036 and the memory 1038 are communicatively coupled to the display 150 and the communications interface 1034.

Figure 12:
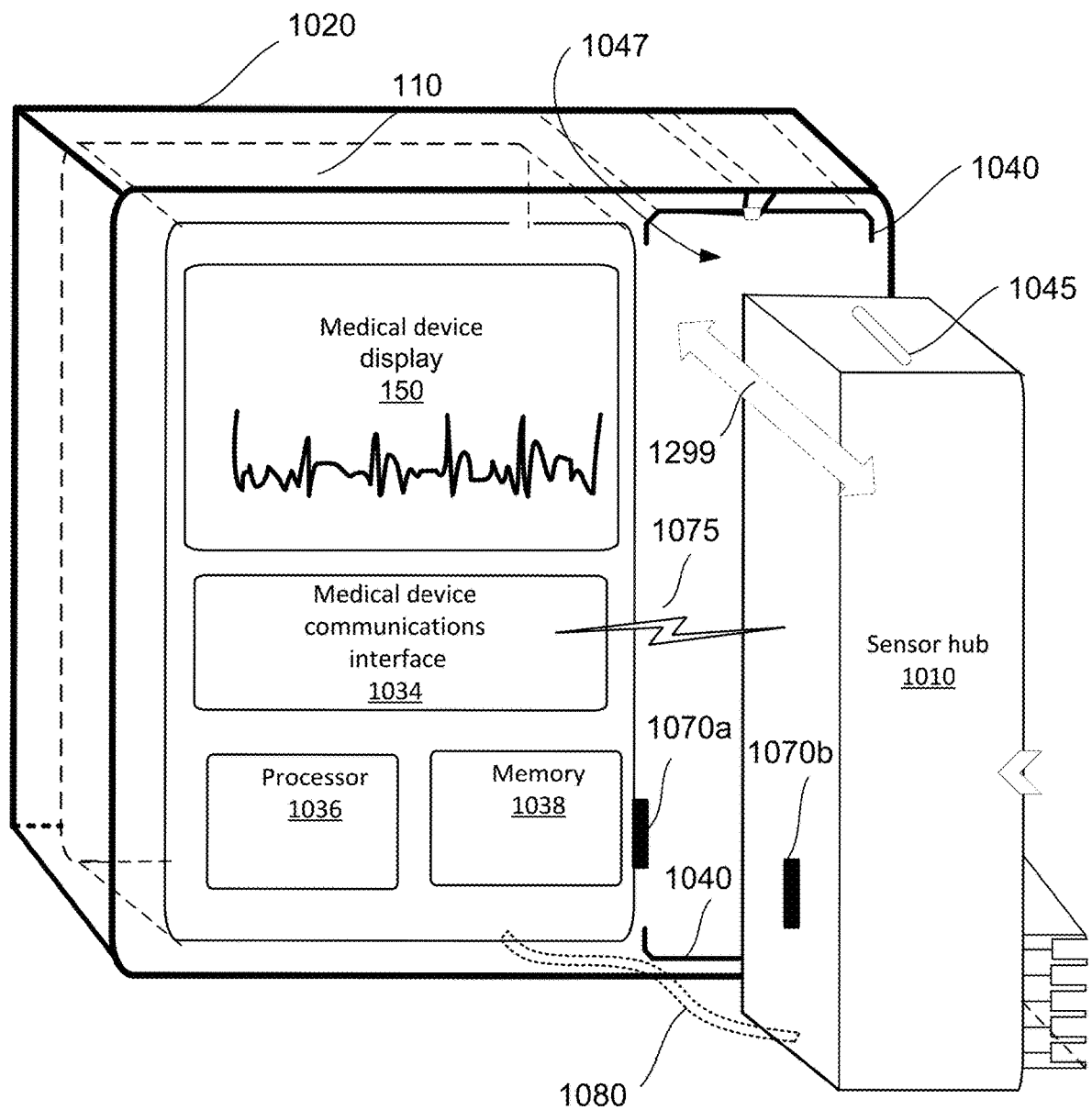
FIG. 12 shows a schematic diagram of sensor hub removal from an interior medical device coupling.
Figure 13:
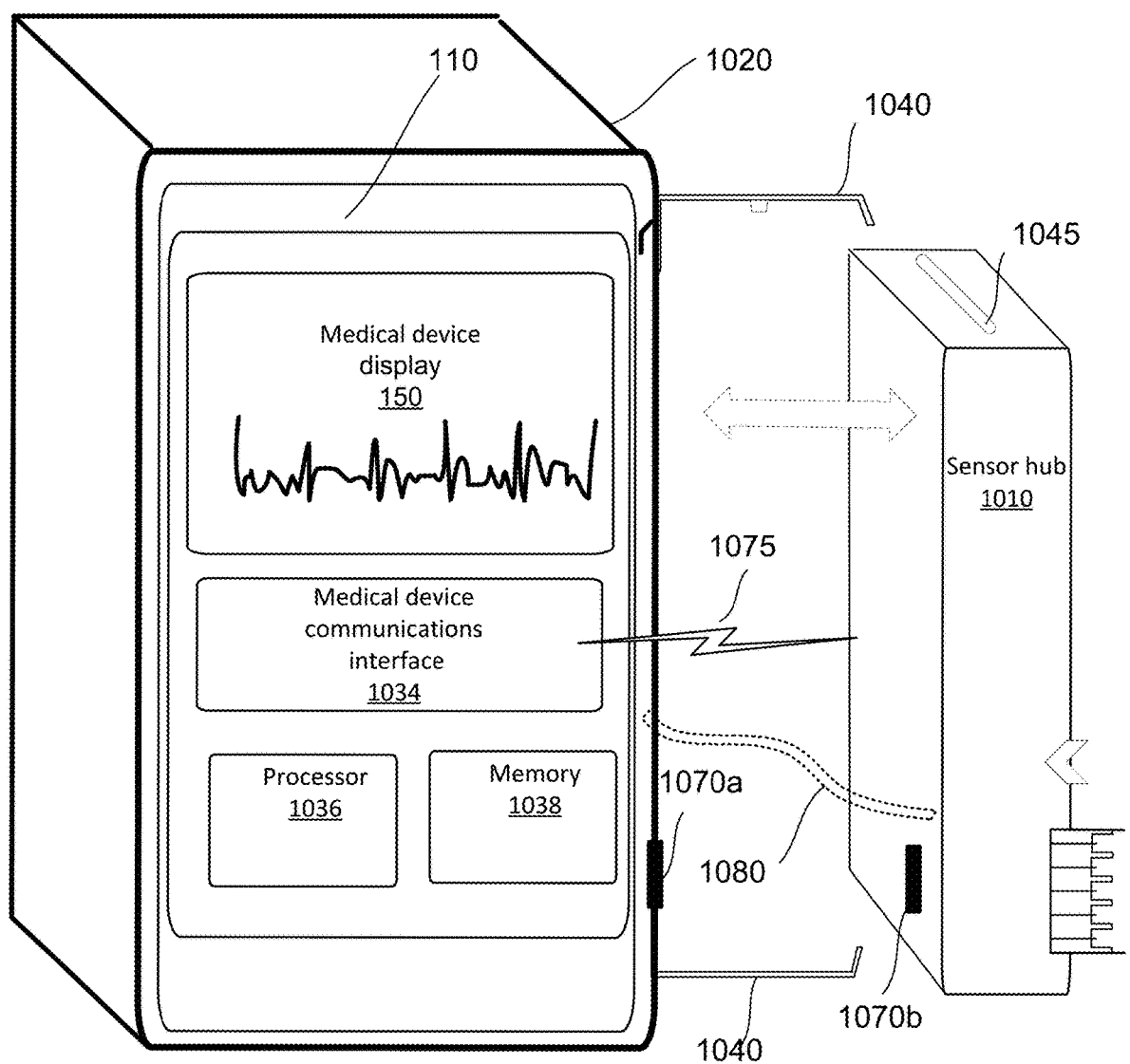
FIG. 13 shows schematic diagram of sensor hub removal from an exterior medical device coupling.

In an implementation, the housing 1020 may include a sensor hub connector 1040. In various implementations, the sensor hub connector 1040 may be disposed within the housing 1020 (e.g., as shown in FIG. 10) or may be disposed on the outside of the housing 1020 (e.g., on an exterior surface as shown in FIG. 11.). Referring to FIG. 12, the sensor hub connector(s) 1040 disposed within the housing 1020 may be, for example, form a receptacle 1047 configured to accept insertion (e.g., as indicated by the arrow 1299) of the sensor hub 1010 and retain the sensor hub 1010 within the housing 1020. The receptacle 1047 is also configured to release (e.g., as indicated by the arrow 1299) the sensor hub 1010 for removal from the medical device 110. Referring to FIG. 13, the sensor hub connector(s) 1040 disposed on the exterior of the medical device 110 may comprise one or more of bracket, a clip, a clamp, a magnet, a receptacle, etc. configured to secure the sensor hub 1010 to the exterior of the housing 1020. The sensor hub 1010 may include one or more mating mechanisms 1045 configured to removably couple to the sensor hub connector 1040. In an implementation, the mating mechanism 1045 may be a contour on the sensor hub 1010.

In an implementation, the sensor hub connector 1040 may enable a wired electrical and/or communicative coupling between the sensor hub 1010 and the medical device 110 via one or more contacts 1070a and 1070b. In an implementation, the contacts 1070b (e.g., one or more first electrical contacts) may be disposed on the sensor hub 1010 and the contacts 1070a (e.g., one or more second electrical contacts) may be disposed on the medical device 110. The sensor hub connector 1040 may retain the sensor hub 1010 in a position in which these contacts touch one another. In an implementation, the sensor hub 1010 and the medical device 110 may communicate with one another via the wired connection 1080 when the sensor hub 1010 and medical device 110 are physically coupled and/or decoupled. As illustrated in FIGS. 12 and 13, in various implementations, the sensor hub 1010 may be configured to communicatively couple via a network connection 1295 with one or more remote computing devices 1290. The remote computing devices may include a server and other devices communicatively coupled via the server through the network 1295 such as a personal computer, laptop, tablet, mobile device, and/or other medical devices. In this manner, the sensor hub 1010 may enable telemedicine and remote data viewing, analysis, storage, and/or sharing.

The sensor hub 1010 may include a housing 1012 (e.g., a second housing or a sensor hub housing). The housing 1012 may include one or more mating mechanisms 1045 configured to removably couple the sensor hub 1010 to the sensor hub connector 1040. The sensor hub 1010 further includes at least one DI port 1098 coupled to the housing 1012. The at least one DI port 1098 may be an SS-DI port (e.g., the SS-DI port 498a, 498b) or an SA-DI port (e.g., the port 298, 298a, 298b). The at least one DI port 1098 is configured to couple to a data transfer cable and a sensor (e.g., the data transfer cable 210 and sensor 220 for the SA-DI port) and configured to receive sensor data. The sensor hub 1010 further includes a sensor hub processor 1050 (e.g., a second processor), a sensor hub memory 1052 (e.g., a second memory), and a sensor hub communications interface 1054 (e.g., a second communications interface). The at least one DI port 1098 is communicatively coupled to the sensor hub processor 1050. The sensor hub processor 1050 is configured to receive sensor data via the at least one DI port 1098 and send the sensor data to the sensor hub communications interface 1054. In an implementation, the sensor hub processor 1050 is configured to store the sensor data in the sensor hub memory 1052. In an implementation, the sensor hub 1010 includes at least one universal serial bus (USB) port. In an implementation, the sensor hub 1010 may further include a sensor hub power source 1065. For example, the sensor hub power source 1065 may include one or more batteries configured to provide power to the sensor hub 1010 independently from power provided to the sensor hub 1010 by the medical device 110. In an implementation, the one or more batteries may recharge using power from the medical device 110 when the sensor hub 1010 is physically connected to the medical device 110 with the sensor hub connector 1040 (e.g., via the electrical contacts 1070a and 1070b).

The sensor hub communications interface 1054 is configured to communicatively couple to the medical device communications interface 1034 and send the sensor data to the medical device processor 1036 via the medical device communications interface 1034. The medical device processor 1036 is configured to control the medical device display 150 to display a visual representation (e.g., a first visual representation) of the sensor data obtained via the sensor hub to a user.

In an implementation, the sensor hub communications interface 1054 and the medical device communications interface 1034 are configured to communicate with each other via wired and/or wireless communicative couplings. Referring to FIGS. 10 and 11, in an implementation, the communications interfaces 1054 and 1034 may communicate via a wired coupling (e.g., via the contacts 1070a and 1070b and/or the cable 1080) when the sensor hub 1010 is physically retained by the sensor hub connector 1040. Referring to FIGS. 12 and 13, the communications interfaces 1054 and 1034 may communicate via a wireless coupling 1075 when the sensor hub 1010 is decoupled from the sensor hub connector 1040. The sensor hub connector 1040 and the mating mechanism 1045 may be configured to physically couple the medical device 110 and the sensor hub 1010 such that the contacts 1070a and 1070b provide electrical and/or communicative connectivity.

Figure 14:
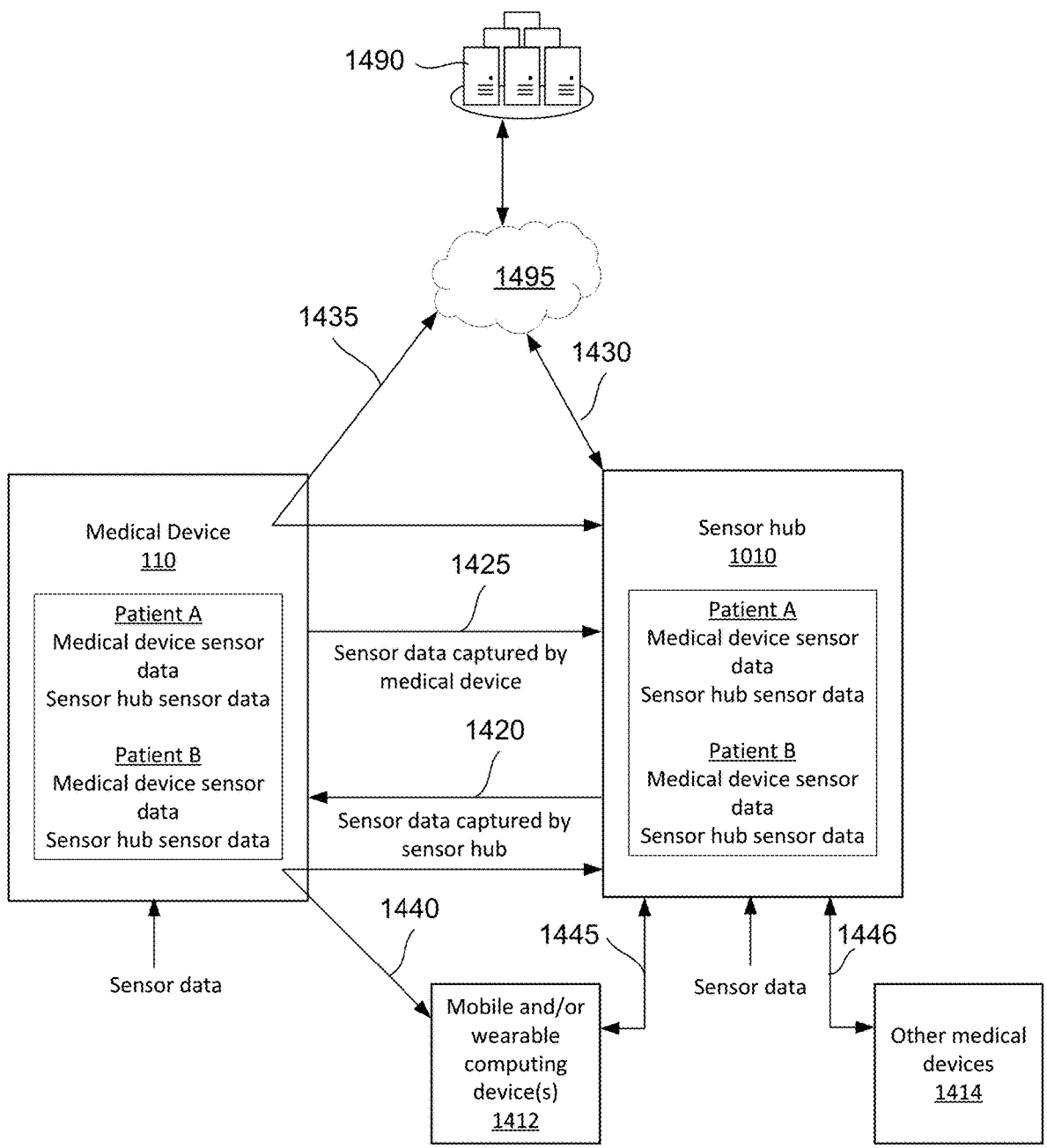
FIG. 14 shows a examples of various communications implementations for a sensor hub.

Referring to FIG. 14, examples of various communications implementations for the sensor hub are shown. The sensor hub 1010 may provide 1420 sensor data captured by the sensor hub 1010 to the medical device 110 when the sensor hub 1010 and the medical device 110 are physically coupled or physically uncoupled. Similarly, the medical device 110 may provide 1425 sensor data captured by the medical device 110 to the sensor hub when the sensor hub 1010 and the medical device 110 are physically coupled or physically uncoupled. As described above, the sensor hub 1010 and the medical device 110 may provide data to one another via communicative coupling between the sensor hub communications interface 1054 and the medical device communications interface 1034. This data communication may be via a wired connection (e.g., contacts 1070a, 1070b and/or cable 1080) and/or via a wireless connection 1075. As illustrated schematically in FIG. 14, in an implementation, the medical device 110 is configured to associate sensor data for a first patient (e.g., Patient A) that is received via the sensor hub 1010 with sensor data for the same patient (e.g., also Patient A) that is received via the medical device. The medical device 110 is configured to associate sensor data for a second patient (e.g., Patient B) that is received via the sensor hub 1010 with sensor data for the same patient (e.g., also Patient B) that is received via the medical device. Similarly, in an implementation, the sensor hub 1010 is configured to associate sensor data for a first patient (e.g., Patient A) that is received via the sensor hub 1010 with sensor data for the same patient (e.g., also Patient A) that is received via the medical device. The sensor hub 1010 is configured to associate sensor data for a second patient (e.g., Patient B) that is received via the sensor hub 1010 with sensor data for the same patient (e.g., also Patient B) that is received via the medical device 110.

In an implementation, the sensor hub 1010 and the medical device 110 may exchange authentication messages during or to initiate a communicative coupling. In this way, the two devices may verify that the sensor hub 1010 is recognized and compatible with the medical device 110. Further, the authentication may include an information exchange to verify that the medical device 110 and the sensor hub 1010 are associated with the same patient during a patient treatment.

In various implementations, the sensor hub 1010 may communicatively couple with other computing devices via a network 1495. For example, the sensor hub 1010 may communicate with a remote server 1490 via the communicative coupling 1430 and the sensor hub communications interface 1054. In an implementation, the remote server 1490 may be associated with a medical provider (e.g., a hospital, a physician's office, a medical records office, an emergency services office, an emergency services vehicle, a dispatch center, etc.). The communicative coupling 1430 may exist in the absence of an existing communicative coupling between the remote server 1490 and/or the network 1495 with the medical device 110. As another example, the sensor hub 1010 may communicate with the remote server 1490 via communicative coupling 1435 and the medical device 110. As a further example, the sensor hub 1010 may communicate with one or more mobile and/or wearable computing device(s) 1412 via the communicative coupling 1445. The communicative coupling 1445 may exist in the absence of an existing communicative coupling between mobile and/or wearable computing device(s) 1412 with the medical device 110. The mobile and/or wearable computing device(s) 1412 may include one or more of a tablet, a smartphone, a watch, a heads-up display, a laptop computer, and combinations thereof.

In an implementation, the sensor hub 1010 may communicate with the mobile and/or wearable computing device(s) 1412 via the communicative coupling 1440 and the medical device 110. The sensor hub 1010 and/or the medical device 110 may communicatively couple to the mobile and/or wearable computing device(s) 1412 via a short range wired or wireless coupling (e.g., Bluetooth®, Zigbee®, near-field communication device) or via the network 1495. The network 1495 may be a computer network (e.g., an Internet Protocol (IP) network, a cellular communications network, a satellite network, and combinations thereof. Communications between devices proximate to one another (e.g., on-scene devices) may be via a local area network, an ad hoc network, a mesh network, etc. and include coupling via radio frequency transmissions. Communications between devices in FIG. 14 may be encrypted and/or may include secure and/or authenticated communications.

As a further example, the sensor hub 1010 may communicate with one or more medical devices 1414 other than the medical device 110 via the communicative coupling 1446. The communicative coupling 1446 may exist in the absence of an existing communicative coupling between medical devices 1414 and the medical device 110. The medical devices 1414 may include one or more of a patient monitor, a defibrillator, a monitor/defibrillator, a wearable defibrillator, a compression delivery device, a ventilation device, a first aid kit, a compression monitor, an airway flow sensor, a bag valve mask, and/or another medical device configured to monitor and/or deliver therapy to a patient. In an implementation, the medical device 110 may be a first monitor/defibrillator and the other medical devices 1414 may include a second monitor/defibrillator. In an implementation, the sensor hub 1010 may be configured to communicatively couple with only one monitor/defibrillator during treatment of a patient but with one or more monitor/defibrillators outside of an ongoing patient treatment.

In an implementation, the sensor hub 1010 is configured to send one or more of sensor data, a patient case file, device readiness data, and device status data to one or more of the communicatively coupled devices illustrated in FIG. 14. Additionally or alternatively, the sensor hub 1010 is configured to receive one or more of sensor data, software, software updates, settings, settings updates, protocols, and protocol updates from one or more of the communicatively coupled devices illustrated in FIG. 14.

Figure 15:
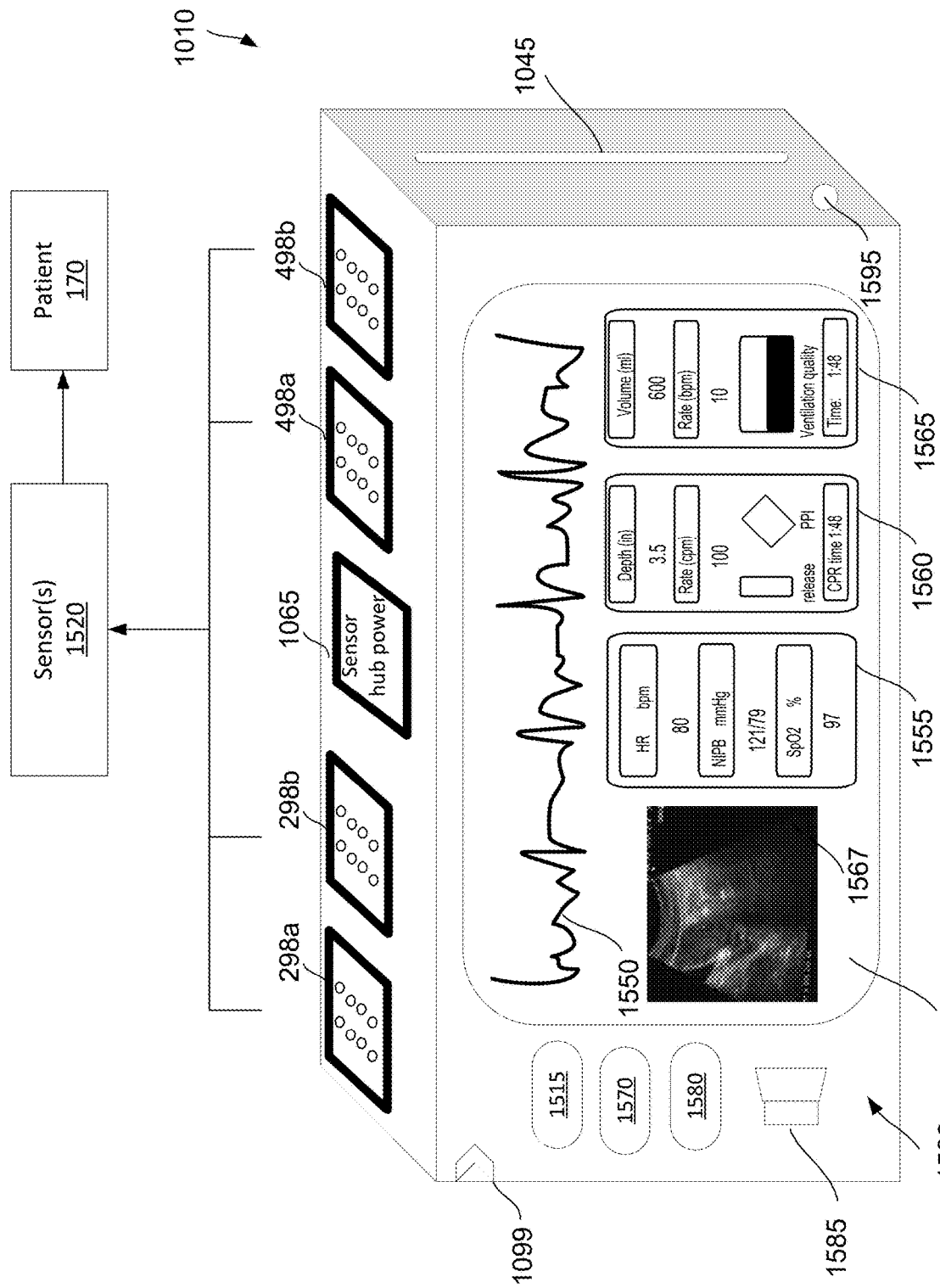
FIG. 15 shows a schematic diagram of an example of a sensor hub.

Referring to FIG. 15, a schematic diagram of an example of a sensor hub is shown. The features of the sensor hub 1010 shown in FIG. 15 are examples only and not limiting of the disclosure. In various implementations, the sensor hub 1010 may include one or more of these features. Further, the quantity of each feature shown is an example only and not limiting of the disclosure.

In an implementation, the sensor hub 1010 may include one or more DI ports. The one or more DI ports include one or more SA-DI ports (e.g., the ports 298a and 298b). Additionally or alternatively, the one or more DI ports may include one or more SS-DI ports (e.g., the ports 498a and 498b) and/or one or more USB ports 1099. The sensor hub 1010 may couple to one or more sensors 1520 via the one or more DI ports. Each sensor may be configured to couple with an SA-DI port and/or an SS-DI port. The SA-DI ports may couple to a sensor via the data transfer cable 210. The SS-DI ports may couple to a sensor via a cable compatible with the SS-DI port and the respective sensor. The sensors 1520 may include one or more of an ECG sensor, a pulse oximetry sensor, a capnography sensor, a heart rate sensor, an IBP sensor, an NIBP sensor, a temperature sensor, an airway flow sensor, a CPR compression sensor, end tidal carbon dioxide (e.g., $EtCO_2$) sensor, Near Infrared Spectroscopy (NIRS) sensor, an ultrasound sensor, spirometer, pneumotachometer, pressure sensors, and combinations thereof. Although the DI ports in FIG. 15 are similar in appearance, as illustrated in FIG. 15 for simplicity, the DI ports may be configured with different shapes, types and number of electrical contacts, colors, etc. to differentiate between the DI ports for usability and for compatibility with sensor data and respective sensor cables.

Figure 16:
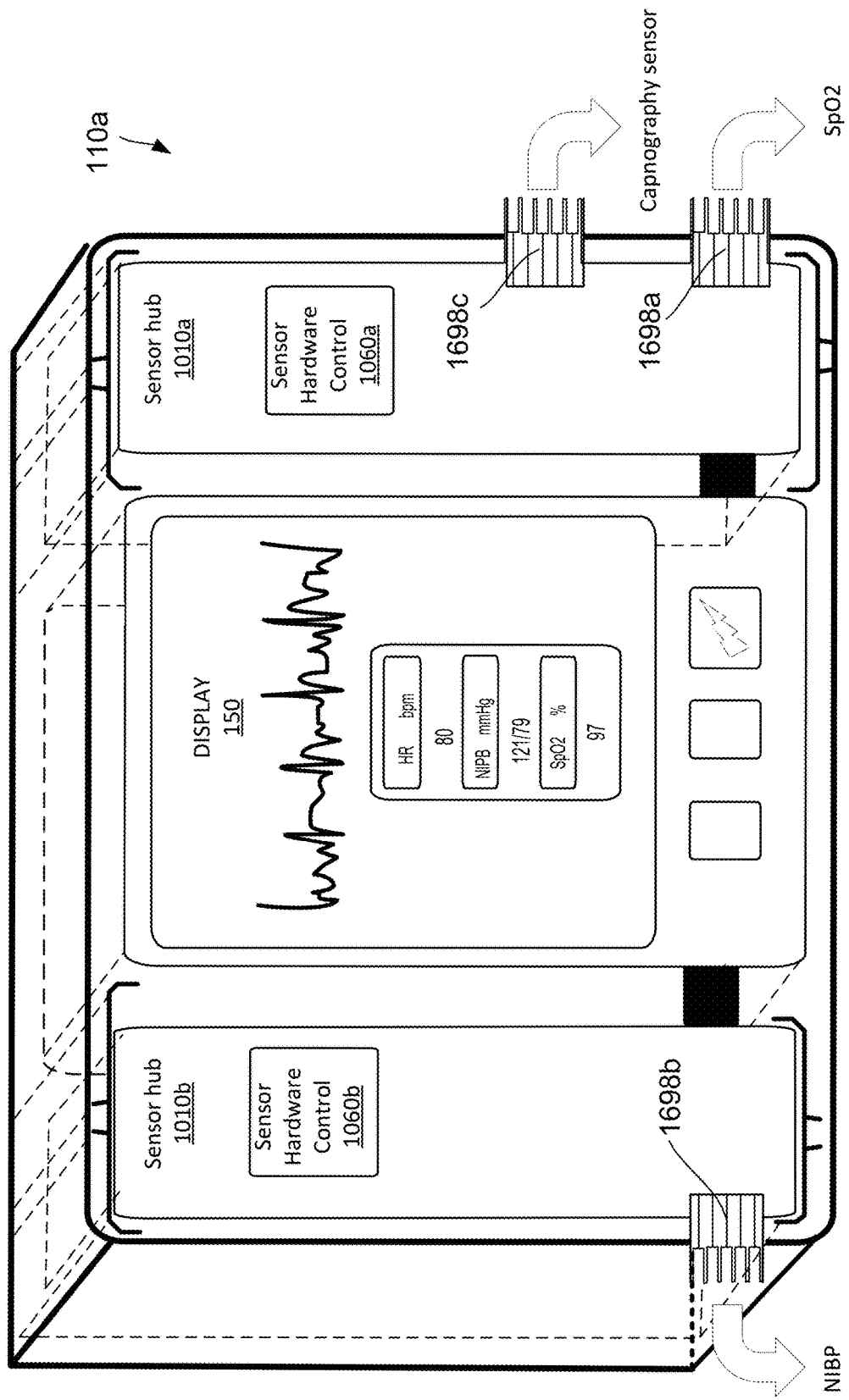
FIG. 16 shows a schematic diagram of an exemplary medical device transfer cable system with a multiple removable sensor hubs coupled inside of the defibrillator housing.

Referring to FIG. 16, with further reference to FIGS. 10 and 11, the medical device 110 may include one or more sensor hubs. Each sensor hub may include sensor hardware control 1060 (e.g., as shown in FIGS. 10 and 11). The sensor hardware control 1060 may be tailored to a specific sensor or set of sensors. For example, the medical device 110a shown in FIG. 16 is an example of the medical device 110 that includes two sensor hubs 1010a and 1010b. Each sensor hub 1010a and 1010b may include sensor hardware control 1060a and 1060b, respectively, tailored to one or more specific sensors configured to couple to the sensor hub via the DI ports 1698a, 1698b, or 1698c. The quantity of DI ports and sensors associated with the DI ports in FIG. 16 are examples only and not limiting of the disclosure. Each sensor hub 1010a and 1010b may include one or more DI ports. The display 150 may provide visual representations of data from all of the sensor hubs coupled to the medical device 110a.

As an example, in an implementation, the sensor hub 1010a may include hardware control 1060a for side stream capnography. Further, this sensor hub 1010a may be configured with two DI ports 1698a and 1698c. In an example, the DI port 1698a connect to an SpO2 sensor and the DI port 1698c may connect to a capnography sensor. The DI ports 1698a and 1698c may be SA-DI ports with software/API appropriate for sensor data form SpO2 and capnography. The DI port 1698b may connect to an NIBP sensor and the sensor hardware control 1060b may include a pneumatic pump system for NIBP. These modular sensor hubs may be independently serviceable and replaceable and may enable the manufacturer and the customer to tailor the medical device 110 to sensor capabilities and combinations according to specific customer needs.

Referring again to FIG. 15, when the sensor hub 1010 is physically coupled to the medical device 110, the sensor hub 1010 may receive power from the medical device 110. For example, the sensor hub 1010 may receive power via the contacts 1070a, 1070b and/or the wired connection 1080 or via a wireless power transmission from the medical device 110 and the sensor hub 1010. In an implementation, the sensor hub connector 1040 and the mating mechanism 1045 may provide power transmission from the medical device 110 to the sensor hub 1010. In addition to or as an alternative to power transmission from the medical device 110, the sensor hub 1010 may include a sensor hub power source 1065, for example one or more batteries. The batteries may provide power to the sensor hub 1010 when the sensor hub 1010 is physically coupled to the medical device 110, physically decoupled from the medical device 110, or both. The sensor hub may include a power control 1515 to power on/power off the sensor hub when the sensor hub is physically decoupled from the medical device 110. In an implementation, control of power provision to the sensor hub 1010 when physically coupled to the medical device 110 may be via the power control 1515 and/or via the power control 436 for the medical device 110 (e.g., as shown in FIG. 4).

In an implementation, the sensor hub 1010 may include a user interface 1530. The user interface 1530 may include a display 1540 configured to provide visual representation(s) of data from the sensor(s) 1520 in real-time during ongoing patient care. The visual representations may provide the data as graphical and/or textual data. The visual representations may include waveform data 1550. The waveform data 1550 may include, for example, but not limited to ECG, pulse oximetry, and/or capnography. The visual representations may include discrete numerical data 1555. The discrete numerical data may include, for example, but not limited to blood pressure (NIBP, IBP) heart rate, an instantaneous pulse oximetry value and/or an instantaneous capnography value. Additionally or alternatively, the visual representations may include or provide caregiver feedback, for example, CPR feedback 1560 and/or ventilation feedback 1565. The CPR feedback may include, for example, compression depth, compression rate, compression time, compression release, and/or perfusion performance. This display 1540 may provide the CPR feedback in real-time on a compression by compression basis. The ventilation feedback may include, for example, gas volume, ventilation rate, ventilation quality, and/or ventilation time. In an implementation, the ventilation feedback may be bag valve mask feedback. The visual representations may further include image data, for example, but not limited to, laryngoscopy and/or ultrasound images. The ultrasound images may include ultrasound images of a patient's tendons, muscles, joints, internal organs, skeletal structures, abdomen and/or the patient's heart, blood vessels, carotid artery, and/or other components of the cardiovascular system. The visual representations may be part of a guided medical intervention such as biopsies, tissue or fluid samples, and/or other diagnostic or invasive procedures.

The user interface 1530 may include alarm control(s) 1570 and/or data entry control(s) 1580. In an implementation, the display 1540 may be a touchscreen display configured to accept tactile input. The sensor hub may further include a speaker/microphone 1585 configured to receive audio input and provide audio output. In an implementation, the sensor hub 1010 may include at least one user input device port 1595. The port(s) 1595 may receive user input from a user input device such as, for example, a mouse, a keyboard, a remote control, a tablet, a smartphone, a wearable device (e.g., a headset, glasses, earpiece, watch, etc.), etc. The port(s) 1585 may couple to the user input device(s) via wired or wireless connections. The sensor hub 1010 may also include a haptic output device 1590. The haptic output device 1590, the display 1540, and/or the speaker/microphone 1585 may provide user feedback, alarms and/or confirmation of data entry and/or sensor connection. The user interface 1530 may further include one or more soft key controls. In various implementation, the user interface 1530 may provide feedback and/or instructions as text, graphics, animation, video (e.g., live, stream or pre-recorded), chat and/or text messages (e.g., via the network 1495), or combinations thereof.

In an implementation, in response to connection or disconnection of a sensor 1520 from the sensor hub 1010, one or more of the output devices 1590, 1540, and 1585 may provide a tactile signal, audio signal or visual signal that indicates the connection/disconnection and/or the type of sensor that has been connected or disconnected.

Referring to FIGS. 17A-17D, schematic diagrams of examples of a respiratory distress (RD) hub are shown. The RD hub is a respiratory distress system that includes a portable ventilator along with ventilation sensors, sensor controls, and ventilation data analysis engines. The features of the RD hubs 1710, 1710a, 1710b, 1710c and 1710b as shown in FIGS. 17A-17D are examples only and not limiting of the disclosure. In various implementations, the RD hubs may include one or more of these features. Further, the quantity of each feature shown is an example only and not limiting of the disclosure.

Figure 17A:
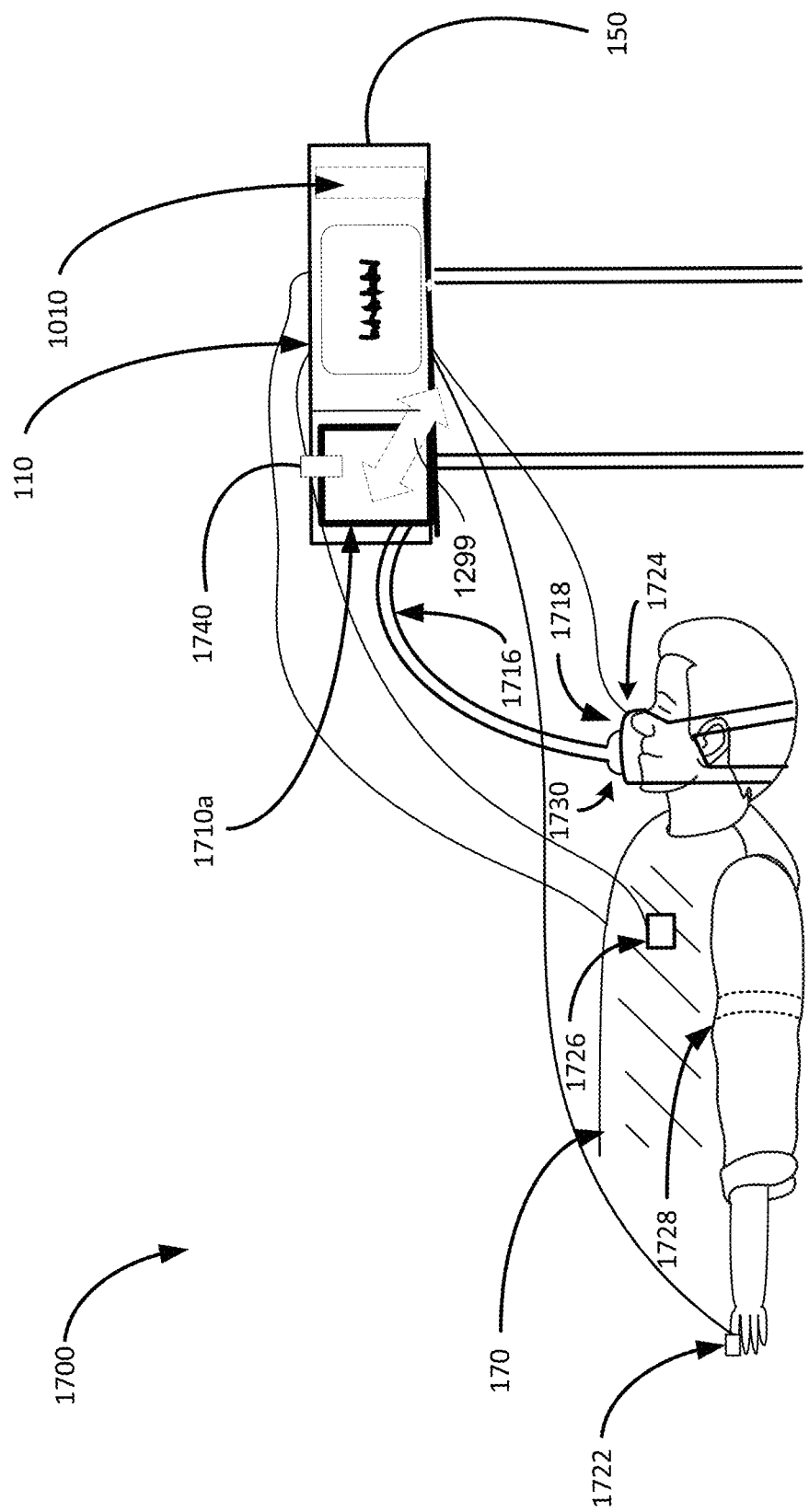
FIGS. 17A-17C show schematic diagrams of examples of respiratory distress hub configurations.
Figure 17B:
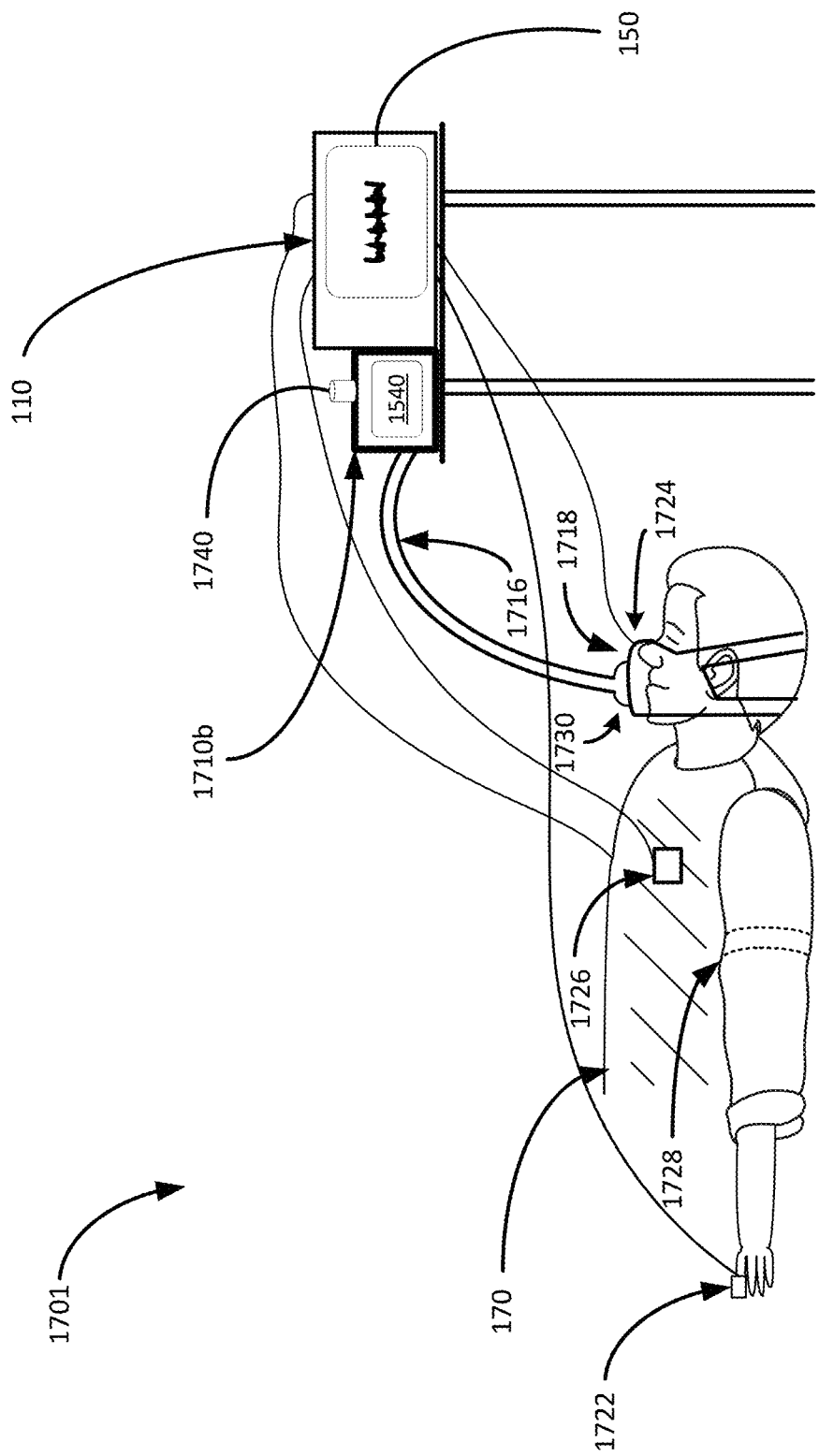
Figure 17C:
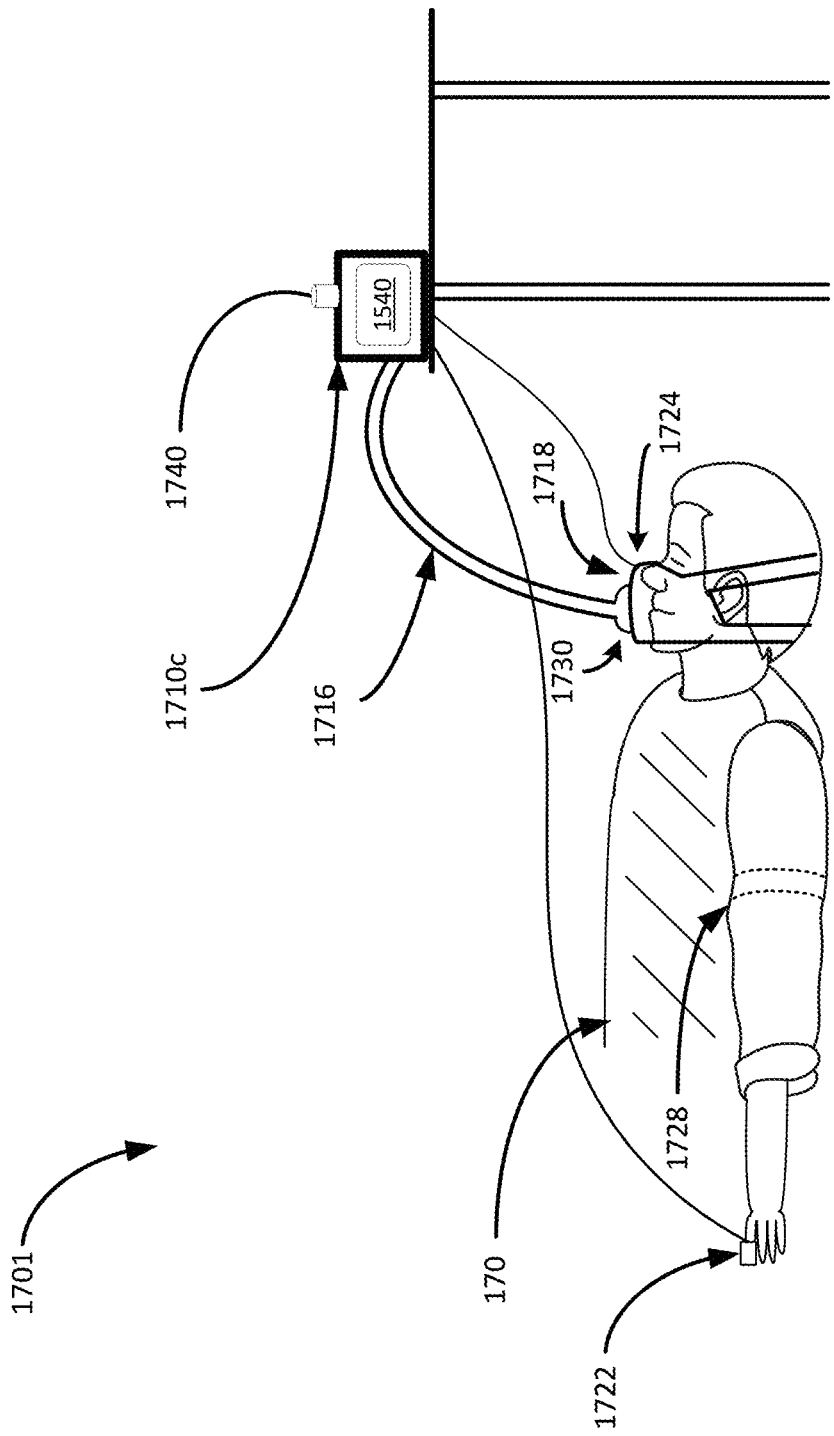
Figure 17D:
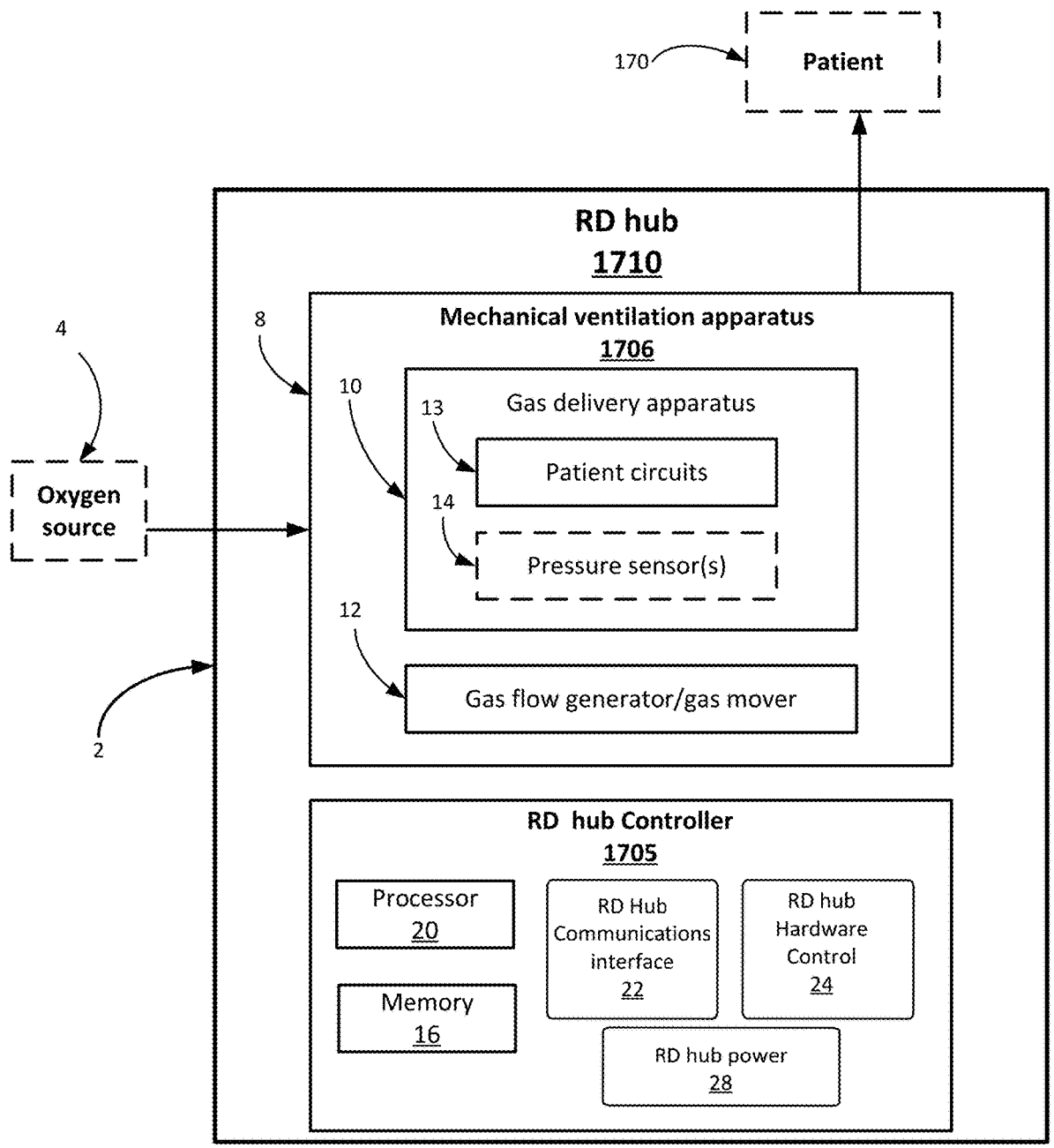
FIGS. 17D-17E show schematic diagrams of examples of components of a respiratory distress hub.
Figure 17E:
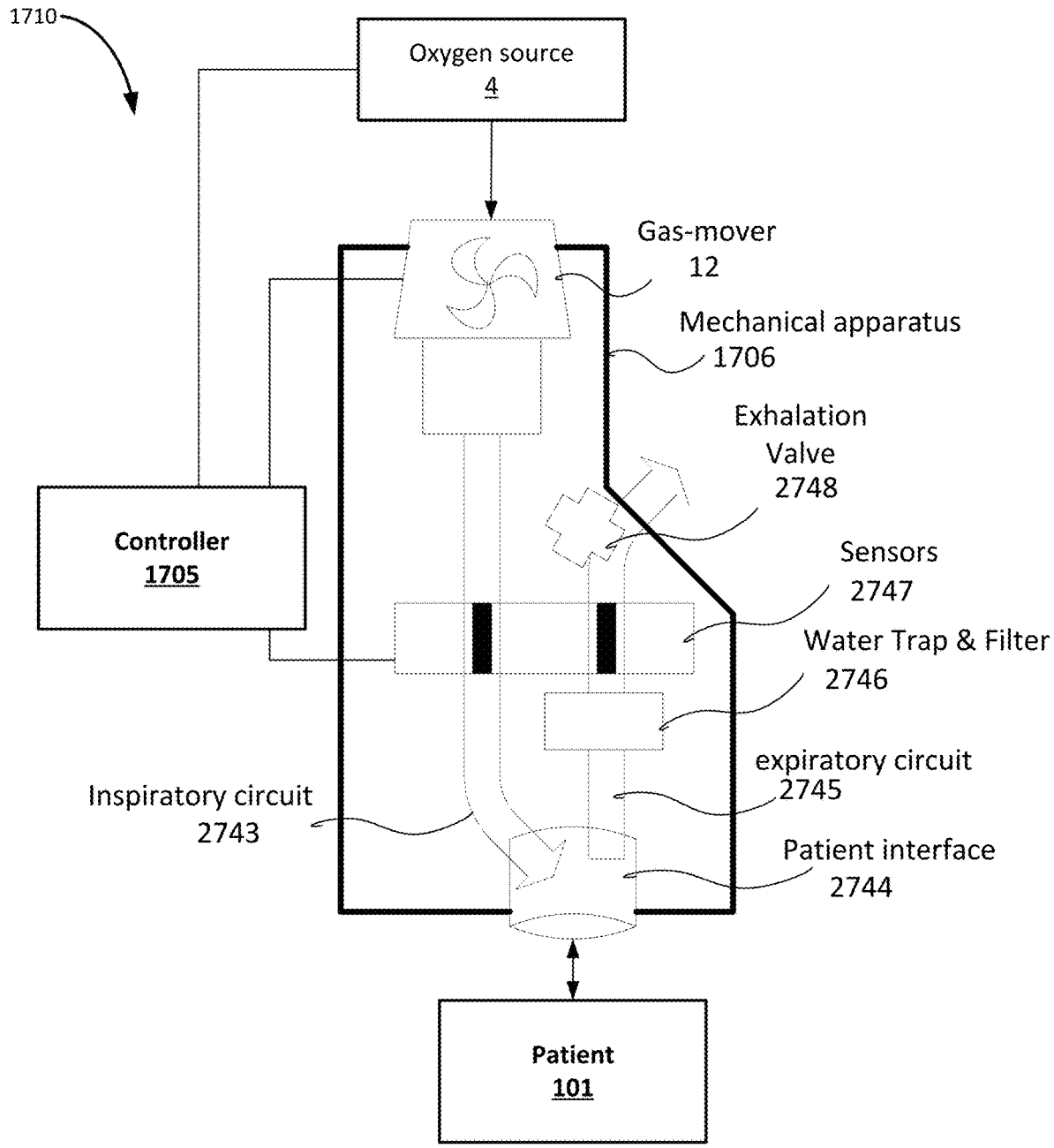

As shown in FIG. 17A, the RD hub 1710a is an example of the removable sensor hub 1010, 1010a, 1010b that may couple to the interior of the housing of the medical device 110 (e.g., as shown FIGS. 10, 12, 14, and 16). The RD hub 1710a may insert into or release from (e.g., as shown by the arrow 1299) the interior of the housing. As shown in FIG. 17B, the RD hub 1710b is an example of the removable sensor hub 1010 that may couple to the exterior of the housing of the medical device 110 (e.g., as shown in FIGS. 11, 13, 14, and 15). As shown in FIG. 17C, the RD hub 1710c is an example of the sensor hub 1710b in use separately from the medical device 110. Additionally, the RD hubs 1710 shown in FIGS. 17D and 17E are schematic diagrams of an example of at least a portion of the components of any of the hubs 1710a, 1710b, or 1710c.

FIG. 17A illustrates an example emergency care environment 1700 including a RD hub 1710a coupled to the interior of the housing of the medical device 150. Similarly, FIG. 17B illustrates the emergency care environment 1701 with the RD hub 1710b coupled to the exterior of the housing of the medical device 150 and FIG. 17C illustrate the emergency care environment 1702 with the RD hub 1710c operating independently from the medical device 110. When delivering mechanical ventilation, the RD hub 1710a, 1710b, and/or 1710c may provide breathing gas to a patient 170 via a mechanical ventilation apparatus 1706 including a gas flow generator (such as a blower, turbine or compressor, or device based thereon) and a gas delivery apparatus including a patient circuit 1716 that includes a facemask 1718. However, in some embodiments, ventilation may be provided via intubation rather than via a facemask 1718.

In the examples depicted in FIGS. 17A and 17B, the medical device 150 and/or the RD hub may include one or more of a pulse oximeter 1722 for measuring patient SpO2, a capnographic sensor 1724, which may be used in measuring EtCO2, a blood pressure sensor/monitor 1728, and may include various other components such as one or more flow sensors, pressure sensors, airway sensors, spirometers or pneumotachometers. Optionally, one or more of these sensors may be included in and/or coupled to one or more other sensor hubs 1010 as described above. The medical device 110 may further provide electrodes 1726 that may be used in providing electrotherapy to the patient 170. In the example of FIG. 17C, the RD hub 1710c may include one or more of the pulse oximeter 1722 for measuring patient SpO2, the capnographic sensor 1724, which may be used in measuring EtCO2, the blood pressure sensor/monitor 1728, and may include various other components such as one or more flow sensors, pressure sensors, airway sensors, spirometers or pneumotachometers.

The RD hub (1710a, 1710b, and/or 1710c) may be coupled with a supplemental oxygen (02) source. In various embodiments, the RD hub (1710a, 1710b, and/or 1710c) may be capable of supplying oxygen, using the supplemental oxygen source, in a number of different ways, or the RD hub (1710a, 1710b, and/or 1710c) may be capable of supplying oxygen in any one of several different ways. In various embodiments, the manner in which oxygen is supplied may be determined without user selection, or may be selected by a user, and may or may not require user confirmation.

In some embodiments, a reservoir bag may be used that allows entrainment of oxygen from an oxygen source. For example, a user may adjust the flow rate of delivered oxygen based at least in part on current SpO2, which may be monitored by one or more of the devices 1702, 1704, 1708. The medical device 110 or the RD hub (1710a, 1710b, and/or 1710c) may continuously monitor the SpO2. In various embodiments, current SpO2 may be displayed for viewing by the user via a medical device display 150 or the hub display 1540.

In some embodiments, the RD hub (1710a, 1710b, and/or 1710c) includes and uses a variable output regulatory valve 1740, in which an oxygen output rate allowed or facilitated by the variable output regulatory valve 1740 may be varied and changed to a particular oxygen flow rate of a range of possible oxygen flow rates. The variable output regulatory valve 1740 may be used in providing a variable and controllable oxygen flow rate for gas provided by the RD hub (1710a, 1710b, and/or 1710c) during the providing of mechanical ventilation. In an implementation, the variable output regulatory valve 1740 may attach to a gas inlet of the RD hub (1710a, 1710b, and/or 1710c), a high pressure oxygen source, and may attach to the medical device 110 (to monitor SpO2), for example.

In some embodiments, the variable output regulatory valve 1740 may be controlled automatically or without need for user interaction. For example, this may be based at least in part on the patient's continuously monitored SpO2 and in accordance with an fraction of inspired oxygen (FiO2) setting or adjustment that may be determined based at least in part on the current SpO2. In some embodiments, this arrangement may be used in providing closed loop control (CLC) of FiO2 (FiO2 CLC). In some embodiments, a portable oxygen concentrator (POC) may be used. FiO2 CLC may be used in controlling and regulating the output of the POC for entrainment of oxygen into the RD hub (1710a, 1710b, and/or 1710c) to be used in gas delivered by the RD hub (1710a, 1710b, and/or 1710c) during mechanical ventilation. Furthermore, in some embodiments, including embodiments in which the variable output regulatory valve 1740 or a POC is used, CLC of positive end expiratory pressure (PEEP) (PEEP CLC) may also be included in control of the portable ventilator or RDM 1704. In some embodiments, PEEP CLC may be based least in part on a current fraction of inspired oxygen (FiO2) setting and a current PEEP setting. In various embodiments, control with FiO2 CLC and/or PEEP CLC may be provided internally by the RD hub (1710a, 1710b, and/or 1710c) or by the medical device 110.

In some embodiments, the RD hub (1710a, 1710b, and/or 1710c) may operate, or may have one or more modes of operation, that do not include, or at times or during certain periods of time do not include, delivering mechanical ventilation. Furthermore, the RD hub (1710a, 1710b, and/or 1710c) may include operation, or modes of operation, for use outside of an emergency care context. For example, in some embodiments, the RD hub (1710a, 1710b, and/or 1710c) may include a spirometer that can be used for patient respiratory assessment outside of an emergency care situation. For example, such assessment may be performed on patients or individuals that may not be presently receiving mechanical ventilation, may not require mechanical ventilation, and may not be presently experiencing RD. In some embodiments, such assessments may include, for example, respiratory parameter and respiratory status assessments on a patient during a routine, scheduled or other doctor's office, or medical facility or hospital. Furthermore, some assessments may be made while the patient is be laying, sitting or standing, and while the patient is not experiencing RD.

The RD hub (1710a, 1710b, and/or 1710c) may include one or more pressure sensors and/or pneumotachometers 1730, which may be disposed within the patient circuit 1716, for sensing signals representative of gas flow within the gas delivery apparatus of the RD hub (1710a, 1710b, and/or 1710c). In embodiments, the one or more pressure sensors and/or pneumotachometers 1730 may be coupled with or part of one or more spirometers, for example. In some embodiments, a controller (e.g., the controller 1705 shown in FIG. 17D) of the RD hub (1710a, 1710b, and/or 1710c) receives the signals representative of the gas flow. Based at least in part on the signals representative of the gas flow, the controller may generate respiratory parameter data corresponding with at least one respiratory parameter of the patient, such as, for example, total compliance (Crs), total resistance (Rrs), volume control (VC), forced vital capacity (FVC), forced expiratory volume (FEV) at various timed ventilation intervals (e.g., FEV1, FEF, or FEF25-75, PEF, PEFR, MVV, etc.).

The controller may transmit or provide the respiratory data to be received to the medical device 110, such as for use in determining a respiratory status of the patient. However, in some embodiments, the RD hub (1710a, 1710b, and/or 1710c) may determine, or participate in determining, the respiratory status of the patient.

In some embodiments, aspects of a medical device system including the medical device 110 and the RD hub (1710a, 1710b, and/or 1710c), such as distribution and integration of roles between the devices as well as aspects of particular devices, may be optimized based on factors that may include a desired degree of portability or ease of operation of the RD hub (1710a, 1710b, and/or 1710c), for example. In an embodiment, the RD hub 1710c may communicate with a remote medical device 110 and/or the remote medical device or another computing device may provide remote control of the RD hub 1710c. Therefore distribution and integration of roles may occur via bidirectional communications between the linked devices. Furthermore, aspects of individual devices may be optimized. Such aspects may include, for example, sets of controls, processing and memory aspects, software, algorithms, and context sensitive guidance or clinical decision support related aspects. In some embodiments, various capabilities may be included with the RD hub (1710a, 1710b, and/or 1710c), or included with one or more other devices or systems, or may be distributed or integrated between them. This may include, for example, processors, memories, controllers, or stored software or algorithms. These capabilities may be used, for example, in processing signals, generating respiratory parameter data or determining a respiratory status of the patient. They may also be used in performing coordination or integration between devices. As such, in this and other ways, the roles and processing capability and components of the RD hub (1710a, 1710b, and/or 1710c) may be greater or fewer, or determined or allocated, based at least in part on the roles of one or more other devices in an environment. In some embodiments, reducing or limiting the roles, processing capability or components of the RD hub (1710a, 1710b, and/or 1710c) can increase or improve the portability or portable practicality of the RD hub, such as by allowing reduced RDM size, weight, complexity, bulk, footprint, or noise during operation, for example. This, in turn, can allow for various implementations that may be balanced or optimized for particular anticipated or likely scenarios, which can increase positive, potentially life-saving patient outcomes.

FIG. 17D shows a schematic diagram of an RD hub 1710. The RD hub 1710 shows exemplary components of the RD hubs 1710a, 1710b, and 1710c as described above. Further, the RD hub 1710 is an example of the sensor hub 1010 as described above in FIGS. 10-16.

In an implementation, the RD hub 1710 may be tailored to specific sensors, i.e., respiratory distress sensors, as an example of the specialized hub described in FIG. 16. For example, the RD hub 1710 may include sensors configured to or capable of sensing signals representative of gas flow that can be used in determining at least one patient respiratory parameter, such as may include use or one or more pressure sensors 14, pneumotachometers or spirometers, that may, in some embodiments, be included as part of, or within or partially within, the mechanical ventilation apparatus 8. In various embodiments, one or more spirometers may be included within the RD hub 1710 and/or may be coupled with the RD hub 1710. Although depicted in a separate box from the patient circuits 13, it is to be understood that the pressure sensors 14 and/or other components such as pneumotachometers or spirometers, may be included within or partially within the patient circuits 13, such as a patient inspiratory circuit and/or a patient expiratory circuit. In some embodiments, the pressure sensor(s) 14 and other associated components may be used in sensing or obtaining respiratory parameter data, which respiratory parameter data may be used in determining or generating a respiratory status (which can include associated data). The respiratory parameter data and respiratory status data may also be used in connection with control of operation of the RD hub 1710, such as in control of mechanical ventilation providing by the RD hub 1710, whether such control is internally provided by the RD hub 1710, remotely provided, or with aspects of both.

Alternatively, the RD hub 1710 may include the respiratory distress sensors with other sensors not directly targeted to respiratory distress indicators of parameters. For example, the RD hub 1710 may include the RD sensors described above along with one or more of an ECG sensor, a heart rate sensor, an IBP sensor, an NIBP sensor, a temperature sensor, a CPR compression sensor, Near Infrared Spectroscopy (NIRS) sensor, an ultrasound sensor, and combinations thereof.

The RD hub 1710 includes a mechanical ventilation apparatus 8 and includes at least one controller 1705. The controller 1705 includes at least one processor 20 (e.g., the sensor hub processor 1050 as described above) and at least one memory 16 (e.g., the sensor hub memory 1052 as described above) for storing data, and may also include software that may be stored in the at least one memory 16. The controller 1705 of the RD hub 1710 is an example of the sensor hub 1010. As such, the controller 1705 may also include an RD hub communications interface 22 (e.g., the sensor hub communications interface 1054 as described above), an RD hub hardware control 24 (e.g., the sensor hardware control 1060 as described above), and RD hub power 28 (e.g., the sensor hub power 1065 as described above). The RD hub 1710 may include or be connected to an oxygen source 4.

Referring to FIG. 17E, an example of the mechanical ventilation apparatus for a ventilation system is illustrated. The mechanical ventilation apparatus 2740 may include the gas-mover 12 configured to move oxygen from the oxygen source 4 through an inspiratory circuit 2743 to the patient 101 via a patient interface 2744. The ventilation system 280 may use the gas-mover 12 to provide a range of therapeutic ventilation modalities to provide various interventions. These various interventions may include 1) noninvasive ventilation (NIV) including continuous positive airway pressure (CPAP) and bilevel ventilation (bilevel); 2) high-flow nasal cannula (HFNC); 3) invasive ventilation (IV) using assist/control (AC), synchronized intermittent mandatory ventilation (SIMV) and pressure support (PS) modes; and 4) synchronized ventilation during cardiopulmonary resuscitation (CPR) mode.

The RD hub 1710 may provide ventilation during CPR, and may, for example work in coupling and integrating with one or more critical care monitors, such as one or more patient monitor/defibrillator(s) 110, for example. In some embodiments, for example, during mask ventilation, unprotected airway, the RD hub 1710 may deliver 2 breaths for every 30 compressions as measured by a monitor. In some embodiments, for example, when the airway is protected (e.g., endotracheal tube, Combitube, etc.), the RD hub 1710 may continuously deliver 10 breaths/min independent of the compression rate (asynchronous).

The patient interface 2744 may include an appropriate gas delivery device, such as an intubation tube, mask, nasal cannula, etc. The mechanical ventilation apparatus 2740 further includes an expiratory circuit 2745 and an exhalation valve 2748. Both the inspiratory and expiratory circuits include respiratory sensors 2747. The sensors 2747 may include, for example, but not limited to, a pneumotachometer, an airway pressure sensor, and a spirometer. The sensors 2747 enable the RD hub 1710 to measure the patient's respiratory efforts as well as the performance of the RD hub 1710 when providing mechanical respiratory assistance to the patient. The sensors 2747 may generate and provide data including but not limited to flow rate, tidal volume and minute ventilation, respiratory mechanics (e.g., resistance and compliance) and spirometry, and may include, for example, forced vital capacity (FVC), forced vital capacity at 1 second (FEV1) and peak expiratory flow rate (PEF or PEFR). In addition, the medical device 110 may provide, for example, capnography and/or oximetry data, such as oxyhemoglobin and carboxyhemoglobin saturation and mainstream or other capnographic data such as end tidal CO2 (EtCO2). This data may allow, for example, for calculation of CO2 elimination rate and volumetric capnography, by the RD hub 1710 and/or the medical device 110 which may include using flow data from the RD hub 1710.

In some embodiments, for patients who require supplemental oxygen (O2), the RD hub 1710 may provide a number of methods to support oxygenation by invasive and noninvasive ventilation. For example, one method may include using a small reservoir bag system that allows entrainment from an O2 flow source. In some embodiments, in a first method, the user may manage the O2 delivery to the patient while monitoring the oxygen saturation (SpO2) measured by the medical device 110. A second method may make use of an innovative smart O2 valve (SOV) or module, which may, for example, attach to the inspiratory circuit 2743, a high-pressure O2 cylinder/source and the medical device 110 This may, for example, provide for automatic control of the patient's oxygenation using physiologic closed loop control (PCLC) where, the SpO2 signal may be used to regulate the output of the SOV. A third method may provide for the functional integration of a portable O2 concentrator (POC), which may, for example, use PCLC to regulate the O2 output of the POC and the O2 entrainment into the RD hub 1710.

Figure 17F:
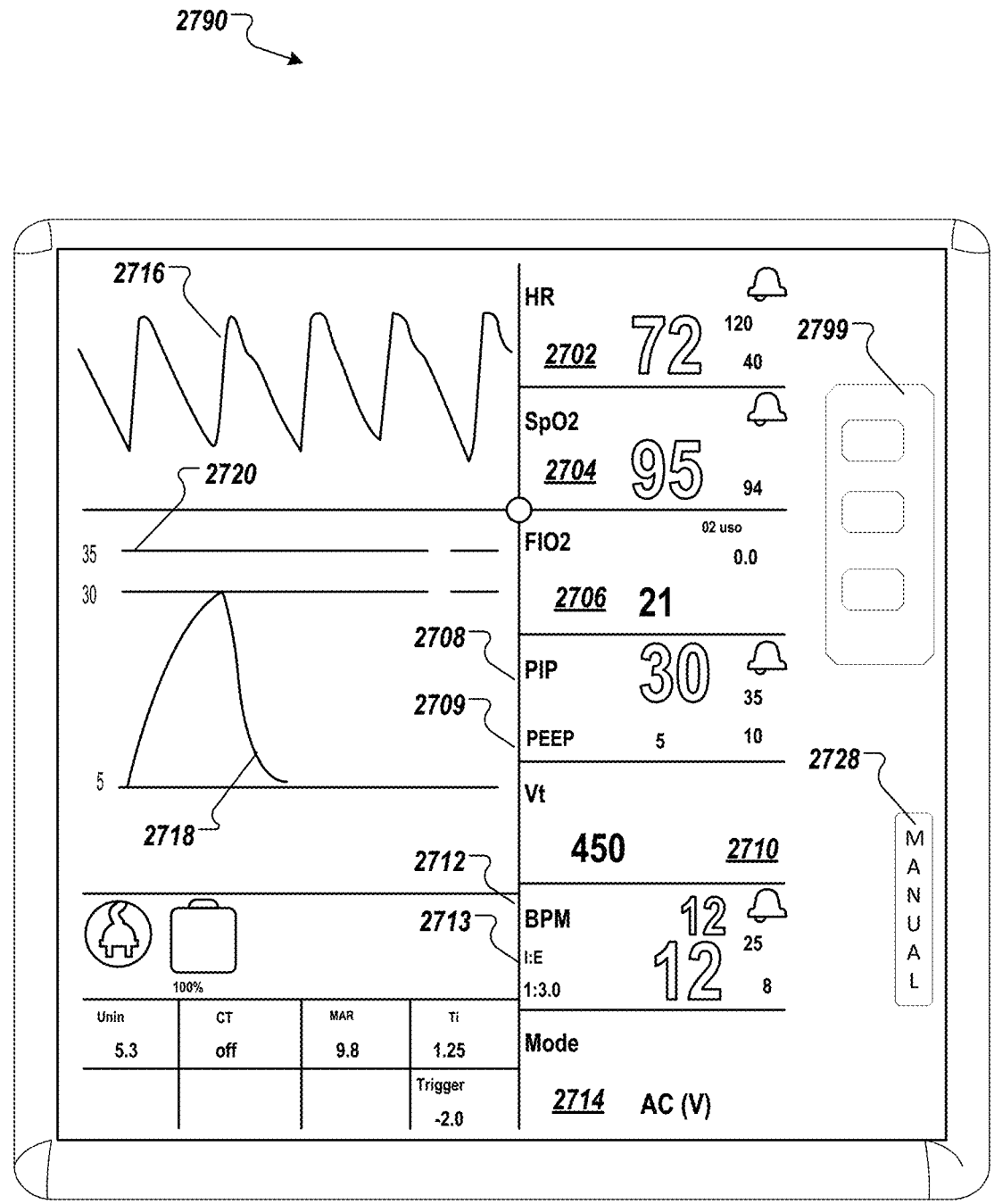
FIG. 17F shows an example of a display screen of a respiratory distress hub.

Referring to FIG. 17F, an example of user interface for a ventilation system is shown. In an implementation, the RD hub 1710b or 1710cb or 1710b or 1710cc may include the display screen 2790. The display screen 2790 may display data generated by the RD hub 1710b or 1710c and/or may include controls (e.g., soft-keys 2799) for user adjustment of ventilation parameters. In an implementation, the display screen 2790 may further include one or more features of the display 1540 as discussed above.

The data generated by the RD hub 1710b or 1710c that may be displayed at the screen 2790 and/or transmitted or provided to the medical device 110 for display at the screen 150, may include, for example, ventilation settings, ventilation parameters, and/or respiratory physiological parameters collected by the RD hub 1710b or 1710c. For instance, ventilation settings may include the respiratory rate (breaths per minute (BPM)) 2712, inspiratory:expiratory ratio (I.E, ratio of inspiratory time to expiratory time) 2713, tidal volume (volume of air delivered per breath) (Vt) 2710, positive end-expiratory pressure (PEEP), pressure in the lungs above atmospheric pressure that exists at the end of expiration) 2709, peak inspiratory pressure (PIP) limit 13708, fraction of inspired oxygen (FiO2) 2706, mode setting (e.g., assist/control (AC), synchronized intermittent mandatory ventilation (SIMV), continuous positive airway pressure (CPAP), bilevel (BL)) 2714, etc. In some examples, each of the ventilation settings 2704, 2706, 2708, 2709, 2710, and 2712/2713 may have a corresponding user input 2722a, 2722b, 2722c, 2722d, 2722e, 2722f, and 2722g on the ventilation system 280 for adjusting the respective setting 2704, 2706, 2708, 2709, 2710, and 2712/2713. Ventilation parameters may include, for example, inspiratory pressure data, expiratory pressure data, inspiratory flow data, expiratory flow data, leak detection, or other information measured from the RD hub 1710b or 1710c. Examples of respiratory physiological parameters may include non-continuous pulse oximeter (SpO2) measurements 2704, end-tidal CO2 (EtCO2) measurements, continuous SpO2 waveform data 2716, airway waveform data 2718, continuous CO2 waveform data, heart rate 2702, blood pressure, airway pressure data, airway flow data, spirometry data, amongst others.

In some examples, the RD hub 1710b or 1710c can be configured to generate alarm signals (e.g., visual and/or audible indications) when one or more parameter setpoints have been exceeded. In one example, when airway pressure exceeds a high airway pressure limit 2720, an alarm can be generated. The display screen 2790 and/or 150 may provide these alarms.

In some implementations, alarms generated by the RD hub 1710b or 1710c can include patient safety alarms such as high/low airway pressure, high/low tidal volume, high/low breath rate/apnea, PEEP leak, insufficient flow, spontaneous breath-PIP high/low, spontaneous breath-VT high/low, patient inspiratory demand not met, auto-PEEP, patient disconnect, exhalation system failure/fault, calibration error, suspicious triggers, tubing compliance faults, $SPO_2$ sensor off/low/error, heart rate high/low, etc. The RD hub 1710b or 1710c can also generate environmental alarms such as low battery, power faults, climatic environment faults, oxygen supply faults, gas intake faults, etc. Self-check alarms can include internal communication errors, pneumatic system failures, power system faults, pulse oximetry module faults, preventive maintenance alerts, etc. In some examples, when an alarm is generated, a pop-up message can be displayed at the RD hub interface 2790. In addition, one or more alarm setpoints can be adjustable by a user at the RD hub interface 2790. For example, alarm setpoints for airway pressure high/low, tidal volume high/low, breath rate, spontaneous breath, $SPO_2$ % low, and hear rate high/low can be manually adjusted by a device user. When an alarm signal is generated and/or when an alarm pop-up message is displayed at the interface 2790, the user may take one or more actions to mute the alarm signal and/or acknowledge the alarm.

The screen interface 2790 may include controls for user adjustment of parameter settings and/or alarm set points at the RD hub 1710b or 1710c. For example, the interface 2790 may include user inputs that correspond to the setting inputs 2722a-g so that a user can adjust values for the ventilation system settings 2704, 2706, 2708, 2709, 2710, 2712, and 2713. In some implementations, the user interface screen 2790 may also include a user input that corresponds to a manual breath button/plateau pressure input 2728 that causes the RD hub 1710b or 1710c to deliver a manual breath to the patient and/or measure plateau pressure.

Figure 18:
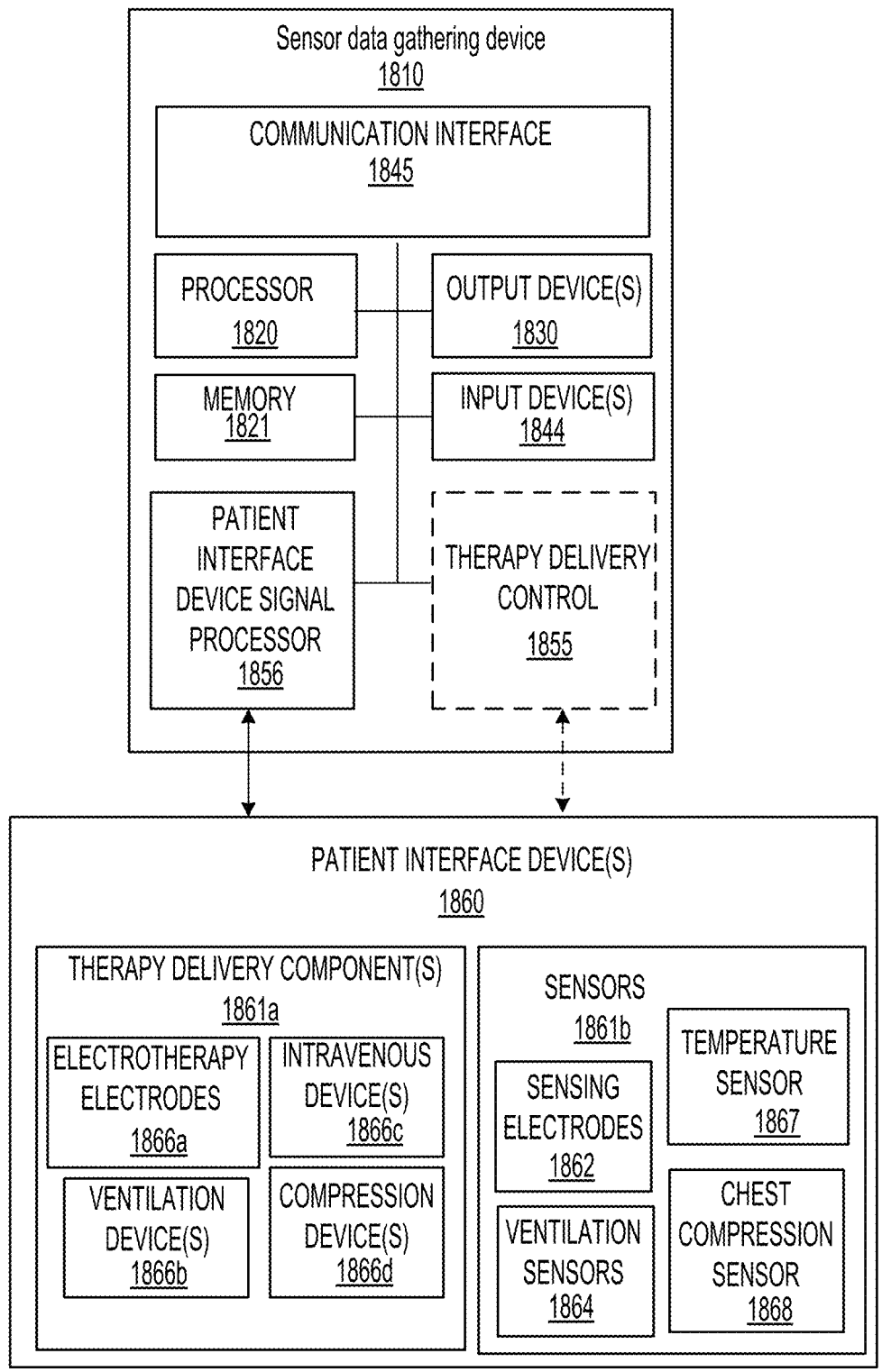
FIG. 18 shows a schematic diagram of examples of components of a sensor data gathering device.

Referring to FIG. 18, examples of components of a sensor data gathering device 1810 (e.g., the medical device 110, the sensor hub 1010, and/or the RD hub 1710, 1710a, 1710b, and/or 1710c) are shown schematically. The device 1810 may include at least one processor 1820, at least one memory 1821, one or more output devices 1830, one or more user input devices 1844, and at least one communication interface 1845.

In various implementations, the medical device 110 may be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 110 may be an integrated therapy delivery/monitoring device within a single housing (e.g., the single housing 1020, as shown in FIG. 10). The single housing may surround, at least in part, the therapy delivery components and the monitoring components. In an implementation, the medical device 110 may be a modular therapy delivery/monitoring device, with patient therapy components in one unit communicatively coupled to a patient monitoring unit without therapy delivery components.

The medical device 110 may be, for example, a therapeutic medical device capable of delivering a medical therapy. For example, the medical therapy may be electrical therapy (e.g. defibrillation, cardiac pacing, synchronized cardioversion, diaphragmatic or phrenic nerve stimulation) and the medical device 110 may be a defibrillator, a defibrillator/monitor, a mechanical ventilator such as the ZOLL Z-Vent, and/or another medical device configured to provide electrotherapy. As another example, the medical therapy may be chest compression therapy for treatment of cardiac arrest and the medical device 110 may be a mechanical chest compression device such as a belt-based chest compression device or a piston-based chest compression device. As other examples, the medical therapy may be ventilation therapy, therapeutic cooling or other temperature management, invasive hemodynamic support therapy (e.g. Extracorporeal Membrane Oxygenation (ECMO)), etc. and the medical device 110 may be a device configured to provide a respective therapy. In an implementation, the medical device 110 may be a combination of one or more of these examples. The therapeutic medical device may include patient monitoring capabilities via one or more sensors. These types of medical therapy and devices are examples only and not limiting of the disclosure.

The patient interface device(s) 1860 may include one or more therapy delivery component(s) 1861a and/or one or more sensor device(s) 1861b. The therapy delivery component(s) 1861a are configured to deliver therapy to the patient and may be configured to couple to the patient. For example, the therapy delivery component(s) 1861a may include one or more of electrotherapy electrodes including defibrillation electrodes and/or pacing electrodes, chest compression devices (e.g., one or more belts or a piston), ventilation devices (e.g., a mask and/or tubes), drug delivery devices, etc. The medical device 110 may include the one or more therapy delivery component (s) 1861a and/or may be configured to couple to the one or more therapy delivery component(s) 1861a in order to provide medical therapy to the patient. The therapy delivery component(s) 1861a may be configured to couple to the patient 170. For example, the caregiver 180 may attach the electrodes to the patient 170 and the medical device 110 (e.g., a defibrillator or defibrillator/patient monitor) may provide electrotherapy to the patient 170 via the defibrillation electrodes. These examples are not limiting of the disclosure as other types of medical devices, therapy delivery components, sensors, and therapy are within the scope of the disclosure.

The device 1810 may include, incorporate, and/or be configured to couple to the one or more sensor(s) 1861b (e.g., sensor(s) 220 and 1520) which may be configured to couple to the patient 170. The sensor(s) 161b are configured to provide signals indicative of sensor data to the device 1810. The sensor(s) 1861b may be configured to couple to the patient. For example, the sensor(s) 1861b may include cardiac sensing electrodes, a chest compression sensor, and/or ventilation sensors. The cardiac sensing electrodes may be conductive and/or capacitive electrodes configured to measure changes in a patient's electrophysiology to measure the patient's ECG information. The sensing electrodes may further measure the transthoracic impedance and/or a heart rate of the patient. The one or more sensors 1861b may generate signals indicative of physiological parameters of the patient 170. For example, the physiological parameters may include one or more of at least one vital sign, an ECG, blood pressure, heart rate, pulse oxygen level, respiration rate, heart sounds, lung sounds, respiration sounds, tidal $CO_2$, saturation of muscle oxygen ($SMO_2$), arterial oxygen saturation ($SpO_2$), cerebral blood flow, electroencephalogram (EEG) signals, brain oxygen level, tissue pH, tissue fluid levels, physical parameters as determined via ultrasound images, parameters determined via near-infrared reflectance spectroscopy, pneumography, and/or cardiography, etc. The ultrasound images may include ultrasound images of a patient's heart, carotid artery, and/or other components of the cardiovascular system. Additionally or alternatively the one or more sensors 1861b may generate signals indicative of chest compression parameters, ventilation parameters, drug delivery parameters, fluid delivery parameters, etc.

In addition to delivering therapy to the patient, the therapy delivery component(s) 1861a may include, be coupled to, and/or function as sensors and provide signals indicative of sensor data to the device 1810. For example, the defibrillation electrodes may be configured as cardiac sensing electrodes as well as electrotherapy delivery devices and may provide signals indicative of transthoracic impedance, electrocardiogram (ECG), heart rate and/or other physiological parameters. As another example, a therapeutic cooling device may be an intravenous cooling device. Such a cooling device may include an intravenous (IV) device as a therapy delivery component configured to deliver cooling therapy and sense the patient's temperature. For example, the IV device may be a catheter that includes saline balloons configured to adjust the patient's temperature via circulation of temperature controlled saline solution. In addition, the catheter may include a temperature probe configured to sense the patient's temperature. As a further example, an IV device may provide therapy via drug delivery and/or fluid management. The IV device may also monitor and/or enabling monitoring of a patient via blood sampling and/or venous pressure monitoring (e.g., central venous pressure (CVP) monitoring).

The device 1810 may be configured to receive the sensor signals (e.g., from the therapy delivery component(s) 1861*a* and/or the sensor(s) 1861*b*) and to process the sensor signals to determine and collect the patient data. The patient data may include patient data which may characterize a status and/or condition of the patient (e.g., physiological data such as ECG, heart rate, respiration rate, temperature, pulse oximetry, non-invasive hemoglobin parameters, capnography, oxygen saturation (SpO2), end tidal carbon dioxide (EtCO2), invasive blood pressure (IBP), non-invasive blood pressures (NIBP), tissue pH, tissue oxygenation, Near Infrared Spectroscopy (NIRS) measurements, etc.). Additionally or alternatively, the patient data may characterize the delivery of therapy (e.g., chest compression data such as compression depth, compression rate, etc.) and/or the patient data may characterize a status and/or condition of the medical equipment used to treat the patient (e.g., device data such as shock time, shock duration, attachment of electrodes, power-on, etc.).

The components of 1820, 1821, 1830, 1844, 1845, and 1855 of the device 1810 are communicatively coupled (directly and/or indirectly) to each other for bi-directional communication. Although shown as separate entities in FIG. 18, the one or more of the components of the device 1810 may be combined into one or more discrete components and/or may be part of the processor 1820. The processor 1820 and the memory 1821 may include and/or be coupled to associated circuitry in order to perform the functions described herein.

In an implementation, the device 1810 may be the medical device 110 configured to deliver medical therapy to the patient 170. Thus, the medical device 110 may include the therapy delivery control module 1855. For example, the therapy delivery control module 1855 may be an electrotherapy delivery circuit that includes one or more capacitors configured to store electrical energy for a pacing pulse or a defibrillating pulse. The electrotherapy delivery circuit may further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 1855 may be a compression device electro-mechanical controller configured to control a mechanical compression device. As a further example, the therapy delivery control module 1855 may be an electro-mechanical controller configured to control drug delivery, temperature management, ventilation, and/or other type of therapy delivery. Alternatively, the medical device 110 may be configured to provide patient monitoring and/or diagnostic care without providing medical therapy.

The one or more therapy delivery components 1861*a* may include electrotherapy electrodes (e.g., the electrotherapy electrodes 166*a*), ventilation device(s) (e.g., the ventilation devices 1866*b*), intravenous device(s) (e.g., the intravenous devices 1866*c*), compression device(s) (e.g., the compression devices 1866*d*), etc. For example, the electrotherapy electrodes may include defibrillation electrodes, pacing electrodes, and/or combinations thereof. The ventilation devices may include a tube, a mask, an abdominal and/or chest compressor (e.g., a belt, a cuirass, etc.), a mechanical ventilator, etc. and combinations thereof. As an example, the mechanical ventilator may be a portable, battery powered ventilator. The intravenous devices may include drug delivery devices, fluid delivery devices, and combinations thereof. The compression devices may include mechanical compression devices such as abdominal compressors, chest compressors, belts, pistons, and combinations thereof. In various implementation, the therapy delivery component(s) 1861*a* may be configured to provide sensor data and/or be coupled to and/or incorporate sensors. For example, the electrotherapy electrodes may provide sensor data such as transthoracic impedance, ECG, heart rate, etc. Further the electrotherapy electrodes may include and or be coupled to a chest compression sensor. As another example, the ventilation devices may be coupled to and/or incorporate flow sensors, gas species sensors (e.g., oxygen sensor, carbon dioxide sensor, etc.), etc. As a further example, the intravenous devices may be coupled to and/or incorporate temperature sensors, flow sensors, blood pressure sensors, etc. As yet another example, the compression devices may be coupled to and/or incorporate chest compression sensors, patient position sensors, etc. The therapy delivery control module 1855 may be configured to couple to and control the therapy delivery component(s) 1861*a*.

In various implementations, the sensor(s) 1861*b* may include one or more sensor devices configured to provide sensor data that includes, for example, but not limited to electrocardiogram (ECG), blood pressure, heart rate, pulse oxygen level, respiration rate, heart sounds, lung sounds, respiration sounds, tidal $CO_2$, saturation of muscle oxygen ($SMO_2$), arterial oxygen saturation ($SpO_2$), cerebral blood flow, electroencephalogram (EEG) signals, brain oxygen level, tissue pH, tissue fluid levels, images and/or videos via ultrasound, laryngoscopy, and/or other medical imaging techniques, near-infrared reflectance spectroscopy, pneumography, cardiography, and/or patient movement. Images and/or videos may be two-dimensional or three-dimensional.

The sensor(s) 1861*b* may include sensing electrodes, ventilation sensors, temperature sensors, chest compression sensors, etc. For example, the sensing electrodes may include cardiac sensing electrodes. The cardiac sensing electrodes may be conductive and/or capacitive electrodes configured to measure changes in a patient's electrophysiology, for example to measure the patient's ECG information. In an implementation, the sensing electrodes may be configured to measure the transthoracic impedance and/or a heart rate of the patient 170. The ventilation sensors may include spirometry sensors, flow sensors, pressure sensors, oxygen and/or carbon dioxide sensors such as, for example, one or more of pulse oximetry sensors, oxygenation sensors (e.g., muscle oxygenation/pH), O2 gas sensors and capnography sensors, and combinations thereof. The temperature sensors may include an infrared thermometer, a contact thermometer, a remote thermometer, a liquid crystal thermometer, a thermocouple, a thermistor, etc. and may measure patient temperature internally and/or externally. The chest compression sensor may include one or more motion sensors including, for example, one or more accelerometers, one or more force sensors, one or more magnetic sensors, one or more velocity sensors, one or more displacement sensors, etc. The chest compression sensor may be, for example, but not limited to, a compression puck, a smartphone, a hand-held device, a wearable device, etc. The chest compression sensor may be configured to detect chest motion imparted by a rescuer and/or an automated chest compression device (e.g., a belt system, a piston system, etc.). The chest compression sensor may provide signals indicative of chest compression data including displacement data, velocity data, release velocity data, acceleration data, compression rate data, dwell time data, hold time data, blood flow data, blood pressure data, etc. In an implementation, the sensing electrodes and/or the electrotherapy electrodes may include or be configured to couple to the chest compression sensor.

The patient data provided at the operational interface and/or playback interface may include the patient data provided via the one or more therapy delivery component(s) 1861*a* and/or the one or more sensor(s) 1861*b*. For example, the medical device 110 may process signals received from the therapy delivery component(s) 1861*a* and/or the sensor(s) 1861*b* to determine the patient data.

In various implementations, the device 1810 may couple to other computing devices (e.g., the devices 1412 or 1414). These other computing devices may be a medical device or a computing device (e.g., personal computer, a laptop computer, a mobile device, a hand-held device, a wireless device, a tablet computer, a wearable device such as a wrist-worn device, a head-worn device, heads up display, etc., or combinations thereof) adapted for medical use. The other medical devices 1414 may incorporate and/or be configured to couple to one or more patient interface device(s) substantially as described for the patient interface device(s) 1860.

Referring to FIGS. 2A, 4, 10, and 18, the processors as described herein (e.g., 265, 425, 1036, 1050, and 1820) are physical processors (i.e., one or more integrated circuits configured to execute operations on a respective device (e.g., 110, 210, 410, 1010, 1810) as specified by software and/or firmware stored in a computer storage medium) operably coupled, respectively, to at least one memory device (e.g., 266, 426, 1038, 1052, and 1821). The processors may be intelligent hardware devices (for example, but not limited to, a central processing unit (CPU), a graphics processing unit (GPU), one or more microprocessors, a controller or microcontroller, an application specific integrated circuit (ASIC), a digital signal processor (DSP), etc.) designed to perform the functions described herein and operable to carry out instructions on a respective device. Each of the processors may be one or more processors and may be implemented as a combination of hardware devices (e.g., a combination of DSP and a microprocessor, a plurality of microprocessors, one or more microprocessors in conjunction with a DSP core, or another such configuration). Each of the processors may include multiple separate physical entities that may be distributed in the cable 210 or devices 110, 1010, or 1810. Each of the processors is configured to execute processor-readable, processor-executable software code containing one or more instructions or code for controlling the processors to perform the functions as described herein. The processors may utilize various architectures including but not limited to a complex instruction set computer (CISC) processor, a reduced instruction set computer (RISC) processor, or a minimal instruction set computer (MISC). In various implementations, each processor may be a single-threaded or a multi-threaded processor. The processors may be, for example, but not limited to, an Intel® Itanium® or Itanium 2® processor(s), AMD® Opteron®, Athlon MP® processor(s), a Motorola® line of processor, or an ARM, Intel Pentium Mobile, Intel Core i5 Mobile, AMD A6 Series, AMD Phenom II Quad Core Mobile, or like devices.

The device 1810 may include a patient interface device signal processor 1856. The patient interface device signal processor 1856 may include A/D converters and other hardware configured to receive and process signals from one or more of the patient interface devices 1860.

The memories (e.g., memory 266, 426, 1038, 1052, and 1821) refer generally to a computer storage medium, including but not limited to RAM, ROM, FLASH, disc drives, fuse devices, and portable storage media, such as Universal Serial Bus (USB) flash drives, etc. Each of the memories may include, for example, random access memory (RAM), or another dynamic storage device(s) and may include read only memory (ROM) or another static storage device(s) such as programmable read only memory (PROM) chips for storing static information such as instructions for a coupled processor. Each memory may include USB flash drives that may store operating systems and other applications. The USB flash drives may include input/output components, such as a wireless transmitter and/or USB connector that can be inserted into a USB port of another computing device. Each memory may be long term and/or short term are not to be limited to a particular type of memory or number of memories, or type of media upon which memory is stored. Each memory includes a non-transitory processor-readable storage medium (or media) that stores the processor-readable, processor-executable software code. Each memory may store information and instructions. For example, each memory may include flash memory and/or another storage media may be used, including removable or dedicated memory in a mobile or portable device. As another example, hard disks such as the Adaptec® family of SCSI drives, an optical disc, an array of disks such as RAID (e.g. the Adaptec family of RAID drives), or another mass storage devices may be used. Each memory may include removable storage media such as, for example, external hard-drives, floppy drives, flash drives, zip drives, compact disc-read only memory (CD-ROM), compact disc-re-writable (CD-RW), or digital video disk-read only memory (DVD-ROM).

The communication interface 1845 may transmit and/or receive information to and/or from one or more devices external to and communicatively coupled to the device 1810. The communication interface 1845 may transmit and/or receive the information via a wired and/or wireless communicative coupling. The information may include information stored in at least one of the memories described above. The information may include, for example, but not limited to, resuscitative treatment information, physiological information, patient information, rescuer and/or caregiver information, location information, rescue and/or medical treatment center information, etc. The communication interface 1845 may enable short-range and/or long-range wireless communication capabilities which may include communication via near field communication, ZigBee®, Wi-Fi, Bluetooth®, satellite(s), radio waves, a computer network (e.g., the Internet), a cellular network, etc. The communication interface 1845 may enable communication via a network such a Local Area Network (LAN), Wide Area Network (WAN), a mesh network, an ad hoc network, or another network. The communication interface 1845 may include, for example, an RS-232 port for use with a modem based dialup connection, a copper or fiber 10/100/1000 Ethernet port, or a Bluetooth® or WiFi interface.

In an implementation, the communication interface 1845 may enable communication with one or more other computing or medical devices. The communication interface 1845 may be the communication interface 1034 or 1054 as described above with regard to FIGS. 10 and 11.

The output device(s) 1830 and user input device(s) 1844 may be included in the device 1810 and/or coupled to the device 1810. The output device(s) 1830 may include one or more of a display, a speaker, and a haptic device. The display may be a display screen. The medical device 110 may provide at least one first display screen and the sensor hub 1010 may provide at least one second display screen. The display may provide a graphical user interface (GUI). The display may be, for example, but not limited to, a liquid crystal display (LCD) and/or a light emitting diode (LED) display. In an implementation, the output device(s) 1830 may be input/output device(s) capable of capturing user input. For example, the display (e.g., 150 or 1540) may be a touchscreen. The touchscreen may be, for example, a pressure sensitive touchscreen or a capacitive touchscreen. The touchscreen may capture user input provided via touchscreen gestures and/or provided via exertions of pressure on a particular area of the screen. Examples of touchscreen gestures that may enable user input may include pushing on the touchscreen to exert pressure that exceeds a particular threshold to indicate an input to a pressure sensitive touchscreen by the user. The touchscreen and a respective controlling processor may be configured recognize touchscreen gestures including, for example, but not limited to, tap, double tap, caliper gesture, drag and drop, slide, press and drag, hold and press, etc. In an implementation, the processor 1820 may control a respective display to provide visual representations of data captured by and/or received at the device 1810. The visual representations may include still images and/or video images (e.g., animated images).

In an implementation, the output device(s) 1830 and/or the input device(s) 1844 may include wearable devices such as, for example, a heads-up display mounted onto eyeglasses, a face shield, a watch, and/or devices that may be integrated with other wearable communication devices, such as, for example, an ear bud or a Bluetooth® hands free phone adaptor. The processor 1820 may control the output devices 1830 respectively, to provide information for the user. The information may include feedback (e.g., visible feedback, audible feedback, haptic feedback, textual feedback, numerical feedback, and graphical feedback) such as CPR feedback.

The one or more user input devices 1844 may include, for example, a keyboard, a mouse, joystick, trackball, or other pointing device, a microphone, a camera, etc. Further, the user input devices 1844 may be a touchscreen and/or another input/output device capable of providing information for the user and capturing information from the user. The touchscreen may be a pressure sensitive touchscreen In an implementation, the user input devices 1844 may be configured to capture information, such as, for example, patient medical history (e.g., medical record information including age, gender, weight, body mass index, family history of heart disease, cardiac diagnosis, co-morbidity, left ventricular ejection fraction, medications, previous medical treatments, and/or other physiological information), physical examination results, patient identification, caregiver identification, healthcare facility information, etc.

The processor, memory, communication interfaces, input and/or output devices and other components described above are meant to exemplify some types of possibilities. In no way should the aforementioned examples limit the scope of the disclosure, as they are only exemplary embodiments of these components.

Various modifications and additions can be made to the exemplary embodiments discussed without departing from the scope of the present disclosure. For example, while the embodiments described above refer to particular features, the scope of the disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A data transfer cable for providing data communications between a sensor for collecting medical data and a sensor-agnostic data interface (DI) port on a medical device, the data transfer cable comprising:
    a cable comprising conductive wires disposed within a continuous insulative sheath;
    a first electromechanical connector fixedly fastened to a first end of the cable, the first electromechanical connector comprising:
        a housing,
        a first electrical mating disposed within the housing at an open end of the housing and configured to detachably couple to the sensor,
        data interface circuitry disposed within the housing and electrically coupled to the first electrical mating and to the conductive wires of the cable, the data interface circuitry comprising:
        a cable memory,
        a cable processor, and
        an isolation device for limiting patient leakage current flow from the medical device to the sensor, the isolation device configured to:
    transfer power across an isolation barrier uni-directionally towards the cable processor, and
    transmit communication signals bi-directionally across the isolation barrier; and
    a second electromechanical connector fixedly fastened to a second end of the cable, the second electromechanical connector comprising cable contacts electrically coupled to the conductive wires of the cable and configured to detachably electromechanically couple the data transfer cable to the sensor-agnostic DI port.

2. The data transfer cable of claim 1, wherein the isolation device is configured to transmit an amount of power specific to the sensor across the isolation barrier.

3. The data transfer cable of claim 2, wherein the isolation device is configured to transmit 0.1-1 watts.

4. The data transfer cable of claim 1, wherein the isolation device comprises one of a double capacitive isolation barrier device, a digital isolator device, and an optical isolator.

5. The data transfer cable of claim 1, wherein the cable contacts comprise at least:
    (a) at least two communication cable contacts,
    (b) at least one power cable contact, and
    (c) at least one ground cable contact,
    wherein each of the cable contacts is electrically coupled to at least one of the conductive wires.

6. The data transfer cable of claim 5, wherein the cable contacts include at least one connection detection cable contact for electrically detecting a connection between the data transfer cable and the sensor-agnostic DI port.

7. The data transfer cable of claim 5, wherein the data interface circuitry comprises an authentication circuit and wherein the cable contacts comprise at least one authentication cable contact.

8. The data transfer cable of claim 7, wherein the authentication circuit is configured to: (a) receive an AU/ID request via the at least one authentication cable contact, and
- (b) send AU/ID information in response to the received AU/ID request,
- in an absence of power transmission to the data transfer cable from the sensor-agnostic DI port.

9. The data transfer cable of claim 8, wherein the authentication circuit is configured to include encrypted AU/ID information for the sensor in the AU/ID information.

10. The data transfer cable of claim 9, wherein the encrypted AU/ID information comprises identification information for a manufacturer of the sensor.

11. The data transfer cable of claim 1, wherein the cable processor is configured to:
- receive, from the sensor-agnostic DI port via the communication signals transmitted by the isolation device, a request for sensor information comprising unencrypted AU/ID information stored in the cable memory,
- execute software stored in the cable memory to determine the requested sensor information, and
- send the sensor information to the sensor-agnostic DI port via the communication signals transmitted by the isolation device.

12. The data transfer cable of claim 11, wherein the cable processor is configured to:
- receive a request for sensor data streams from the sensor-agnostic DI port via the communication signals transmitted by the isolation device,
- execute software stored in the cable memory to format sensor data in a sensor-agnostic data format according to a protocol of the sensor-agnostic DI port, and send the sensor data streams in the sensor-agnostic data format to the sensor-agnostic DI port via the communication signals transmitted by the isolation device.

13. The data transfer cable of claim 1, wherein the data interface circuitry comprises an analog-to-digital converter.

14. The data transfer cable of claim 1, comprising a noise shield between the isolation device and the cable processor.

15. The data transfer cable of claim 1, comprising:
- at least one illumination device disposed on the cable and configured to illuminate in a color based on a type of the sensor.

16. The data transfer cable of claim 15, wherein the at least one illumination device includes a light emitting diode (LED).

17. The data transfer cable of claim 16, wherein the at least one illumination device comprises a band that surrounds a circumference of the data transfer cable.

18. The data transfer cable of claim 15, comprising a microphone communicatively coupled to the cable processor and configured to capture voice input, wherein the cable processor is configured to cause the at least one illumination device to illuminate in response to the voice input.

19. The data transfer cable of claim 18, wherein the cable processor is configured to recognize a sensor identification query from the voice input.

20. The data transfer cable of claim 15, wherein the at least one illumination device provides infrared illumination.

21. The data transfer cable of claim 15 comprising a low light sensor electrically coupled to the at least one illumination device and configured to disable illumination under low light conditions.

22. The data transfer cable of claim 1, comprising a user interface display configured to provide caregiver feedback and disposed on a display housing positioned along the cable.

23. The data transfer cable of claim 22, wherein the caregiver feedback comprises one or more of cardiopulmonary resuscitation chest compression feedback and bag valve mask feedback.

24. The data transfer cable of claim 1, wherein the sensor is one of an invasive blood pressure sensor, a non-invasive blood pressure sensor, a temperature sensor, a pulse oximetry sensor, a capnography sensor, and an airway flow sensor.

25. The data transfer cable of claim 1, wherein the sensor is an ECG sensor.

* * * * *